(12) United States Patent
Bonk et al.

(10) Patent No.: US 8,735,421 B2
(45) Date of Patent: *May 27, 2014

(54) IMIDAZOQUINOLINYL SULFONAMIDES

(75) Inventors: Jason D. Bonk, Hudson, WI (US); Joseph F. Dellaria, Jr., Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1865 days.

This patent is subject to a terminal disclaimer.

(21) Appl. No.: 10/596,897

(22) PCT Filed: Dec. 23, 2004

(86) PCT No.: PCT/US2004/043447
§ 371 (c)(1),
(2), (4) Date: Jun. 28, 2006

(87) PCT Pub. No.: WO2005/066169
PCT Pub. Date: Jul. 21, 2005

(65) Prior Publication Data
US 2009/0062272 A1    Mar. 5, 2009

Related U.S. Application Data

(60) Provisional application No. 60/533,465, filed on Dec. 30, 2003, provisional application No. 60/555,936, filed on Mar. 24, 2004, provisional application No. 60/581,335, filed on Jun. 18, 2004.

(51) Int. Cl.
*A61K 31/437*    (2006.01)
*C07D 487/04*    (2006.01)

(52) U.S. Cl.
USPC .......................................... 514/290; 546/80

(58) Field of Classification Search
USPC ........................................... 546/80; 514/290
See application file for complete search history.

(56) References Cited

U.S. PATENT DOCUMENTS

| | | | |
|---|---|---|---|
| 3,314,941 A | 4/1967 | Littell et al. | |
| 3,450,693 A | 6/1969 | Suzuki et al. | |
| 3,670,086 A | 6/1972 | Pryor et al. | |
| 3,692,907 A | 9/1972 | Fleming et al. | |
| 3,891,660 A | 6/1975 | Denzel et al. | |
| 3,899,508 A | 8/1975 | Wikel | |
| 3,917,624 A | 11/1975 | Abu El-Haj et al. | |
| 4,006,237 A | 2/1977 | Buckle et al. | |
| 4,053,588 A | 10/1977 | Konig et al. | |
| 4,381,344 A | 4/1983 | Rideout et al. | |
| 4,552,874 A | 11/1985 | Mardin et al. | |
| 4,563,525 A | 1/1986 | Campbell, Jr. | |
| 4,593,821 A | 6/1986 | Brule | |
| 4,668,686 A | 5/1987 | Meanwell et al. | |
| 4,689,338 A * | 8/1987 | Gerster | 514/293 |
| 4,690,930 A | 9/1987 | Takada et al. | |
| 4,698,346 A | 10/1987 | Musser et al. | |
| 4,698,348 A * | 10/1987 | Gerster | 514/293 |
| 4,753,951 A | 6/1988 | Takada et al. | |
| 4,758,574 A | 7/1988 | Robertson et al. | |
| 4,774,339 A | 9/1988 | Haugland et al. | |
| 4,775,674 A | 10/1988 | Meanwell et al. | |
| 4,800,206 A | 1/1989 | Alig et al. | |
| 4,826,830 A | 5/1989 | Han et al. | |
| 4,837,378 A | 6/1989 | Borgman | |
| 4,880,779 A | 11/1989 | Gallaher | |
| 4,904,669 A | 2/1990 | Knoll et al. | |
| 4,929,624 A * | 5/1990 | Gerster et al. | 514/293 |
| 4,988,714 A | 1/1991 | Alig et al. | |
| 4,988,815 A | 1/1991 | Andre et al. | |
| 5,037,986 A * | 8/1991 | Gerster | 546/82 |
| 5,175,296 A | 12/1992 | Gerster | |
| 5,187,288 A | 2/1993 | Kang et al. | |
| 5,225,183 A | 7/1993 | Purewal et al. | |
| 5,238,944 A | 8/1993 | Wick et al. | |
| 5,248,782 A | 9/1993 | Haugland et al. | |
| 5,266,575 A | 11/1993 | Gerster | |
| 5,268,376 A * | 12/1993 | Gester | 514/293 |
| 5,274,113 A | 12/1993 | Kang et al. | |
| 5,342,784 A | 8/1994 | Yamada et al. | |
| 5,346,905 A * | 9/1994 | Gerster | 514/293 |
| 5,352,680 A | 10/1994 | Portoghese et al. | |
| 5,352,784 A | 10/1994 | Nikolaides et al. | |
| 5,367,076 A | 11/1994 | Gerster | |
| 5,376,501 A | 12/1994 | Marien et al. | |
| 5,378,848 A | 1/1995 | Takada et al. | |
| 5,389,640 A * | 2/1995 | Gerster et al. | 514/293 |
| 5,395,937 A | 3/1995 | Nikolaides et al. | |

(Continued)

FOREIGN PATENT DOCUMENTS

AU    2004220534 A1    9/2004
AU    2004229478 A1    10/2004

(Continued)

OTHER PUBLICATIONS

Dorwald F. A. Side Reactions in Organic Synthesis, 2005, Wiley: VCH, Weinheim p. IX of Preface.*
Wermuth C. Molecular Variations based on Isosteric Replacements. 1996.*
Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.
Brennan et al., "Automated Bioassay of Interferons in Micro-test Plates.", *Biotechniques*, June/July, 78, 1983.
Testerman et al., "Cytokine Induction by the Immunomodulators Imiquimod and S-27609.", *Journal of Leukocyte Biology*, vol. 58, pp. 365-372, Sep. 1995.

(Continued)

Primary Examiner — Rita Desai

(57) ABSTRACT

Imidazoquinolinyl, imidazopyridinyl, and imidazonaphthyridinyl sulfonamide compounds, pharmaceutical compositions containing the compounds, intermediates, and methods of making and methods of use of these compounds as immunomodulators, for inducing cytokine biosynthesis in animals and in the treatment of diseases including viral and neoplastic diseases are disclosed.

36 Claims, No Drawings

(56) References Cited

U.S. PATENT DOCUMENTS

| | | | |
|---|---|---|---|
| 5,444,065 A | 8/1995 | Nikolaides et al. |
| 5,446,153 A | 8/1995 | Llindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 * | 2/2003 | Dellaria et al. ............... 514/303 |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |

(56) References Cited

U.S. PATENT DOCUMENTS

| | | | |
|---|---|---|---|
| 7,078,253 B2 | 7/2006 | Brunner et al. | |
| 7,091,214 B2 * | 8/2006 | Hays et al. | 514/293 |
| 7,098,221 B2 | 8/2006 | Heppner et al. | |
| 7,112,677 B2 | 9/2006 | Griesgraber | |
| 7,115,622 B2 | 10/2006 | Crooks et al. | |
| 7,125,890 B2 | 10/2006 | Dellaria et al. | |
| 7,132,429 B2 | 11/2006 | Griesgraber et al. | |
| 7,163,947 B2 | 1/2007 | Griesgraber et al. | |
| 7,179,253 B2 | 2/2007 | Graham et al. | |
| 7,199,131 B2 | 4/2007 | Lindstrom | |
| 7,214,675 B2 | 5/2007 | Griesgraber | |
| 7,220,758 B2 | 5/2007 | Dellaria et al. | |
| 7,226,928 B2 | 6/2007 | Mitra et al. | |
| 7,276,515 B2 | 10/2007 | Dellaria et al. | |
| 7,288,550 B2 | 10/2007 | Dellaria et al. | |
| 7,375,180 B2 | 5/2008 | Gorden et al. | |
| 7,387,271 B2 | 6/2008 | Noelle et al. | |
| 7,393,859 B2 | 7/2008 | Coleman et al. | |
| 7,427,629 B2 | 9/2008 | Kedl et al. | |
| 7,544,697 B2 | 6/2009 | Hays et al. | |
| 7,598,382 B2 | 10/2009 | Hays et al. | |
| 7,612,083 B2 | 11/2009 | Griesgraber | |
| 7,648,997 B2 | 1/2010 | Kshirsagar et al. | |
| 2001/0046968 A1 | 11/2001 | Zagon et al. | |
| 2002/0016332 A1 | 2/2002 | Slade | |
| 2002/0055517 A1 | 5/2002 | Smith | |
| 2002/0058674 A1 | 5/2002 | Hedenstrom et al. | |
| 2002/0107262 A1 | 8/2002 | Lindstrom | |
| 2002/0110840 A1 | 8/2002 | Tomai et al. | |
| 2002/0137101 A1 | 9/2002 | Meyers | |
| 2002/0173655 A1 | 11/2002 | Dellaria et al. | |
| 2002/0193729 A1 | 12/2002 | Cormier et al. | |
| 2003/0022302 A1 | 1/2003 | Lewis et al. | |
| 2003/0044429 A1 | 3/2003 | Aderem et al. | |
| 2003/0082108 A1 | 5/2003 | Mulshine et al. | |
| 2003/0088102 A1 | 5/2003 | Matsubara et al. | |
| 2003/0096835 A1 | 5/2003 | Crooks et al. | |
| 2003/0096998 A1 | 5/2003 | Gerster et al. | |
| 2003/0130299 A1 | 7/2003 | Crooks et al. | |
| 2003/0133733 A1 | 7/2003 | Korhonen | |
| 2003/0133913 A1 | 7/2003 | Tomai et al. | |
| 2003/0139364 A1 | 7/2003 | Krieg et al. | |
| 2003/0144283 A1 | 7/2003 | Coleman et al. | |
| 2003/0144286 A1 | 7/2003 | Frenkel et al. | |
| 2003/0158192 A1 | 8/2003 | Crooks et al. | |
| 2003/0161797 A1 | 8/2003 | Miller et al. | |
| 2003/0172391 A1 | 9/2003 | Turner et al. | |
| 2003/0185835 A1 | 10/2003 | Braun | |
| 2003/0187016 A1 | 10/2003 | Crooks et al. | |
| 2003/0199461 A1 | 10/2003 | Averett et al. | |
| 2003/0199538 A1 | 10/2003 | Skwierczynski et al. | |
| 2003/0212092 A1 | 11/2003 | Heppner et al. | |
| 2003/0216481 A1 | 11/2003 | Jia | |
| 2003/0232074 A1 | 12/2003 | Lipford et al. | |
| 2003/0232763 A1 | 12/2003 | Jia | |
| 2003/0232852 A1 | 12/2003 | Lindstrom et al. | |
| 2004/0010007 A1 | 1/2004 | Dellaria et al. | |
| 2004/0014779 A1 | 1/2004 | Gorden et al. | |
| 2004/0023870 A1 | 2/2004 | Dedera et al. | |
| 2004/0067975 A1 | 4/2004 | Crooks et al. | |
| 2004/0072858 A1 | 4/2004 | Charles et al. | |
| 2004/0076633 A1 | 4/2004 | Thomsen et al. | |
| 2004/0091491 A1 | 5/2004 | Kedl et al. | |
| 2004/0092545 A1 | 5/2004 | Crooks et al. | |
| 2004/0097542 A1 | 5/2004 | Crooks et al. | |
| 2004/0106638 A1 | 6/2004 | Lindstrom | |
| 2004/0132079 A1 | 7/2004 | Gupta et al. | |
| 2004/0132748 A1 | 7/2004 | Isobe et al. | |
| 2004/0132766 A1 | 7/2004 | Griesgraber | |
| 2004/0141950 A1 | 7/2004 | Noelle et al. | |
| 2004/0147543 A1 | 7/2004 | Hays et al. | |
| 2004/0157874 A1 | 8/2004 | Crooks et al. | |
| 2004/0162309 A1 | 8/2004 | Gorden et al. | |
| 2004/0167157 A1 | 8/2004 | Masui et al. | |
| 2004/0171086 A1 | 9/2004 | Fink et al. | |
| 2004/0175336 A1 | 9/2004 | Egging et al. | |
| 2004/0176367 A1 | 9/2004 | Griesgraber et al. | |
| 2004/0180919 A1 | 9/2004 | Lee et al. | |
| 2004/0181130 A1 | 9/2004 | Fox et al. | |
| 2004/0181211 A1 | 9/2004 | Elliott et al. | |
| 2004/0191833 A1 | 9/2004 | Fink et al. | |
| 2004/0192585 A1 | 9/2004 | Fox et al. | |
| 2004/0197865 A1 | 10/2004 | Gupta et al. | |
| 2004/0202720 A1 | 10/2004 | Wightman et al. | |
| 2004/0204436 A1 | 10/2004 | Gerster et al. | |
| 2004/0214851 A1 | 10/2004 | Birmachu et al. | |
| 2004/0258698 A1 | 12/2004 | Wightman et al. | |
| 2004/0265351 A1 | 12/2004 | Miller et al. | |
| 2005/0009858 A1 | 1/2005 | Martinez-Colon et al. | |
| 2005/0032829 A1 | 2/2005 | Lindstrom et al. | |
| 2005/0048072 A1 | 3/2005 | Kedl et al. | |
| 2005/0054590 A1 | 3/2005 | Averett | |
| 2005/0054640 A1 | 3/2005 | Griesgraber et al. | |
| 2005/0054665 A1 | 3/2005 | Miller et al. | |
| 2005/0059072 A1 | 3/2005 | Birmachu et al. | |
| 2005/0070460 A1 | 3/2005 | Hammerbeck et al. | |
| 2005/0085500 A1 | 4/2005 | Gutman et al. | |
| 2005/0096259 A1 | 5/2005 | Tomai et al. | |
| 2005/0119273 A1 | 6/2005 | Lipford et al. | |
| 2005/0136065 A1 | 6/2005 | Valiante | |
| 2005/0148620 A1 | 7/2005 | Crooks et al. | |
| 2005/0158325 A1 | 7/2005 | Hammerbeck et al. | |
| 2005/0165236 A1 | 7/2005 | Colombo et al. | |
| 2005/0171072 A1 | 8/2005 | Tomai et al. | |
| 2005/0226878 A1 | 10/2005 | Tomai et al. | |
| 2005/0234088 A1 | 10/2005 | Griesgraber | |
| 2005/0239733 A1 | 10/2005 | Jurk et al. | |
| 2005/0239735 A1 | 10/2005 | Miller et al. | |
| 2005/0245562 A1 | 11/2005 | Garcia-Echeverria et al. | |
| 2005/0267145 A1 | 12/2005 | Merrill et al. | |
| 2005/0281813 A1 | 12/2005 | Dedera et al. | |
| 2006/0009482 A1 | 1/2006 | Tomai et al. | |
| 2006/0100229 A1 | 5/2006 | Hays et al. | |
| 2006/0106052 A1 | 5/2006 | Crooks et al. | |
| 2007/0060754 A1 | 3/2007 | Lindstrom et al. | |
| 2007/0066639 A1 | 3/2007 | Kshirsagar et al. | |
| 2007/0072893 A1 | 3/2007 | Krepski et al. | |
| 2007/0099901 A1 | 5/2007 | Krepski et al. | |
| 2007/0155767 A1 | 7/2007 | Radmer et al. | |
| 2007/0167476 A1 | 7/2007 | Kshirsagar et al. | |
| 2007/0208052 A1 | 9/2007 | Prince et al. | |
| 2007/0213356 A1 | 9/2007 | Merrill et al. | |
| 2007/0219196 A1 | 9/2007 | Krepski et al. | |
| 2007/0219228 A1 | 9/2007 | Niwas et al. | |
| 2007/0259881 A1 | 11/2007 | Dellaria et al. | |
| 2007/0259907 A1 | 11/2007 | Prince | |
| 2007/0287725 A1 | 12/2007 | Miser et al. | |
| 2007/0292456 A1 | 12/2007 | Hammerbeck et al. | |
| 2008/0015184 A1 | 1/2008 | Kshirsagar et al. | |
| 2008/0070907 A1 | 3/2008 | Griesgraber et al. | |
| 2008/0085895 A1 | 4/2008 | Griesgraber et al. | |
| 2008/0114019 A1 | 5/2008 | Kshirsagar et al. | |
| 2008/0119508 A1 | 5/2008 | Slade et al. | |
| 2008/0207674 A1 | 8/2008 | Stoesz et al. | |
| 2008/0269192 A1 | 10/2008 | Griesgraber et al. | |
| 2008/0306252 A1 | 12/2008 | Crooks et al. | |
| 2008/0312434 A1 | 12/2008 | Lindstrom et al. | |
| 2008/0318998 A1 | 12/2008 | Prince et al. | |
| 2009/0005371 A1 | 1/2009 | Rice et al. | |
| 2009/0017076 A1 | 1/2009 | Miller et al. | |
| 2009/0018122 A1 | 1/2009 | Lindstrom et al. | |
| 2009/0023722 A1 | 1/2009 | Coleman et al. | |
| 2009/0029988 A1 | 1/2009 | Kshirsagar et al. | |
| 2009/0030030 A1 | 1/2009 | Bonk et al. | |
| 2009/0030031 A1 | 1/2009 | Kshirsagar et al. | |
| 2009/0042925 A1 | 2/2009 | Kshirsagar et al. | |
| 2009/0062328 A1 | 3/2009 | Kshirsagar et al. | |
| 2009/0069299 A1 | 3/2009 | Merrill et al. | |
| 2009/0069314 A1 | 3/2009 | Kshirsagar et al. | |
| 2009/0075980 A1 | 3/2009 | Hays et al. | |
| 2009/0099161 A1 | 4/2009 | Rice et al. | |
| 2009/0105295 A1 | 4/2009 | Kshirsagar et al. | |
| 2009/0124611 A1 | 5/2009 | Hays et al. | |
| 2009/0163532 A1 | 6/2009 | Perman et al. | |

(56) References Cited

U.S. PATENT DOCUMENTS

| | | |
|---|---|---|
| 2009/0163533 A1 | 6/2009 | Hays et al. |
| 2009/0176821 A1 | 7/2009 | Kshirsagar et al. |
| 2009/0240055 A1 | 9/2009 | Krepski et al. |
| 2009/0253695 A1 | 10/2009 | Kshirsagar et al. |
| 2009/0270443 A1 | 10/2009 | Stoermer et al. |
| 2009/0318435 A1 | 12/2009 | Hays et al. |
| 2010/0113565 A1 | 5/2010 | Gorden et al. |

FOREIGN PATENT DOCUMENTS

| | | |
|---|---|---|
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 | 10/1990 |
| EP | 0 425 306 A2 | 5/1991 |
| EP | 0 510 260 A2 | 10/1992 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 | 6/2001 |
| EP | 1 145 340 A2 | 10/2001 |
| EP | 1 256 582 A1 | 11/2002 |
| EP | 1 341 791 A2 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 4066571 A | 3/1992 |
| JP | 4327587 A | 11/1992 |
| JP | 5286973 A | 11/1993 |
| JP | 9-208584 | 8/1997 |
| JP | 11-080156 A | 3/1999 |
| JP | 11-222432 | 8/1999 |
| JP | 2000-247884 | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-96/11199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO 0076519 * | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO 02/36592 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO-03/050119 A2 | 6/2003 |
| WO | WO-03/050121 A1 | 6/2003 |
| WO | WO-03/077944 A1 | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A2 | 12/2003 |
| WO | WO-03/103584 A2 | 12/2003 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO-2005/023190 A2 | 3/2005 |
| WO | WO-2005/025614 A2 | 3/2005 |
| WO | WO-2005/029037 A2 | 3/2005 |
| WO | WO 2005/032484 | 4/2005 |
| WO | WO-2005/041891 A2 | 5/2005 |
| WO | WO 2005/048933 | 6/2005 |
| WO | WO 2005/048945 | 6/2005 |
| WO | WO-2005/049076 A1 | 6/2005 |
| WO | WO 2005/051317 | 6/2005 |
| WO | WO 2005/051324 | 6/2005 |
| WO | WO 2005/054237 | 6/2005 |

(56) References Cited

FOREIGN PATENT DOCUMENTS

| | | |
|---|---|---|
| WO | WO 2005/054238 | 6/2005 |
| WO | WO-2005/065678 A1 | 7/2005 |
| WO | WO 2005/066169 | 7/2005 |
| WO | WO 2005/066170 | 7/2005 |
| WO | WO 2005/066172 | 7/2005 |
| WO | WO-2005/067500 A2 | 7/2005 |
| WO | WO 2005/076783 | 8/2005 |
| WO | WO 2005/079195 | 9/2005 |
| WO | WO 2005/094531 | 10/2005 |
| WO | WO-2005/110013 A2 | 11/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/063072 A2 | 6/2006 |
| WO | WO-2006/063152 A2 | 6/2006 |
| WO | WO 2006/065280 | 6/2006 |
| WO | WO-2006/073940 A2 | 7/2006 |
| WO | WO 2006/074003 | 7/2006 |
| WO | WO-2006/074045 A2 | 7/2006 |
| WO | WO 2006/004737 | 8/2006 |
| WO | WO 2006/083400 | 8/2006 |
| WO | WO 2006/083440 | 8/2006 |
| WO | WO-2006/084251 A2 | 8/2006 |
| WO | WO 2006/086449 | 8/2006 |
| WO | WO 2006/086633 | 8/2006 |
| WO | WO-2006/086634 A2 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO-2006/093514 A2 | 9/2006 |
| WO | WO 2006/098852 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Bachman et al., "Synthesis of Substituted Quinolylamines. Derivatives of 4-Amino-7-Chloroquinoline.", *J. Org. Chem*, 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).
Baranov et al., "Pyrazoles, Imidazoles, and Other 5-Membered Rings.", *Chem. Abs.* 85, 94362, (1976).
Berényi et al., "Ring Transformation of Condensed Dihydro-astriazines.", *J. Heterocyclic Chem.*, 18, pp. 1537-1540 (1981).
Chollet et al., "Development of a Topically Active Imiquimod Formulation.", *Pharmaceutical Development and Technology*, 4(1), pp. 35-43 (1999).
Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).
Wermuth et al., "Molecular Variations Based on Isosteric Replacements." The Practice of Medicinal Chemistry, pp. 203-237 (1996).
Invitation to Pay Additional Fees for PCT/US2004/043447 mailed Jun. 20, 2005.
International Search Report and Written Opinion for PCT/US2004/043447 mailed Aug. 24, 2005.
International Preliminary Report on Patentability for PCT/US2004/043447 mailed Jul. 13, 2006.
[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.
[No Author Listed] Encyclopedia of Pharmaceutical Technology. 2nd Ed. Marcel Dekker, Inc. 2002:856-60.
Agrawal et al., Synthetic agonists of Toll-like receptors 7, 8 and 9. Biochem Soc Trans. Dec. 2007;35(Pt 6):1461-7.
Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.
Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-80.
Alexopoulou et al., Recognition of double-stranded RNA and activation of NF-kappaB by Toll-like receptor 3. Nature. Oct. 18, 2001;413(6857):732-8.
Assuma et al., IL-1 and TNF Antagonists Inhibit the Inflammatory Response and Bone Loss in Experimental Periodontitis. J Immunol. 2000;160:403-09.
Au et al., Virus-mediated induction of interferon A gene requires cooperation between multiple binding factors in the interferon alpha promoter region. J Biol Chem. Nov. 15, 1993;268(32):24032-40.
Auerbach et al., Erythema nodosum following a jellyfish sting. J Emerg Med. Nov.-Dec. 1987;5(6):487-91.
Auwers, [Uber die Isomerie-Verhaltnisse in der Pyrazol-Reihe. Berichte. VI.] 1926;601-607. German.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with *Porphyromonas gingivalis* and induced alveolar bone loss in immunocompetent and severe combined immunodeficient mice. Arch Oral Biol. Dec. 1994;39(12):1035-40.
Baldwin et al., Amino Acid Synthesis via Ring Opening of N-Sulphonyl Aziridine-2-Carboxylate Esters with Organometallic Reagents. Tetrahedron. 1993;49:6309-30.
Bártová et al., Th1 and Th2 cytokine profile in patients with early onset periodontitis and their healthy siblings. Mediators Inflamm. 2000;9(2):115-20.
Beck et al., Dental Infections and Atherosclerosis. Am Heart J. 1999;13:528-33.
Beckett et al., Configurational Studies in Synthetic Analgesics: the Synthesis of (−)-Methadone from D-(−)-Alanine. J Chem Soc. 1957;1:858-61.
Beilman et al., Experimental brown spider bite in the guinea pig: Results of treatment with dapsone or hyperbaric oxygen. J Wilderness Medicine. 1994;5:287-94.

(56) References Cited

OTHER PUBLICATIONS

Belikov, Abbreviated Guide to Synthetic and Natural Medications. Pharmaceutical Chemistry. Higher School. 1993;1:43-47. Russian.

Beltrami et al., Some Methylhydrazonium Salts; An Improved Synthesis of Tetramethylhydrazine. J Am Chem Soc. 1956;78:2467-68.

Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.

Bertino et al., Principles of Cancer Therapy. Cecil Textbook of Medicine. Goldman et al., eds. 21th Ed. W.B. Saunders Company. 2000:1:1060-74.

Beutler et al., Tumor necrosis factor in the pathogenesis of infectious diseases. Crit Care Med. Oct. 1993;21(10 Suppl):S423-35.

Beutner et al., Therapeutic response of basal cell carcinoma to the immune response modifier imiquimod 5% cream. J Am Acad Dermatol. Dec. 1999;41(6):1002-7.

Beutner et al., Treatment of genital warts with an immune-response modifier (imiquimod). J Am Acad Dermatol. Feb. 1998;38(2 Pt 1):230-9.

Binder, Acute arthropod envenomation. Incidence, clinical features and management. Med Toxicol Adverse Drug Exp. May-Jun. 1989;4(3):163-73.

Bishop et al., Molecular mechanisms of B lymphocyte activation by the immune response modifier R-848. J Immunol. Nov. 15, 2000;165(10):5552-7.

Bitterman-Deutsch et al., [Brown spider bite]. Harefuah. Sep. 1990;119(5-6):137-9. Hebrew.

Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1):S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3+2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Douglas, Introduction to Viral Diseases. In: Cecil Textbook of Medicine. Bennet et al., eds. 20th Ed. W.B. Saunders Company. 1996:2:1739-47.

(56) References Cited

OTHER PUBLICATIONS

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract p. 81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999;21(9). 3 pages.

Gendron, *Loxosceles ignali* Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-*Loxosceles* Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-69. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for *Loxosceles* envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Jacobs, Chapter 1. The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jurk et al. Human TLR7 and TLR8 independently confer responsiveness to the antiviral compound R-848. Nat Immunol. Jun. 2002;3(6):499.

(56) References Cited

OTHER PUBLICATIONS

Juweid, Radioimmunotherapy of B-Cell Non-Hodgkin's Lymphoma: From Clinical Trials to Clinical Practice. J Nuclear Med. 2002;43(11):1507-29.
Katritsky et al., Comprehensive Heterocyclic Chemistry: The Structure, Reactions, Synthesis and Uses of Heterocyclic Compounds. 1984;2:586-587.
Keating et al., Long-term follow-up of patients with chronic lymphocytic leukemia treated with fludarabine as a single agent. Blood. Jun. 1, 1993;81(11):2878-84.
Klausen et al., Two complementary methods of assessing periodontal bone level in rats. Scand J Dent Res. Dec. 1989;97(6):494-9.
Klinman, Immunotherapeutic uses of CpG oligodeoxynucleotides. Nat Rev Immunol. Apr. 2004;4(4):249-58.
Kloek et al., An improved method for the synthesis of stabilized primary enamines and imines. J Org Chem. 1978;43:1460-62.
Kloetzel, Reactions of nitroparaffins. I. Synthesis and reduction of some ò-nitrokenes. J Am Chem Soc. 1947;69:2271-2275.
Kornman, Host modulation as a therapeutic strategy in the treatment of periodontal disease. Clin Infect Dis. Mar. 1999;28(3):520-6.
Kourafalos et al., Synthesis of 7-aminopyrazolo[3,4-c]pyridine as a probe for the preparation of compounds of pharmacological interest. Heterocycles. 2002;57(12):2335-2343.
Krause et al., Autoimmune aspects of cytokine and anticytokine therapies. Am J Med. Oct. 1, 2003;115(5):390-7.
Krenitsky et al., Imidazo[4,5-c]pyridines (3-deazapurines) and their nucleosides as immunosuppressive and anti-inflammatory agents. J Med Chem. Jan. 1986;29(1):138-43.
Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.
Lall et al., Serine and threonine beta-lactones: a new class of hepatitis A virus 3C cysteine proteinase inhibitors. J Org Chem. Mar. 8, 2002;67(5):1536-47.
Lee et al., p38 mitogen-activated protein kinase inhibitors—mechanisms and therapeutic potentials. Pharmacol Ther. 1999;82:389-97.
Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.
Lehner et al., The role of γδ cells and β-chemokines in mucosal protection against SIV infection. Immunology Lett. 1999;69:25-192. Abstract 2.1.
Levy et al., Unique efficacy of Toll-like receptor 8 agonists in activating human neonatal antigen-presenting cells. Blood. Aug. 15, 2006;108(4):1284-90. Epub Apr. 25, 2006.
Leynadier et al., Allergic reactions to North African scorpion venom evaluated by skin test and specific IgE. J Allergy Clin Immunol. Jun. 1997;99(6 Pt 1):851-3. 4 pages.
Li et al., An improved protocol for the preparation of 3-pyridyl- and some arylboronic acids. J Org Chem. Jul. 26, 2002;67(15):5394-7.
Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.
Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.
Litt et al., Mucosal delivery of vaccine antigens displayed on the surface of *Lactococcus lactis*. Immunology Lett. 1999;69(1):61. Abstract #11.26.
Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.
Loesche et al., Treatment paradigms in periodontal disease. Compend Contin Educ Dent. Mar. 1997;18(3):221-6, 228-30, 232 passim; quiz 234. Review.
Luger et al., Evidence for an epidermal cytokine network. J Invest Dermatol. Dec. 1990;95(6 Suppl):100S-104S.
Luskin et al., Olefinic Derivatives of 2,4-Diamino-s-triazines. J Org Chem. 1958;23:1032-37.
Macchia et al., Synthesis and antiviral properties of 9-[(2-methyleneaminoxyethoxy)methyl]guanine derivatives as novel Acyclovir analogues. Farmaco. Feb. 2000;55(2):104-8.
Majeski et al., Action of venom from the brown recluse spider (*Loxosceles reclusa*) on human neutrophils. Toxicon. 1977;15(5):423-7.
Makarenkova et al., Identification of delta- and mu-type opioid receptors on human and murine dendritic cells. J Neuroimmunol. 2001;117:68-77.
Male et al., Introduction to the Immune System. In: Immunology. Elsevier. 2006:6-7.
Masihi, Progress on novel immunomodulatory agents for HIV-1 infection and other infectious diseases. Expert Opin Ther Patents. 2003;13(6):867-82.
Masiukiewicz et al., Scalable Syntheses of N$^\alpha$-Benzyloxycarbonyl-L-Ornithine and of N$^\alpha$-(9-Fluorenylmethoxy)Carbonyl-L-Ornithine. Org Prep Proced Int. 2002;34:531-37.
Mataka et al., Condensation reaction of 3,4-Dibenzoyl-1-methyl-2,5-diphenylpyrrole and-1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.
Mathur et al., Cell-mediated immune system regulation in periodontal diseases. Crit Rev Oral Biol Med. 1997;8(1):76-89.
Maynor et al., Brown recluse spider envenomation: a prospective trial of hyperbaric oxygen therapy. Acad Emerg Med. Mar. 1997;4(3):184-92.
Mbow et al., Small molecule and biologic modulators of the immune response to hepatitis C virus. Mini Rev Med Chem. May 2006;6(5):527-31.
McCarthy et al., Opioids, opioid receptors, and the immune response. Drug & Alcohol Dependence. 2001;62:111-23.
McKennon et al., A Convenient Reduction of Amino Acids and Their Derivatives. J Org Chem. 1993;58:3568-71.
McLaughlin et al., Opioid growth factor (OGF) inhibits the progression of human squamous cell carcinoma of the head and neck transplanted into nude mice. Cancer Lett. 2003;199:209-17.
Medzhitov, Toll-Like Receptors and Innate Immunity. Nature Rev Immunol. 2001;1:135-45.
Mee et al., Stille coupling made easier—the synergic effect of copper(I) salts and the fluoride ion. Angew Chem. 2004;116:1152-56.
Merigian et al., Envenomation From the Brown Recluse Spider: Review of Mechanism and Treatment Options. Am J Ther. Oct. 1996;3(10):724-734.
Miller et al., Imiquimod applied topically: a novel immune response modifier and new class of drug. Int J Immunopharmacol. Jan. 1999;21(1):1-14.
Minakawa et al., Nucleosides and Nucleotides. 184. Synthesis and Conformational Investigation of Anti-Fixed 3-Deaza-3-halopurine Ribonucleosides. J Org Chem. 1999;64:7158-72.
Moebius et al., The mysteries of sigma receptors: new family members reveal a role in cholesterol synthesis. Trends Pharmacol Sci. Mar. 1997;18(3):67-70.
Moldoveanu et al., Poly-L-lysine as a potential mucosal adjuvant. Immunology Lett. 1999;69(1):62. Abstract #11.28.
Mollick et al., MUC1-like tandem repeat proteins are broadly immunogenic in cancer patients. Cancer Immun. Mar. 17, 2003;3:3. 17 pages.
Moody et al., Lipoxygenase inhibitors prevent lung carcinogenesis and inhibit non-small cell lung cancer growth. Exp Lung Res. Jul.-Aug. 1998;24(4):617-28.
Moraczewski et al., Using Hydrogen Bonding to Control Carbamate C-N Rotamer Equilibria. Org Chem. Oct. 16, 1998;63(21):7258-7262.
Mosbech et al., [Allergy to insect stings] Ugeskr Laeger. Oct. 28, 1991;153(44):3067-71. Danish.
Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

(56) References Cited

OTHER PUBLICATIONS

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-80.

Muzio et al., Differential expression and regulation of toll-like receptors (TLR) in human leukocytes: selective expression of TLR3 in dendritic cells. J Immunol. Jun. 1, 2000;164(11):5998-6004.

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like receptor 7 ligand. J Immunol. Oct. 15, 2003;171(8):3977-82.

Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.

Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-70.

Osol et al., Chapter 27: Structure-Activtiy Relationship and Drug Design. In: Remington's Pharmaceutical Sciences. 16th Ed. Mach Publishing. 1980:420-35.

Ottonello et al., Sulphonamides as anti-inflammatory agents: old drugs for new therapeutic strategies in neutrophilic inflammation? Clin Sci (Lond). Mar. 1995;88(3):331-6.

Ozinsky et al., The repertoire for pattern recognition of pathogens by the innate immune system is defined by cooperation between Toll-like receptors. Proc. Nat. Acad. Sci. 2000; 97(25):13766-71.

Page et al., Advances in the pathogenesis of periodontitis: summary of developments, clinical implications and future directions. Periodontol 2000. Jun. 1997;14:216-48.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Park et al., Sodium Dithionite Reduction of Nitroarenes Using Viologen as an Electron Phase-Transfer Catalyst. Tetrahedron Lett. 1993;34(46):7445-46.

Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.

Patrick et al., Paragraph 10.3: Drug optimization: strategies in drug design. In: An Introduction to Medicinal Chemistry. Oxford: Oxford University Press. Jan. 2005. 200-218.

Pavletic et al., Outcome of allogeneic stem cell transplantation for B cell chronic lymphocytic leukemia. Bone Marrow Transplant. Apr. 2000;25(7):717-22.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.

Payvandi et al., Exogenous and Endogenous IL-10 Regulate IFN-α Production by Peripheral Blood Mononuclear Cells in Response to Viral Stimulation. J Immunol. 1998;160:5861-68.

Peschke et al., Synthesis and in vitro characterization of new growth hormone secretagogues derived from ipamorelin with dipeptidomimetic N-terminals. Eur J Med Chem. 1999;34:363-380.

Peterson et al., The opioid-cytokine connection. J Neuroimmunol. 1998;83:63-69.

Phillips et al., Therapy of brown spider envenomation: a controlled trial of hyperbaric oxygen, dapsone, and cyproheptadine. Ann Emerg Med. Mar. 1995;25(3):363-8.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COX-2 immunoreactivity in the mice bladder and kidney after bacterial instillation. Immunology Lett. 1999;69(1):122. Abstract #31.5.

Powell et al., Compendium of excipients for parenteral formulations. PDA J Pharm Sci Technol. Sep.-Oct. 1998;52(5):238-311.

Prelog et al., Cycloalkeno-pyridine. Helv Chem Acta. 1945;28:1684-93. German.

Rees et al., Brown recluse spider bites. A comparison of early surgical excision versus dapsone and delayed surgical excision. Ann Surg. Nov. 1985;202(5):659-63.

Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.

Rhodes, Discovery of immunopotentiatory drugs: current and future strategies. Clin Exp Immunol. Dec. 2002;130(3):363-9.

Ribera et al., "Spontaneous" complete remissions in chronic lymphocytic leukemia: report of three cases and review of the literature. Blood Cells. 1987;12(2):471-79.

Ritter et al., A new reaction of nitriles; amides from alkenes and mononitriles. J Am Chem Soc. Dec. 1948;70(12):4045-8.

Rocca et al., Carbolines. Part VII. Ansidines, Convenient tools to synthesize fficien-β-carbolines. J Heterocyclic Chem. 1995;32:1171-1175.

Rocca et al., Connection between metalation and cross-coupling strategies. A new convergent route to azacarbazoles. Tetrahedron. 1993;49(1):49-64.

Rollins, Chemokines. Blood. Aug. 1, 1997;90(3):909-28. Review.

Rosenberg et al., Treatment of 283 consecutive patients with metastatic melanoma or renal cell cancer using high-dose bolus interleukin 2. JAMA. Mar. 23-30, 1994;271(12):907-13.

Rothel et al., The use of recombinant ovine IL-1beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

(56) References Cited

OTHER PUBLICATIONS

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymmetry. 1999;10:3417-30.

Severa et al., Sensitization to TLR7 agonist in IFN-beta-preactivated dendritic cells. J Immunol. May 15, 2007;178(10):6208-16.

Seymour et al., Cellular immunity and hypersensitivity as components of periodontal destruction. Oral Dis. Mar. 1996;2(1):96-101. Review.

Shelburne et al., Quantitation of *Bacteroids forsythus* in subgingival plaque comparison on immunoassay and quantitative polymerase chain reaction. J Microbiol Methods. 2000;39:97-107.

Sidky et al., Inhibition of murine tumor growth by an interferon-inducing imidazoquinolinamine. Cancer Res. Jul. 1, 1992;52(13):3528-33.

Siegal et al., The nature of the principal type 1 interferon-producing cells in human blood. Science. Jun. 11, 1999;284(5421):1835-7.

Sletzinger et al., The Synthesis of Isomethadone. J Am Chem Soc. 1952;74:5619-20.

Smith et al., The role of polymorphonuclear leukocytes in the lesion caused by the venom of the brown spider, *Loxosceles reclusa*. Lab Invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et al., Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR-7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. *Latrodectus mactans*. N Engl J Med. Jun. 5, 1997;336(23):1649.

Stanley, Imiquimod and the imidazoquinolones: mechanism of action and therapeutic potential. Clin Exp Dermatol. Oct. 2002;27(7):571-7. Review.

Stashenko et al., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Acad Dermatol. Sep. 2000;43(3):555-6.

Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475. Abstract 3030.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Thesing et al., [Darstellung und Eigenschaften des $\Delta^1$-Pyrrolin-*N*-oxyds.]. Chem Ber. 1959;92:1748-55. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-15.

Tomic et al., Sensitization of IL-2 Signaling through TLR-7 Enhances B Lymphoma Cell Immunogenicity. J Immunol. 2006;176:3830-39.

Totterman et al., Phorbol ester-induced differentiation of chronic lymphocytic leukaemia cells. Nature. Nov. 13, 1980;288(5787):176-8.

Tomioka et al., Asymmetric Alkylation of α-Alkyl β-Keto Esters. J Am Chem Soc. 1984;106:2718-19.

Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.

Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.

Urosevic et al., Imiquimod treatment induces expression of opioid growth factor receptor: a novel tumor antigen induced by interferon-alpha? Clin Cancer Res. Aug. 1, 2004;10(15):4959-70.

Van De Kerhof, New Immunomodulatory Drugs. In: Skin and Environment: Perception and Protection. Ring et al., eds., 10th EADV Congress, Oct. 10-14, Munich, Germany. 2001:1:343-48.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells—the emerging frontier. Urol Clin North Am. Aug. 2003;30(3):633-43.

Vilcek, The cytokines: An overview. In: The Cytokine Handbook, Fourth Ed. M. Lotze and A.W. Thompson (eds.), 2003;1:3-14.

(56) References Cited

OTHER PUBLICATIONS

Volhardt, 18-5. Amides: The Least-Reactive Carboxylic Acid Derivatives. Organic Chemistry. 1987:813.
Vollmer et al., Highly immunostimulatory CpG-free oligodeoxynucleotides for activation of human leukocytes. Antisense Nucleic Acid Drug Dev. Jun. 2002;12(3):165-75.
Wagner et al., Induction of cytokines in cynomolgus monkeys by the immune response modifiers, imiquimod, S-27609 and S-28463. Cytokine. Nov. 1997;9(11):837-45.
Wagner et al., Modulation of TH1 and TH2 Cytokine Production with the Immune Response Modifiers, R-848 and Imiguimod. Cellular Immunology. 1999;191:10-19.
Wang, Structure and Chemistry of 4-Hydroxy-6-methyl-2-pyridone. J Heterocyclic Chem. 1970;7:389-92.
Warren et al., Macrophage Growth Factor CSF-1 Stimulates Human Monocyte Production of Interferon, Tumor Necrosis Factor, and Colony Stimulating Activity. J Immunol. 1986;137(7):2281-85.
Wasserman et al., Loxoscelism and necrotic arachnidism. J Toxicol Clin Toxicol. 1983-1984;21(4-5):451-72.
Wedlock et al., Physiological effects and adjuvanticity of recombinant brushtail possum TNF-alpha. Immunol Cell Biol. Feb. 1999;77(1):28-33.
Wells, Additivity of Mutational Effects in Proteins. Biochemistry. 1990;29(37):8509-17.
Wexler et al., Accurate identification of experimental pulmonary metastases. J Natl Cancer Inst. Apr. 1966;36(4):641-5.
Wibaut et al., Syntheses of 3,4-Dimethylpyridine, 2,3-Dimethylpridine and 2-Methyl-3-Ethylpyridine. Rec Trav Chim. 1944;63:231-38.
Wierda et al., CD40-ligand (CD154) gene therapy for chronic lymphocytic leukemia. Blood. Nov. 1, 2000;96(9):2917-24.
Wieseler-Frank et al., Central proinflammatory cytokines and pain enhancement. Neurosignals. 2005;14(4):166-74.
Williams et al., Grignard Reactions to Chiral Oxazolidine Aldehydes. Tetrahedron. 1996;52:11673-94.
Wilson et al., Spiders and spider bites. Dermatol Clin. Apr. 1990;8(2):277-86.
Wright et al., Clinical presentation and outcome of brown recluse spider bite. Ann Emerg Med. Jul. 1997;30(1):28-32.
Wu et al., Murine B16 melanoma vaccination-induced tumor immunity: identification of specific immune cells and functions involved. J Interferon Cytokine Res. Dec. 2001;21(12):1117-27.
Yamamoto et al., Essential role for TIRAP in activation of the signalling cascade shared by TLR2 and TLR4. Nature. Nov. 21, 2002;420(6913):324-9.
Yeung-Yue et al., The management of herpes simplex virus infections. Curr Opin Infect Dis. Apr. 2002;15(2):115-22.
Yutilov et al., Synthesis and some reactions of 4-nitroimidazo[4-5-c]pyridin-2-ones. CAPLUS English Abstract DN 91:175261. VINITI.1978:1193-78. Abstract Only.
Zagon et al., Immunoelectron microscopic localization of the opioid growth factor receptor (OGFr) and OGF in the cornea. Brain Res. 2003;967:37-47.
Zagon et al., Opioids and the apoptotic pathway in human cancer cells. Neuropeptides. 2003;37:79-88.
Zagon et al., The biology of the opioid growth factor receptor (OGFr). Brain Res Rev. Feb. 2002;38(3):351-76. Review.
Zagon et al., The expression and function of the OGF-OGFr axis—a tonically active negative regulator of growth—in COS cells. Neuropeptides. Oct. 2003;37(5):290-7.
Zambon, Periodontal diseases: microbial factors. Ann Periodontol. Nov. 1996;1(1):879-925.
Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.
Zhang et al., Structural features of azidopyridinyl neonicotinoid probes conferring high affinity and selectivity for mammalian alpha4beta2 and *Drosophila* nicotinic receptors. J Med Chem. Jun. 20, 2002;45(13):2832-40.
Zhu et al., Inhibition of murine dendritic cell activation by synthetic phosphorothioate oligodeoxynucleotides. J Leukoc Biol. Dec. 2002;72(6):1154-63.
Zhu et al., Inhibition of murine macrophage nitric oxide production by synthetic oligonucleotides. J Leukoc Biol. Apr. 2002;71(4):686-94.
Ziegler-Heitbrock et al., Favorable response of early stage B CLL patients to treatment with IFN-alpha 2. Blood. May 1, 1989;73(6):1426-30.
Zyryanov et al., Heterocyclization of 1-(2'-Carbethoxyphenyl)-5-Methyltetrazole. Chemistry of Heterocylic Compounds. English Edition. 1981;16(12):1286-88.

* cited by examiner

IMIDAZOQUINOLINYL SULFONAMIDES

RELATED APPLICATIONS

This application is the National Stage of International Application No. PCT/US2004/043447, filed Dec. 23, 2004, which claims priority to U.S. Provisional Application Ser. No. 60/533,465, filed Dec. 30, 2003; U.S. Provisional Application Ser. No. 60/555,936, filed Mar. 24, 2004; and U.S. Provisional Application Ser. No. 60/581,335, filed Jun. 18, 2004, all of which are incorporated herein by reference.

FIELD OF THE INVENTION

This invention relates to derivatives of imidazoquinoline, imidazopyridine, and imidazonaphthyridine compounds and to pharmaceutical compositions containing the compounds. A further aspect of this invention relates to the use of these compounds as immunomodulators, for inducing cytokine biosynthesis in animals and in the treatment of diseases including viral and neoplastic diseases.

BACKGROUND OF THE INVENTION

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula I:

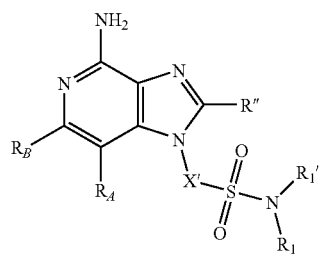

(I)

and more specifically, compounds of the following Formulas Ia, Ib, II, IIa, III, IV, V, VI, VII, VIII, IX, X, and XI:

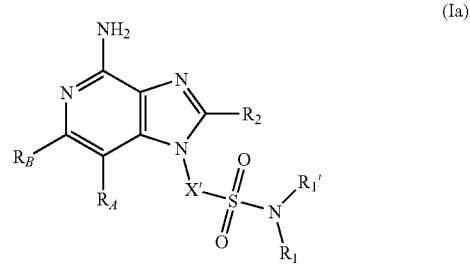

(Ia)

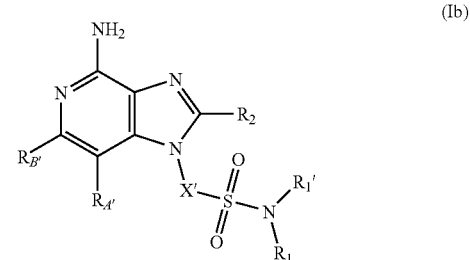

(Ib)

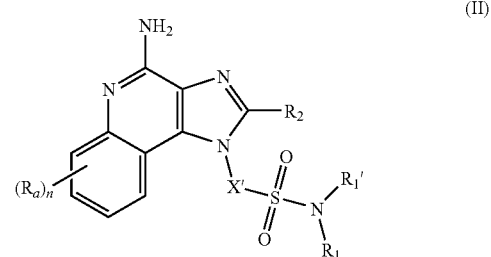

(II)

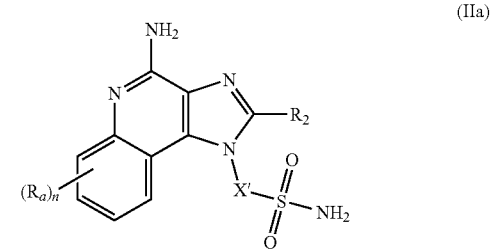

(IIa)

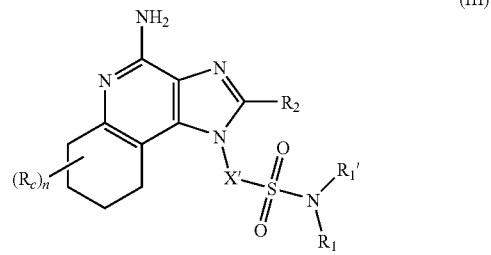

(III)

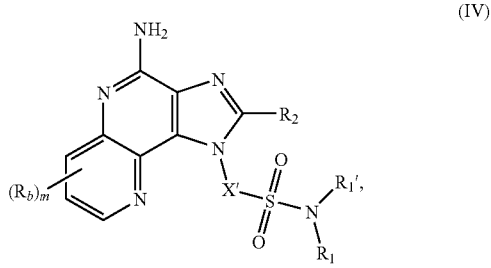

(IV)

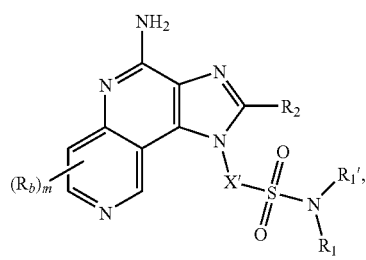
(V)

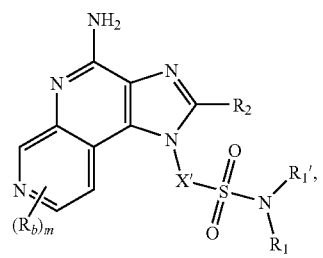
(VI)

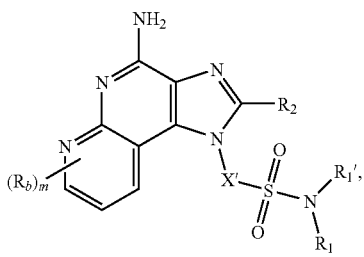
(VII)

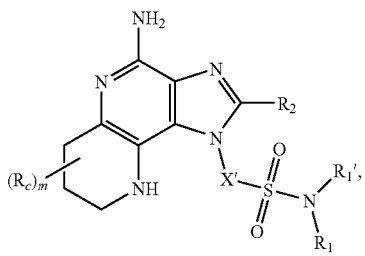
(VIII)

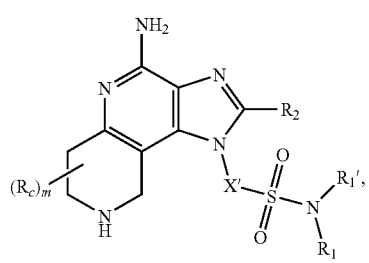
(IX)

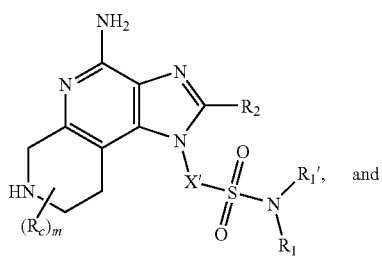
(X)

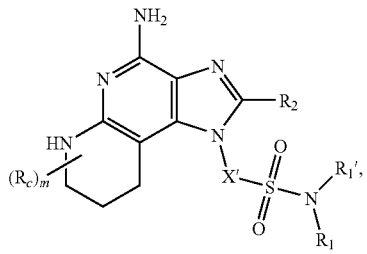
(XI)

wherein: $R_1$, R", $R_2$, $R_1'$, $R_A$, $R_B$, $R_{A'}$, $R_{B'}$, $R_a$, $R_b$, $R_c$, X', n, and m are as defined below; and pharmaceutically acceptable salts thereof.

The compounds of Formulas I, Ia, Ib, II, IIa, III, IV, V, VI, VII, VIII, IX, X, and XI are useful, for example, as immune response modifiers (IRMs) due to their ability to modulate cytokine biosynthesis (e.g., induce the biosynthesis or production of one or more cytokines) and otherwise modulate the immune response when administered to animals. Compounds can be tested, for example, using the test procedure described in the Examples Section. Compounds can be tested for induction of cytokine biosynthesis by incubating human PBMC in a culture with the compound(s) at a concentration range of 30 to 0.014 μM and analyzing for interferon (α) or tumor necrosis factor (α) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

In another aspect, the present invention provides pharmaceutical compositions containing the immune response modifier compounds, and methods of inducing cytokine biosynthesis in an animal, treating a viral disease in an animal, and treating a neoplastic disease in an animal by administering an effective amount of one or more compounds of Formulas I, Ia, Ib, IIa, III, IV, V, VI, VII, VIII, IX, X, and XI and/or pharmaceutically acceptable salts thereof to the animal.

In another aspect, the invention provides methods of synthesizing compounds of the Formulas I, Ia, Ib, II, IIa, III, IV, V, VI, VII, VIII, IX, X, and XI and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION
The present invention provides compounds of the following Formula I:
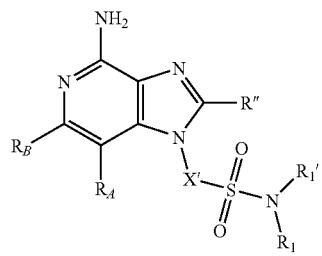
(I)
and more specifically, compounds of the following Formulas Ia, Ib, II, IIa, III, IV, V, VI, VII, VIII, IX, X, and XI:
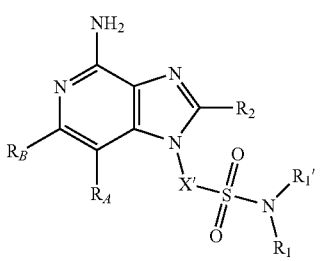
(Ia)
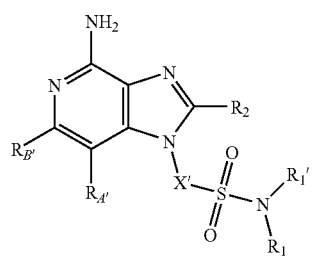
(Ib)
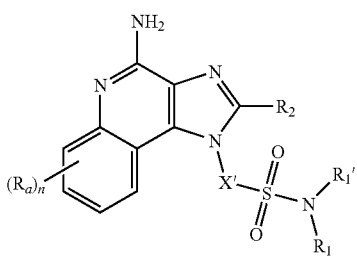
(II)
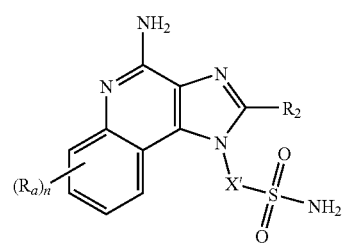
(IIa)
-continued
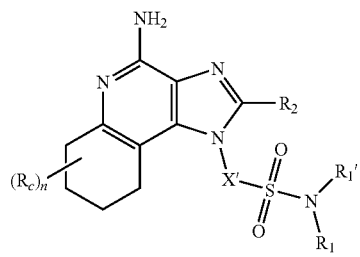
(III)
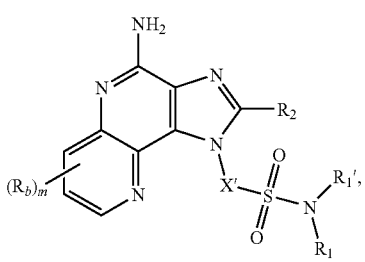
(IV)
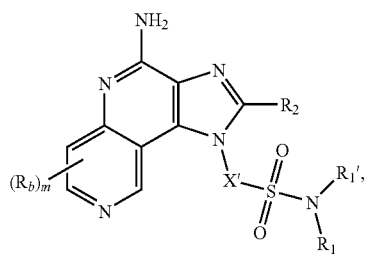
(V)
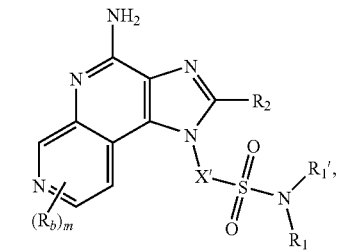
(VI)
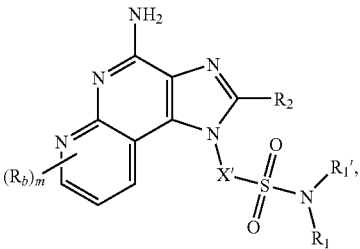
(VII)
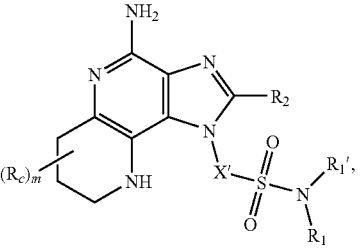
(VIII)

-continued

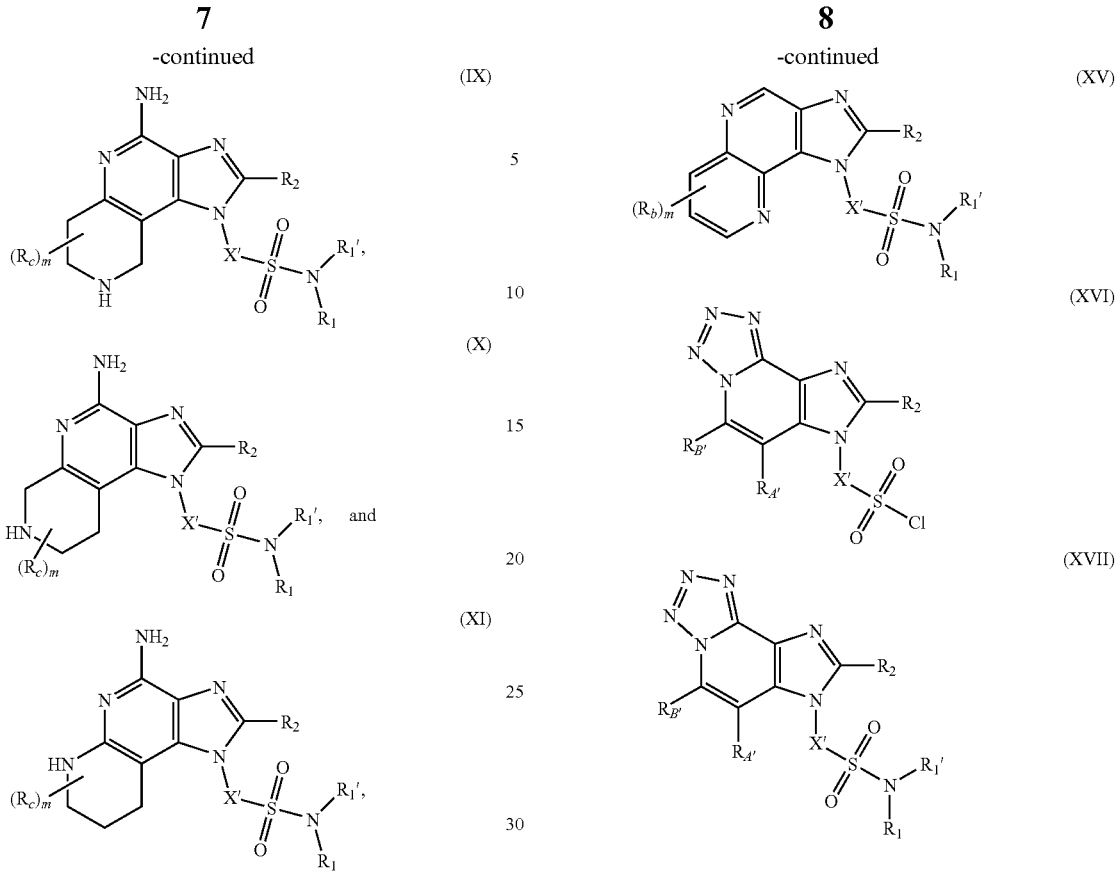

as well as intermediates of the following formulas XII, XIII, XIV, XV, XVI, and XVII:

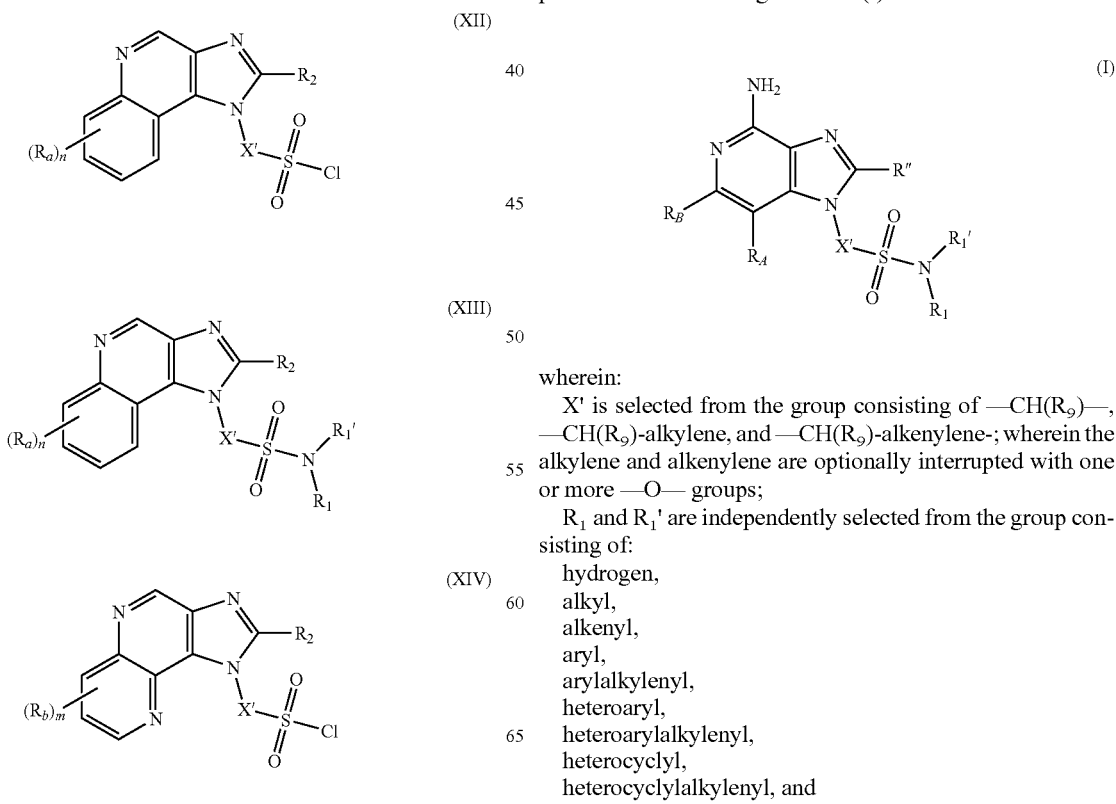

wherein: $R_1$, R", $R_2$, $R_1'$, $R_A$, $R_B$, $R_{A'}$, $R_{B'}$, $R_a$, $R_b$, $R_c$, X', n, and m are as defined below; and pharmaceutically acceptable salts thereof.

In one embodiment, the present invention provides compounds of the following Formula (I):

wherein:
X' is selected from the group consisting of —CH($R_9$)—, —CH($R_9$)-alkylene, and —CH($R_9$)-alkenylene-; wherein the alkylene and alkenylene are optionally interrupted with one or more —O— groups;
$R_1$ and $R_1'$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
arylsulfonyl,
alkylsulfonyl, and
—N(R$_9$)$_2$,
or R$_1$ and R$_1$' can join together to form a ring of the formula:

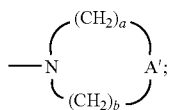

A' is selected from the group consisting of —O—, —C(O)—, —CH$_2$—, —S(O)$_{0-2}$—, —N(R$_4$)—, and —N(Q-R$_4$)—;
a and b are independently integers from 1 to 6 with the proviso that a+b is ≤7,
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
W is selected from the group consisting of a bond, —C(O)—, and —S(O)$_2$—;
R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;
R$_6$ is selected from the group consisting of =O and =S;
R$_8$ is selected from the group consisting of hydrogen, alkyl, alkoxyalkylenyl, and arylalkylenyl;
R$_9$ is selected from the group consisting of hydrogen and alkyl;
R" is hydrogen or a non-interfering substituent;
R$_A$ and R$_B$ are independently selected from the group consisting of:
hydrogen,
halogen,
alkyl,
alkenyl,
alkoxy,
alkylthio, and
—N(R$_9$)$_2$;
or R$_A$ and R$_B$ taken together form either a fused aryl ring that is unsubstituted or substituted by one or more R$_a$ groups, or a fused 5 to 7 membered saturated ring that is unsubstituted or substituted by one or more R$_c$ groups;
or R$_A$ and R$_B$ taken together form a fused heteroaryl or 5 to 7 membered saturated ring, containing one heteroatom selected from the group consisting of N and S, wherein the heteroaryl ring is unsubstituted or substituted by one or more R$_b$ groups, and the 5 to 7 membered saturated ring is unsubstituted or substituted by one or more R$_c$ groups;
R$_a$ is selected from the group consisting of:
fluoro,
alkyl,
haloalkyl,
alkoxy, and
—N(R$_9$)$_2$;
R$_b$ is selected from the group consisting of:
halogen,
hydroxy,
alkyl,
alkenyl,
haloalkyl,
alkoxy, and
—N(R$_9$)$_2$; and
R$_c$ is selected from the group consisting of:
halogen,
hydroxy,
alkyl,
alkenyl,
haloalkyl,
alkoxy,
alkylthio, and
—N(R$_9$)$_2$;
or a pharmaceutically acceptable salt thereof.

In one embodiment, the present invention also provides compounds of the following Formula (Ia):

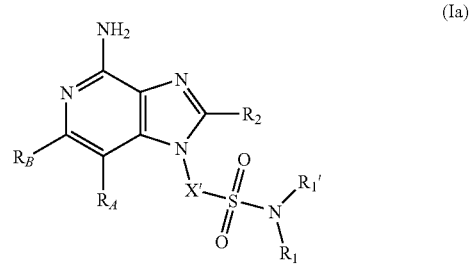

(Ia)

wherein:
X' is selected from the group consisting of —CH(R$_9$)—, —CH(R$_9$)-alkylene, and —CH(R$_9$)-alkenylene-; wherein the alkylene and alkenylene are optionally interrupted with one or more —O— groups;
R$_1$ and R$_1$' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
arylsulfonyl,
alkylsulfonyl, and
—N($R_9$)$_2$,
or $R_1$ and $R_1'$ can join together to form a ring of the formula:

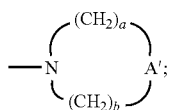

$R_2$ is selected from the group consisting of:
—$R_4$,
—X—$R_4$,
—X—Y—$R_4$, and
—X—$R_5$;
X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

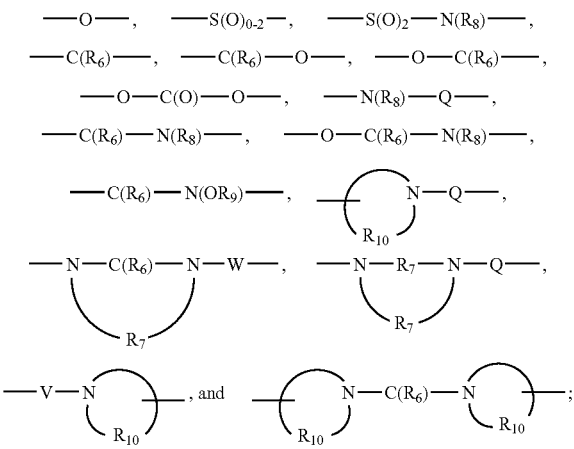

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;
$R_5$ is selected from the group consisting of:

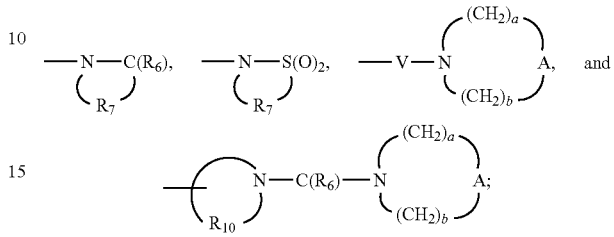

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —CH$_2$—, —S(O)$_{0-2}$—, and —N($R_4$)—;
A' is selected from the group consisting of —O—, —C(O)—, —CH$_2$—, —S(O)$_{0-2}$—, —N($R_4$)—, and —N(Q-$R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—;
a and b are independently integers from 1 to 6 with the proviso that a+b is ≤7;
$R_A$ and $R_B$ are independently selected from the group consisting of:
hydrogen,
halogen,
alkyl,
alkenyl,
alkoxy,
alkylthio, and
—N($R_9$)$_2$;
or $R_A$ and $R_B$ taken together form either a fused aryl ring that is unsubstituted or substituted by one or more $R_a$ groups, or a fused 5 to 7 membered saturated ring that is unsubstituted or substituted by one or more $R_c$ groups;
or $R_A$ and $R_B$ taken together form a fused heteroaryl or 5 to 7 membered saturated ring, containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups;
$R_a$ is selected from the group consisting of:
fluoro,
alkyl,
haloalkyl,
alkoxy, and
—N($R_9$)$_2$;

$R_b$ is selected from the group consisting of:
halogen,
hydroxy,
alkyl,
alkenyl,
haloalkyl,
alkoxy, and
—N($R_9$)$_2$; and $R_c$ is selected from the group consisting of:
halogen,
hydroxy,
alkyl,
alkenyl,
haloalkyl,
alkoxy,
alkylthio, and
—N($R_9$)$_2$;

or a pharmaceutically acceptable salt thereof.

In one embodiment, the present invention also provides compounds of the following Formula (Ib):

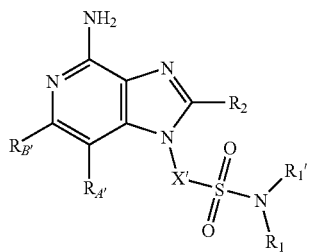

(Ib)

wherein:

X' is selected from the group consisting of —CH($R_9$)—, —CH($R_9$)-alkylene, and —CH($R_9$)-alkenylene-; wherein the alkylene and alkenylene are optionally interrupted with one or more —O— groups;

$R_1$ and $R_1'$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
  hydroxy,
  alkyl,
  haloalkyl,
  hydroxyalkyl,
  alkoxy,
  haloalkoxy,
  halogen,
  cyano,
  nitro,
  arylsulfonyl,
  alkylsulfonyl, and
  —N($R_9$)$_2$, or $R_1$ and $R_1'$ can join together to form a ring of the formula:

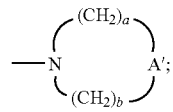

$R_2$ is selected from the group consisting of:
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

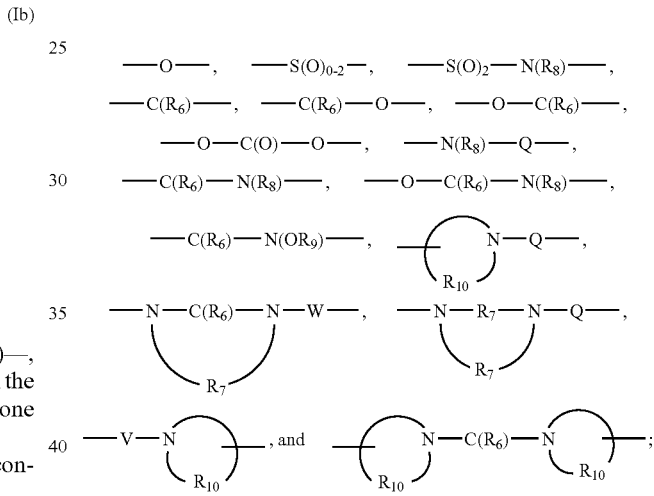

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

$R_5$ is selected from the group consisting of:

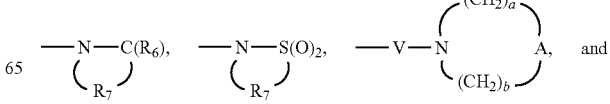

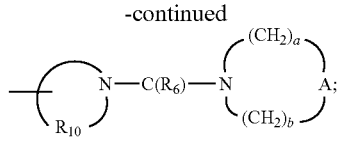

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —CH$_2$—, —S(O)$_{0-2}$—, and —N(R$_4$)—;
A' is selected from the group consisting of —O—, —C(O)—, —CH$_2$—, —S(O)$_{0-2}$—, —N(R$_4$)—, and —N(Q-R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—;
a and b are independently integers from 1 to 6 with the proviso that a+b is ≤7; and
$R_{A'}$ and $R_{B'}$ are independently selected from the group consisting of:
hydrogen,
halogen,
alkyl,
alkenyl,
alkoxy,
alkylthio, and
—N(R$_9$)$_2$;
or a pharmaceutically acceptable salt thereof.

In one embodiment, the present invention also provides compounds of the following Formula II:

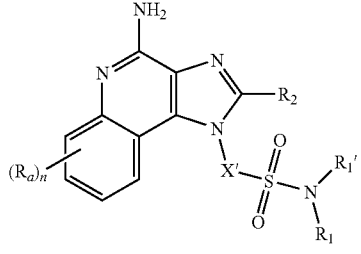

(II)

wherein:
X' is selected from the group consisting of —CH(R$_9$)—, —CH(R$_9$)-alkylene, and —CH(R$_9$)-alkenylene-; wherein the alkylene and alkenylene are optionally interrupted with one or more —O— groups;
$R_1$ and $R_1$' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
arylsulfonyl,
alkylsulfonyl, and
—N(R$_9$)$_2$,
or $R_1$ and $R_1$' can join together to form a ring of the formula:

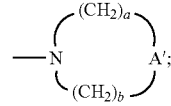

$R_2$ is selected from the group consisting of:
—R$_4$,
—X—R$_4$,
—X—Y—R$_4$, and
—X—R$_5$;
X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

—O—, —S(O)$_{0-2}$—, —S(O)$_2$—N(R$_8$)—,
—C(R$_6$)—, —C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,
—C(R$_6$)—N(OR$_9$)—, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

$R_5$ is selected from the group consisting of:

$$-N(R_7)-C(R_6)-, \quad -N(R_7)-S(O)_2-, \quad -V-N\begin{pmatrix}(CH_2)_a \\ (CH_2)_b\end{pmatrix}A, \text{ and}$$

$$-(R_{10})-N-C(R_6)-N\begin{pmatrix}(CH_2)_a \\ (CH_2)_b\end{pmatrix}A;$$

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —CH$_2$—, —S(O)$_{0-2}$—, and —N(R$_4$)—;
A' is selected from the group consisting of —O—, —C(O)—, —CH$_2$—, —S(O)$_{0-2}$—, —N(R$_4$)—, and —N(Q-R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—;
a and b are independently integers from 1 to 6 with the proviso that a+b is ≤7;
$R_a$ is selected from the group consisting of fluoro, alkyl, haloalkyl, alkoxy, and —N(R$_9$)$_2$; and
n is 0 to 4;
or a pharmaceutically acceptable salt thereof.

In one embodiment, the present invention also provides compounds of the following Formula IIa:

(IIa)

wherein:
X' is selected from the group consisting of —CH(R$_9$)—, —CH(R$_9$)-alkylene, and —CH(R$_9$)-alkenylene-; wherein the alkylene and alkenylene are optionally interrupted with one or more —O— groups;

$R_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—O—, —S(O)$_{0-2}$—, —S(O)$_2$—N(R$_8$)—,
—C(R$_6$)—, —C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,
—C(R$_6$)—N(OR$_9$)—, $$-\begin{pmatrix}N-Q-\\R_{10}\end{pmatrix}-,$$

—N(R$_6$)—C(R$_6$)—N—W—, —N—R$_7$—N—Q—,

—V—N(R$_{10}$)—, and —N(R$_{10}$)—C(R$_6$)—N(R$_{10}$)—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

$R_5$ is selected from the group consisting of:

$$-N(R_7)-C(R_6)-, \quad -N(R_7)-S(O)_2-, \quad -V-N\begin{pmatrix}(CH_2)_a \\ (CH_2)_b\end{pmatrix}A, \text{ and}$$

$$-(R_{10})-N-C(R_6)-N\begin{pmatrix}(CH_2)_a \\ (CH_2)_b\end{pmatrix}A;$$

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;

$R_{10}$ is $C_{3-8}$ alkylene;

A is selected from the group consisting of —O—, —C(O)—, —CH$_2$—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≤7;

$R_a$ is selected from the group consisting of fluoro, alkyl, haloalkyl, alkoxy, and —N(R$_9$)$_2$; and n is 0 to 4;

or a pharmaceutically acceptable salt thereof.

In one embodiment, the present invention also provides compounds of the following Formula III:

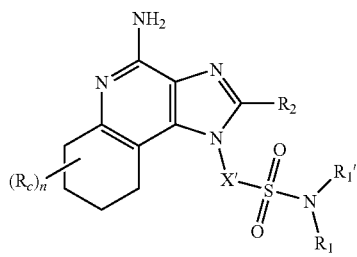

(III)

wherein:

X' is selected from the group consisting of —CH(R$_9$)—, —CH(R$_9$)-alkylene, and —CH(R$_9$)-alkenylene-; wherein the alkylene and alkenylene are optionally interrupted with one or more —O— groups;

R$_1$ and R$_1$' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
arylsulfonyl,
alkylsulfonyl, and
—N(R$_9$)$_2$, or R$_1$ and R$_1$' can join together to form a ring of the formula:

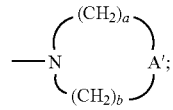

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

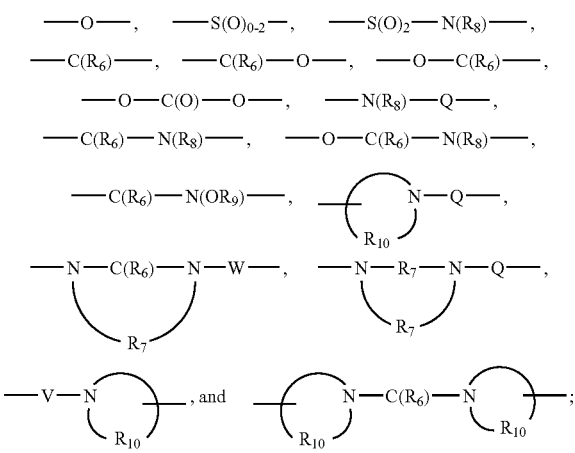

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

R$_5$ is selected from the group consisting of:

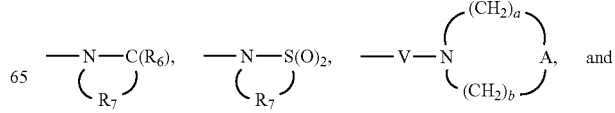

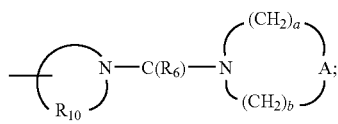

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —CH$_2$—, —S(O)$_{0-2}$—, and —N(R$_4$)—;

A' is selected from the group consisting of —O—, —C(O)—, —CH$_2$—, —S(O)$_{0-2}$—, —N(R$_4$)—, and —N(Q-R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≤7;

$R_c$ is selected from the group consisting of halogen, hydroxy, alkyl, alkenyl, haloalkyl, alkoxy, alkylthio, and —N(R$_9$)$_2$; and n is 0 to 4;

or a pharmaceutically acceptable salt thereof.

In other embodiments, the present invention also provides compounds of the following Formulas IV, V, VI, and VII:

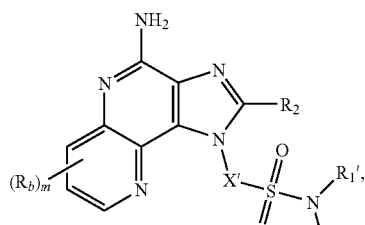

IV

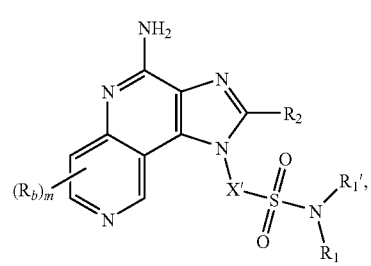

V

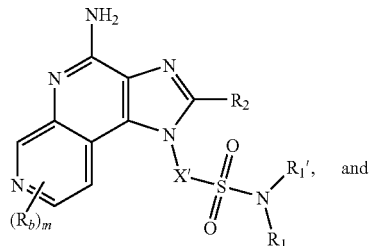

VI

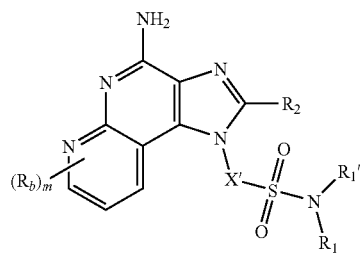

VII wherein:

X' is selected from the group consisting of —CH(R$_9$)—, —CH(R$_9$)-alkylene, and —CH(R$_9$)-alkenylene-; wherein the alkylene and alkenylene are optionally interrupted with one or more —O— groups;

$R_1$ and $R_1'$ are independently selected from the group consisting of:
 hydrogen,
 alkyl,
 alkenyl,
 aryl,
 arylalkylenyl,
 heteroaryl,
 heteroarylalkylenyl,
 heterocyclyl,
 heterocyclylalkylenyl, and
 alkyl, alkenyl, aryl, arylalkylenyl, heteroaryl, heteroarylalkylenyl, heterocyclyl, or heterocyclylalkylenyl, substituted by one or more substituents selected from the group consisting of:
  hydroxy,
  alkyl,
  haloalkyl,
  hydroxyalkyl,
  alkoxy,
  haloalkoxy,
  halogen,
  cyano,
  nitro,
  arylsulfonyl,
  alkylsulfonyl, and
  —N(R$_9$)$_2$,
or $R_1$ and $R_1'$ can join together to form a ring of the formula:

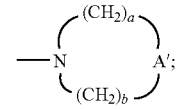

$R_2$ is selected from the group consisting of:
 —R$_4$,
 —X—R$_4$,

—X—Y—R$_4$, and
—X—R$_5$;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

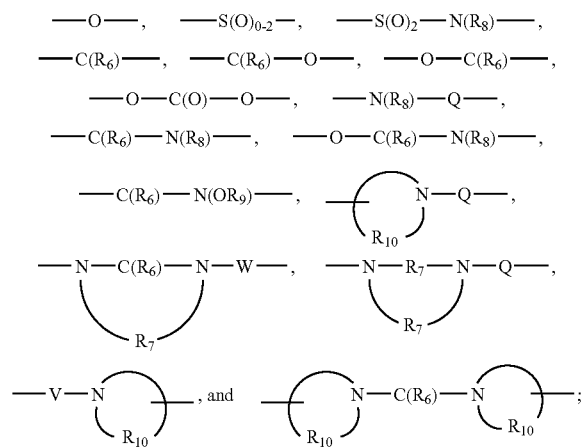

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkyl, and heterocyclyl, oxo;

R$_5$ is selected from the group consisting of:

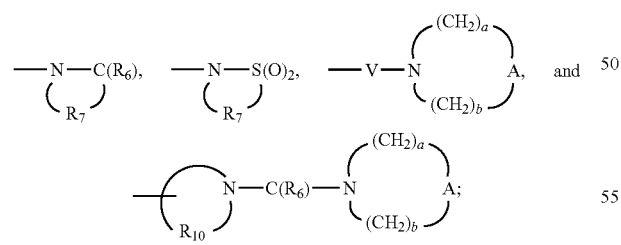

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —CH$_2$—, —S(O)$_{0-2}$—, and —N(R$_4$)—;

A' is selected from the group consisting of —O—, —C(O)—, —CH$_2$—, —S(O)$_{0-2}$—, —N(R$_4$)—, and —N(Q-R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≤7;

R$_b$ is selected from the group consisting of halogen, hydroxy, alkyl, alkenyl, haloalkyl, alkoxy, and —N(R$_9$)$_2$; and m is 0 to 3;

or a pharmaceutically acceptable salt thereof.

In other embodiments, the present invention also provides compounds of the following Formulas VIII, IX, X, and XI:

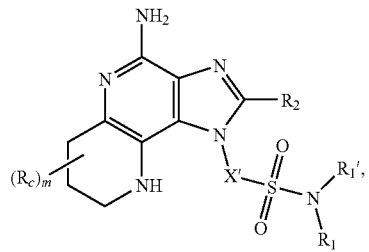

VIII

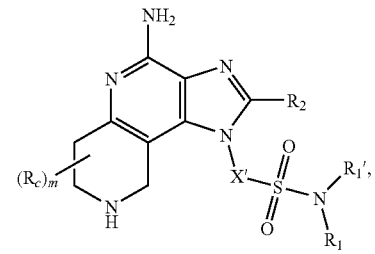

IX

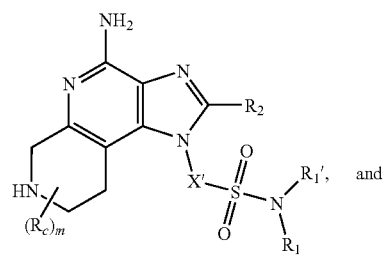

X and

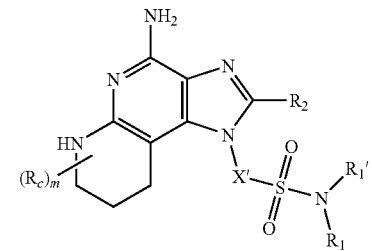

XI wherein:
X' is selected from the group consisting of —CH(R$_9$)—, —CH(R$_9$)-alkylene, and —CH(R$_9$)-alkenylene-; wherein the alkylene and alkenylene are optionally interrupted with one or more —O— groups;

$R_1$ and $R_1'$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
arylsulfonyl,
alkylsulfonyl, and
—$N(R_9)_2$,
or $R_1$ and $R_1'$ can join together to form a ring of the formula:

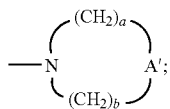

$R_2$ is selected from the group consisting of:
—$R_4$,
—X—$R_4$,
—X—Y—$R_4$, and
—X—$R_5$;
X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

$R_5$ is selected from the group consisting of:

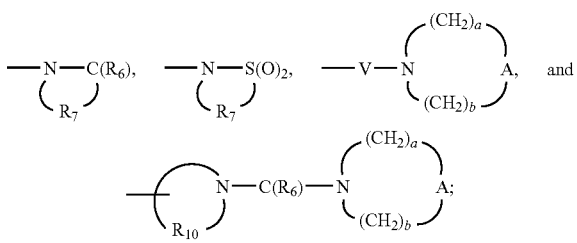

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —$CH_2$—, —$S(O)_{0-2}$—, and —N($R_4$)—;
A' is selected from the group consisting of —O—, —C(O)—, —$CH_2$—, —$S(O)_{0-2}$—, —N($R_4$)—, and —N(Q-$R_4$)—;
Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, and —C($R_6$)—N($OR_9$)—;
V is selected from the group consisting of —C($R_6$)—, —O—C($R_6$)—, —N($R_8$)—C($R_6$)—, and —$S(O)_2$—;
W is selected from the group consisting of a bond, —C(O)—, and —$S(O)_2$—;
a and b are independently integers from 1 to 6 with the proviso that a+b is ≤7;
$R_c$ is selected from the group consisting of halogen, hydroxy, alkyl, alkenyl, haloalkyl, alkoxy, alkylthio, and —$N(R_9)_2$; and
m is 0 to 3;
or a pharmaceutically acceptable salt thereof.

In one embodiment, the present invention also provides intermediate compounds of the following Formula XII:

(XII)

[Structure of Formula XII: imidazoquinoline with $(R_a)_n$, $R_2$, $X'$, $SO_2Cl$ substituents]

wherein:

X' is selected from the group consisting of —CH($R_9$)—, —CH($R_9$)-alkylene, and —CH($R_9$)-alkenylene-; wherein the alkylene and alkenylene are optionally interrupted with one or more —O— groups;

$R_2$ is selected from the group consisting of:
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—O—, —S(O)$_{0-2}$—, —S(O)$_2$—N($R_8$)—,
—C($R_6$)—, —C($R_6$)—O—, —O—C($R_6$)—,
—O—C(O)—O—, —N($R_8$)—Q—,
—C($R_6$)—N($R_8$)—, —O—C($R_6$)—N($R_8$)—,
—C($R_6$)—N(OR$_9$)—, [ring with $R_{10}$, N—Q—],
—N—C($R_6$)—N—W— (with $R_7$), —N—$R_7$—N—Q— (with $R_7$),
—V—N (with $R_{10}$), and [ring with $R_{10}$, N—C($R_6$)—N, $R_{10}$];

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino) alkylenyloxy, and in the case of alkyl, alkenyl, alkynyl, and heterocyclyl, oxo;

$R_5$ is selected from the group consisting of:

—N—C($R_6$)— (with $R_7$), —N—S(O)$_2$— (with $R_7$), —V—N [ring with (CH$_2$)$_a$, (CH$_2$)$_b$, A], and —[ring with $R_{10}$]—N—C($R_6$)—N [ring with (CH$_2$)$_a$, (CH$_2$)$_b$, A];

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —CH$_2$—, —S(O)$_{0-2}$—, and —N($R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(OR$_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—;
a and b are independently integers from 1 to 6 with the proviso that a+b is ≤7;
$R_a$ is selected from the group consisting of fluoro, alkyl, haloalkyl, alkoxy, and —N($R_9$)$_2$; and
n is 0 to 4;
or a pharmaceutically acceptable salt thereof.

In one embodiment, the present invention also provides intermediate compounds of the following Formula XIII:

(XIII)

[Structure of Formula XIII: imidazoquinoline with $(R_a)_n$, $R_2$, $X'$, $SO_2N(R_1)(R_1')$ substituents]

wherein:

X' is selected from the group consisting of —CH($R_9$)—, —CH($R_9$)-alkylene, and —CH($R_9$)-alkenylene-; wherein the alkylene and alkenylene are optionally interrupted with one or more —O— groups;

$R_1$ and $R_1'$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
arylsulfonyl,
alkylsulfonyl, and
—N($R_9$)$_2$,
or $R_1$ and $R_1$' can join together to form a ring of the formula:

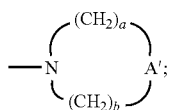

$R_2$ is selected from the group consisting of:
—$R_4$,
—X—$R_4$,
—X—Y—$R_4$, and
—X—$R_5$;
X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

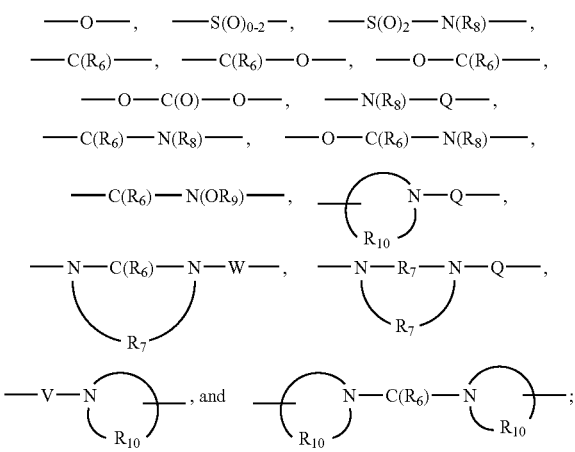

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino) alkylenyloxy, and in the case of alkyl, alkenyl, alkynyl, and heterocyclyl, oxo;
$R_5$ is selected from the group consisting of:

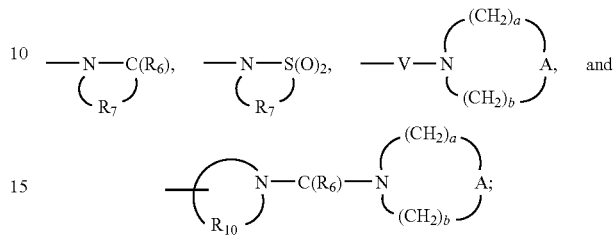

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —CH$_2$—, —S(O)$_{0-2}$—, and —N($R_4$)—;
A' is selected from the group consisting of —O—, —C(O)—, —CH$_2$—, —S(O)$_{0-2}$—, —N($R_4$)—, and —N(Q-$R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—;
a and b are independently integers from 1 to 6 with the proviso that a+b is ≤7;
$R_a$ is selected from the group consisting of fluoro, alkyl, haloalkyl, alkoxy, and —N($R_9$)$_2$; and
n is 0 to 4;
or a pharmaceutically acceptable salt thereof.

In one embodiment, the present invention also provides intermediate compounds of the following Formula XIV:

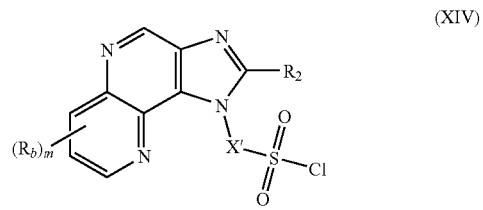

wherein:
X' is selected from the group consisting of —CH($R_9$)—, —CH($R_9$)-alkylene, and —CH($R_9$)-alkenylene-; wherein the alkylene and alkenylene are optionally interrupted with one or more —O— groups;
$R_2$ is selected from the group consisting of:
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

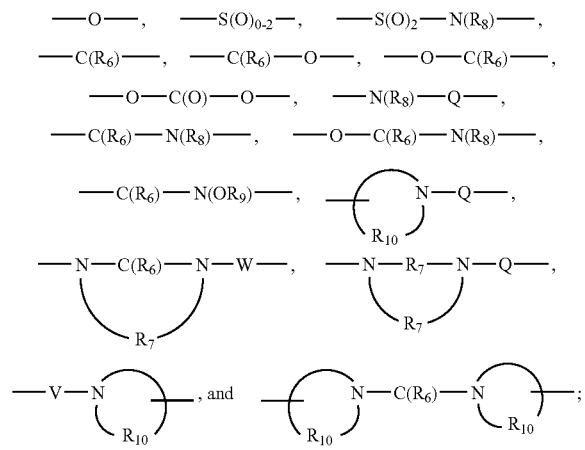

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

$R_5$ is selected from the group consisting of:

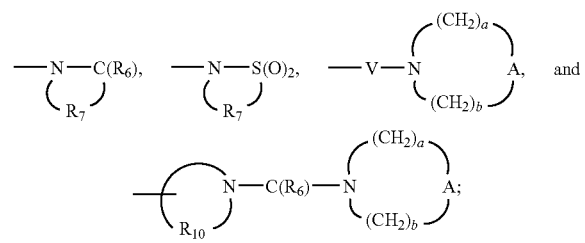

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —CH$_2$—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≤7;

$R_b$ is selected from the group consisting of halogen, hydroxy, alkyl, alkenyl, haloalkyl, alkoxy, and —N(R$_9$)$_2$; and m is 0 to 3;

or a pharmaceutically acceptable salt thereof.

In one embodiment, the present invention also provides intermediate compounds of the following Formula XV:

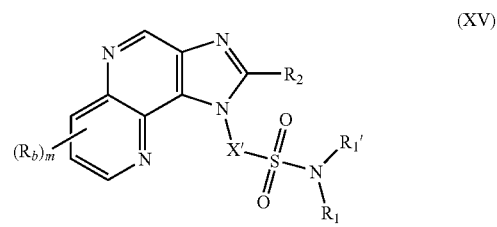

(XV)

wherein:

X' is selected from the group consisting of —CH(R$_9$)—, —CH(R$_9$)-alkylene, and —CH(R$_9$)-alkenylene-; wherein the alkylene and alkenylene are optionally interrupted with one or more —O— groups;

$R_1$ and $R_1'$ are independently selected from the group consisting of:

hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of:

hydroxy, alkyl, haloalkyl, hydroxyalkyl, alkoxy, haloalkoxy, halogen, cyano, nitro, arylsulfonyl, alkylsulfonyl, and

—N(R$_9$)$_2$, or R₁ and R₁' can join together to form a ring of the formula:

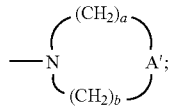

R₂ is selected from the group consisting of:
—R₄,
—X—R₄,
—X—Y—R₄, and
—X—R₅;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

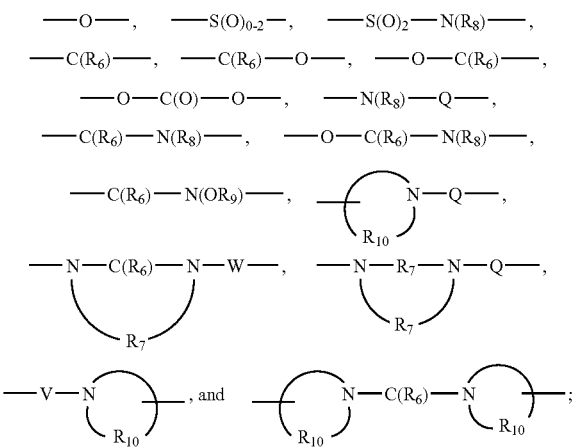

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

R₅ is selected from the group consisting of:

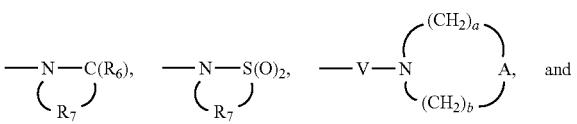

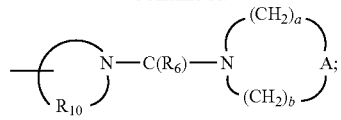

R₆ is selected from the group consisting of =O and =S;
R₇ is C₂₋₇ alkylene;
R₈ is selected from the group consisting of hydrogen, alkyl, alkoxyalkylenyl, and arylalkylenyl;
R₉ is selected from the group consisting of hydrogen and alkyl;
R₁₀ is C₃₋₈ alkylene;
A is selected from the group consisting of —O—, —C(O)—, —CH₂—, —S(O)₀₋₂—, and —N(R₄)—;
A' is selected from the group consisting of —O—, —C(O)—, —CH₂—, —S(O)₀₋₂—, —N(R₄)—, and —N(Q-R₄)—;
Q is selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, and —C(R₆)—N(OR₉)—;
V is selected from the group consisting of —C(R₆)—, —O—C(R₆)—, —N(R₈)—C(R₆)—, and —S(O)₂—;
W is selected from the group consisting of a bond, —C(O)—, and —S(O)₂—;
a and b are independently integers from 1 to 6 with the proviso that a+b is ≤7;
R_b is selected from the group consisting of halogen, hydroxy, alkyl, alkenyl, haloalkyl, alkoxy, and —N(R₉)₂; and
m is 0 to 3;
or a pharmaceutically acceptable salt thereof.

In one embodiment, the present invention also provides intermediate compounds of the following Formula XVI:

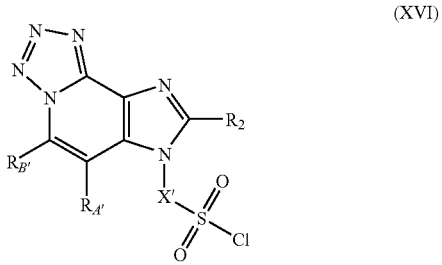

wherein:
X' is selected from the group consisting of —CH(R₉)—, —CH(R₉)-alkylene, and —CH(R₉)-alkenylene-; wherein the alkylene and alkenylene are optionally interrupted with one or more —O— groups;

R₂ is selected from the group consisting of:
—R₄,
—X—R₄,
—X—Y—R₄, and
—X—R₅;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

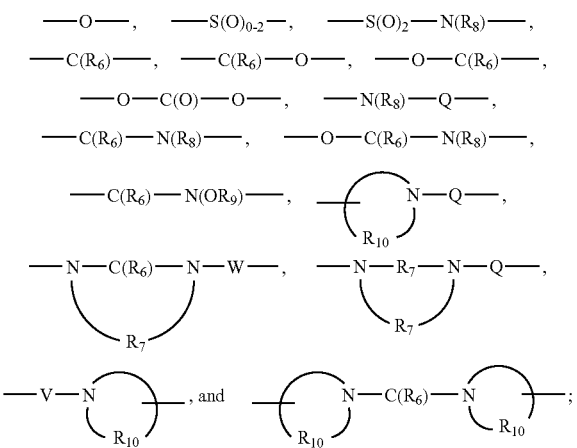

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

R$_5$ is selected from the group consisting of:

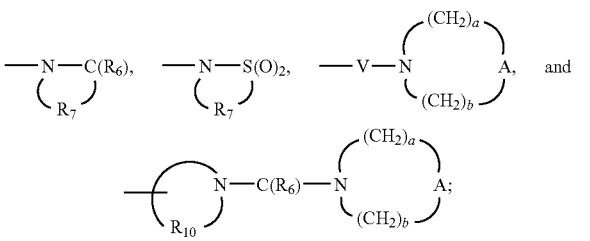

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —CH$_2$—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—;

a and b are independently integers from 1 to 6 with the proviso that a+b is ≤7; and
R$_{A'}$ and R$_{B'}$ are independently selected from the group consisting of hydrogen, halogen, alkyl, alkenyl, alkoxy, alkylthio, and —N(R$_9$)$_2$;
or a pharmaceutically acceptable salt thereof.

In one embodiment, the present invention also provides intermediate compounds of the Formula XVII:

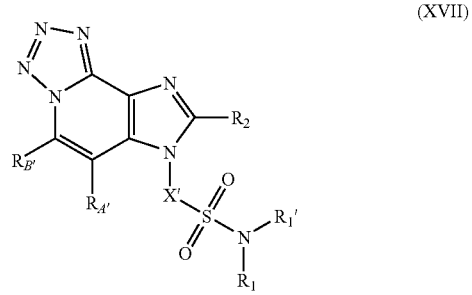

(XVII)

wherein:
X' is selected from the group consisting of —CH(R$_9$)—, —CH(R$_9$)-alkylene, and —CH(R$_9$)-alkenylene-; wherein the alkylene and alkenylene are optionally interrupted with one or more —O— groups;
R$_1$ and R$_1'$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
arylsulfonyl,
alkylsulfonyl, and
—N(R$_9$)$_2$,
or R$_1$ and R$_1'$ can join together to form a ring of the formula:

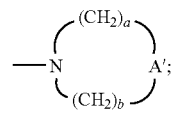

R$_2$ is selected from the group consisting of:
—R$_4$,
—X—R$_4$,

—X—Y—R$_4$, and
—X—R$_5$;

X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

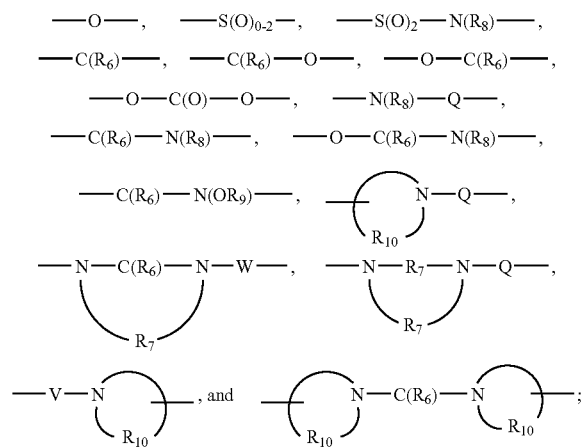

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo;

R$_5$ is selected from the group consisting of:

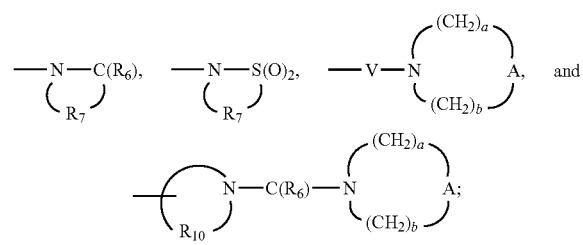

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —CH$_2$—, —S(O)$_{0-2}$—, and —N(R$_4$)—;

A' is selected from the group consisting of —O—, —C(O)—, —CH$_2$—, —S(O)$_{0-2}$—, —N(R$_4$)—, and —N(Q-R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≤7;

R$_{A'}$ and R$_{B'}$ are independently selected from the group consisting of hydrogen, halogen, alkyl, alkenyl, alkoxy, alkylthio, and —N(R$_9$)$_2$;

or a pharmaceutically acceptable salt thereof.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are use when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,3-dioxolanyl, aziridinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and the like. When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

The invention is inclusive of the compounds and salts thereof, described herein in any of their pharmaceutically acceptable forms, including isomers (e.g., diastereomers and enantiomers), solvates, polymorphs, and the like. In particular, if a compound is optically active, the invention specifically includes each of the compound's enantiomers as well as racemic mixtures of the enantiomers.

Herein, "non-interfering" means that the ability of the compound or salt, which includes a non-interfering substituent, to modulate (e.g., induce or inhibit) the biosynthesis of one or more cytokines is not destroyed by the non-interfering substituent. For certain embodiments, R" is hydrogen or a non-interfering substituent. Illustrative non-interfering, R" groups include those described herein for $R_2$.

When a group (or substituent or variable) is present more than once in any Formula described herein, each group (or substituent or variable) is independently selected, whether explicitly stated or not. For example, for the formula —N($R_9$)$_2$ each $R_9$ group is independently selected. In another example, when an $R_2$ and an A' group both contain an $R_4$ group, each $R_4$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., wherein: $R_1$, R", $R_2$, $R_1$', $R_A$, $R_B$, $R_A$, $R_B$, $R_a$, $R_b$, $R_c$, X', n, m, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, R" is hydrogen or a non-interfering substituent.

For certain embodiments, $R_1$ and $R_1$' are independently selected from the group consisting of: hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of: hydroxy, alkyl, haloalkyl, hydroxyalkyl, alkoxy, haloalkoxy, halogen, cyano, nitro, amino, alkylamino, dialkylamino, arylsulfonyl, and alkylsulfonyl.

For certain embodiments (particularly embodiments of Formulas I, Ia, Ib, II, III, IV, V, VI, VII, VIII, IX, X, and XI), $R_1$ and $R_1$' are independently selected from the group consisting of: hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of: hydroxy, alkyl, haloalkyl, hydroxyalkyl, alkoxy, haloalkoxy, halogen, cyano, nitro, arylsulfonyl, alkylsulfonyl, and —N($R_9$)$_2$.

For certain embodiments (particularly embodiments of Formulas I, Ia, Ib, II, III, IV, V, VI, VII, III, IX, X, and XI), $R_1$ is selected from the group consisting of hydrogen, alkyl, aryl, substituted aryl, arylalkylenyl, substituted arylalkylenyl, and heteroaryl.

For certain embodiments particularly embodiments of Formulas I, Ia, Ib, II, III, IV, V, VI, VI, VIII, IX, X, and XI), $R_1$ is selected from the group consisting of hydrogen, methyl, ethyl, propyl, butyl, cyclohexyl, phenyl, 4-methoxyphenyl, benzyl, 4-methoxybenzyl, 2-pyridyl, and 3-pyridyl.

For certain embodiments particularly embodiments of Formulas I, Ia, Ib, II, III, IV, V, VI, VII, VII, IX, X, and XI), $R_1$ is selected from the group consisting of hydrogen, methyl, ethyl, propyl, butyl, cyclohexyl, phenyl, 4-chlorophenyl, 4-fluorophenyl, 4-methoxyphenyl, benzyl, 4-methoxybenzyl, 2-pyridyl, and 3-pyridyl.

For certain embodiments (particularly embodiments of Formulas I, Ia, Ib, II, III, IV, V, VI, VII, VIII, IX, X, and XI), $R_1$ is selected from the group consisting of hydrogen, methyl, and isopropyl.

For certain embodiments (particularly embodiments of Formulas I, Ia, Ib, II, III, IV, V, VI, VII, VIII, IX, X, and XI), $R_1$' is hydrogen or alkyl.

For some embodiments (particularly embodiments of Formulas I, Ia, Ib, II, III, IV, V, VI, VII, VIII, IX, X, and XI), $R_1$' is hydrogen or methyl.

For certain embodiments, $R_1$ and $R_1$' can join together to form a ring of the formula:

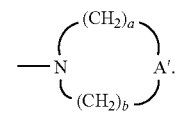

For certain embodiments, $R_1$ and $R_1$' can join together to form a ring of the formula:

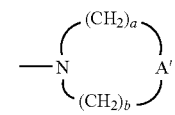

wherein A' is selected from the group consisting of —O—, —C(O)—, —CH$_2$—, —S(O)$_{0-2}$—, —N($R_4$)—, and —N(Q-$R_4$)—.

For certain embodiments (particularly embodiments of Formulas I, Ia, Ib, II, III, IV, V, VI, VII, VIII, IX, X, and XI), $R_1$ and R' can join together to form a ring of the formula:

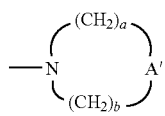

wherein A' is selected from the group consisting of —O—, —CH$_2$—, —NR$_4$—, and —N(Q-R$_4$)—.

For certain embodiments (particularly embodiments of Formulas I, Ia, Ib, II, III, IV, V, VI, VII, VIII, IX, X, and XI), R$_1$ and R' join together to form a morpholine ring.

For certain embodiments (particularly embodiments of Formulas I, Ia, Ib, III, IV, V, VI, VII, VIII, IX, X, and XI), R$_1$ and R$_1$' are both hydrogen.

For certain embodiments, R$_2$ is selected from the group consisting of: —R$_4$, —X—R$_4$, —X—Y—R$_4$, and —X—R$_5$.

For certain embodiments particularly embodiments of Formulas Ia, Ib, II, IIa, III, IV, V, VI, VII, VIII, IX, X, and XI), R$_2$ is selected from the group consisting of hydrogen, alkoxyalkylenyl, —R$_4$, —X—R$_4$, and —X—Y—R$_4$.

For certain embodiments particularly embodiments of Formulas Ia, Ib, II, IIa, III, IV, V, VI, VII, VIII, IX, X, and XI), R$_2$ is selected from the group consisting of hydrogen, alkoxyalkylenyl, hydroxyalkylenyl, —R$_4$, —X—R$_4$, and —X—Y—R$_4$.

For certain embodiments particularly embodiments of Formulas Ia, Ib, II, IIa, m, IV, V, VI, VII, VIII, IX, X, and XI), R$_2$ is selected from the group consisting of hydrogen, alkoxyalkylenyl, —R$_4$, —X—R$_4$, and —X—Y—R$_4$, wherein X is C$_{1-2}$ alkyl; Y is —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, or —C(R$_6$)—N(OR$_9$)—; and R$_4$ is alkyl.

For certain embodiments (particularly embodiments, of Formulas Ia, Ib, II, IIa, III, IV, V, VI, VII, VIII, IX, X, and XI), R$_2$ is selected from the group consisting of hydrogen, alkyl, alkoxyalkylenyl, hydroxyalkylenyl, and —X—R$_4$ and —X—Y—R$_4$, wherein X is C$_{1-2}$ alkyl; Y is —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, or —C(R$_6$)—N(OR$_9$)—; and R$_4$ is alkyl.

For certain embodiments (particularly embodiments of Formulas Ia, Ib, II, IIa, III, IV, V, VI, VII, VIII, IX, X, and XI), R$_2$ is selected from the group consisting of hydrogen, C$_{1-4}$ alkyl, C$_{1-4}$ alkyl-O—C$_{1-4}$ alkylenyl, and HO—C$_{1-3}$ alkylenyl.

For certain embodiments (particularly embodiments of Formulas Ia, Ib, II, IIa, III, IV, V, VI, VII, VIII, IX, X, and XI), R$_2$ is selected from the group consisting of hydrogen, C$_{1-4}$ alkyl, and C$_{1-4}$ alkyl-O—C$_{1-4}$ alkylenyl.

For certain embodiments, R$_2$ is selected from the group consisting of hydrogen, alkyl, and alkoxyalkylenyl.

For certain embodiments, R$_2$ is selected from the group consisting of hydrogen, methyl, ethyl, n-propyl, n-butyl, hydroxymethyl, 2-hydroxyethyl, ethoxymethyl, and 2-methoxyethyl.

For certain embodiments, R$_2$ is selected from the group consisting of methyl, ethyl, n-propyl, n-butyl, hydroxymethyl, 2-hydroxyethyl, ethoxymethyl, and 2-methoxyethyl.

For certain embodiments, R$_2$ is selected from the group consisting of methyl, ethyl, propyl, butyl, ethoxymethyl, and 2-methoxyethyl.

For certain embodiments, R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and hetero\yclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkylenyloxy, heteroaryl, heteroaryloxy, heteroarylalkylenyloxy, heterocyclyl, amino, alkylamino, dialkylamino, (dialkylamino)alkylenyloxy, and in the case of alkyl, alkenyl, alkynyl, and heterocyclyl, oxo.

For certain embodiments (particularly embodiments of Formulas Ia, Ib, II, IIa, III, IV, V, VI, VII, VIII, IX, X, and XI), R$_4$ is alkyl.

For certain embodiments, R$_5$ is selected from the group consisting of:

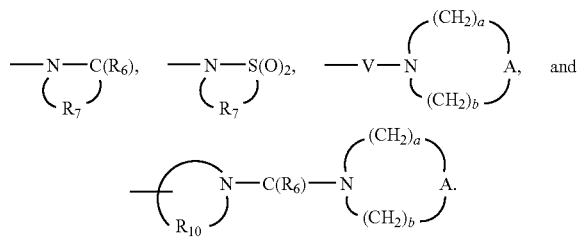

For certain embodiments, R$_6$ is selected from the group consisting of =O and =S.

For certain embodiments, R$_7$ is C$_{2-7}$ alkylene.

For certain embodiments, R$_8$ is selected from the group consisting of hydrogen, alkyl, alkoxyalkylenyl, and arylalkylenyl.

For certain embodiments, R$_9$ is selected from the group consisting of hydrogen and alkyl.

For certain embodiments, R$_{10}$ is C$_{3-8}$ alkylene.

For certain embodiments, R$_A$ and R$_B$ are independently selected from the group consisting of hydrogen, halogen, alkyl, alkenyl, alkoxy, alkylthio, and —N(R$_9$)$_2$.

For certain embodiments, R$_A$ and R$_B$ taken together form either a fused aryl ring that is unsubstituted or substituted by one or more R$_a$ groups, or a fused 5 to 7 membered saturated ring that is unsubstituted or substituted by one or more R$_c$ groups.

For certain embodiments, R$_A$ and R$_B$ taken together form a fused heteroaryl or 5 to 7 membered saturated ring, containing one heteroatom selected from the group consisting of N and S, wherein the heteroaryl ring is unsubstituted or substituted by one or more R$_b$ groups, and the 5 to 7 membered saturated ring is unsubstituted or substituted by one or more R$_c$ groups.

For certain embodiments, R$_A$ and R$_B$ are independently selected from the group consisting of hydrogen and C$_{1-4}$ alkyl.

For certain embodiments, R$_{A'}$ and R$_{B'}$ are independently selected from the group consisting of hydrogen, halogen, alkyl, alkenyl, alkoxy, alkylthio, and —N(R$_9$)$_2$.

For certain embodiments, R$_{A'}$ and R$_{B'}$ are independently selected from the group consisting of hydrogen and C$_{1-4}$ alkyl.

For certain embodiments, R$_{A'}$ and R$_{B'}$ are both methyl.

For certain embodiments, R$_a$ is selected from the group consisting of alkyl, alkoxy, hydroxy, fluoro, trifluoromethyl, amino, alkylamino, and dialkylamino.

For certain embodiments, $R_a$ is selected from the group consisting of fluoro, alkyl, haloalkyl, alkoxy, and —N($R_9$)$_2$.

For certain embodiments, $R_b$ is selected from the group consisting of halogen, hydroxy, alkyl, alkenyl, haloalkyl, alkoxy, and —N($R_9$)$_2$.

For certain embodiments, $R_c$ is selected from the group consisting of halogen, hydroxy, alkyl, alkenyl, haloalkyl, alkoxy, alkylthio, amino, alkylamino, and dialkylamino.

For certain embodiments, $R_c$ is selected from the group consisting of halogen, hydroxy, alkyl, alkenyl, haloalkyl, alkoxy, alkylthio, and —N($R_9$)$_2$.

For certain embodiments, A is selected from the group consisting of —O—, —C(O)—, —CH$_2$—, —S(O)$_{0-2}$—, and —N($R_4$)—

For certain embodiments, A' is selected from the group consisting of —O—, —C(O)—, —CH$_2$—, —S(O)$_{0-2}$—, —N($R_4$)—, and —N(Q-$R_4$)—.

For certain embodiments, A' is selected from the group consisting of —O—, —CH$_2$—, —N($R_4$)—, and —N(Q-$R_4$)—.

For certain embodiments, Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—.

For certain embodiments, V is selected from the group consisting of —C($R_6$)—, —O—C($R_6$)—, —N($R_8$)—C($R_6$)—, and —S(O)$_2$—.

For certain embodiments, W is selected from the group consisting of a bond, —C(O)—, and —S(O)$_2$—.

For certain embodiments, X is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups.

For certain embodiment (particularly embodiments of Formulas Ia, Ib, II, IIa, III, IV, V, VI, VII, VIII, IX, X, and XI), X is $C_{1-2}$ alkylene.

For certain embodiments, X' is selected from the group consisting of —CH($R_9$)—, —CH($R_9$)-alkylene, and —CH($R_9$)-alkenylene-; wherein the alkylene and alkenylene are optionally interrupted with one or more —O— groups.

For certain embodiments, X' is alkylene or alkenylene each of which may be optionally interrupted by one or more —O— groups.

For certain embodiments (particularly embodiments of Formulas I, Ia, Ib, II, III, IV, V, VI, VII, VIII, IX, X, and XI), X' is —(CH$_2$)$_{2-4}$—O—(CH$_2$)$_{2-4}$—.

For certain embodiments (particularly embodiments of Formulas I, Ia, Ib, II, III, IV, V, VI, VII, VIII, IX, X, and XI), X' is —(CH$_2$)$_{1-7}$.

For certain embodiments (particularly embodiments of Formulas I, Ia, Ib, II, III, IV, V, VI, VII, VIII, IX, X, and XI), X' is —(CH$_2$)$_2$—, —(CH$_2$)$_3$—, —(CH$_2$)$_4$—, —(CH$_2$)$_5$—, or —CH$_2$C(CH$_3$)$_2$CH$_2$—.

For certain embodiments (particularly embodiments of Formulas I, Ia, Ib, II, III, IV, V, VI, VII, VIII, IX, X, and XI), X' is —(CH$_2$)—C(CH$_3$)$_2$—.

For certain embodiments, Y is selected from the group consisting of: —O—, —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—,

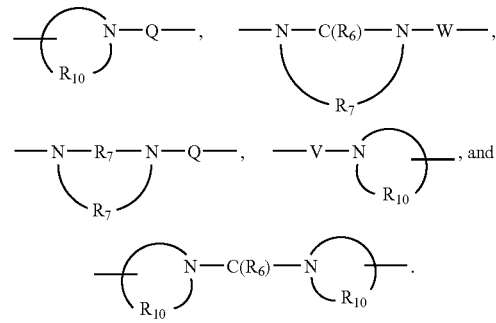

For certain embodiments, Y is selected from the group consisting of: —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—,

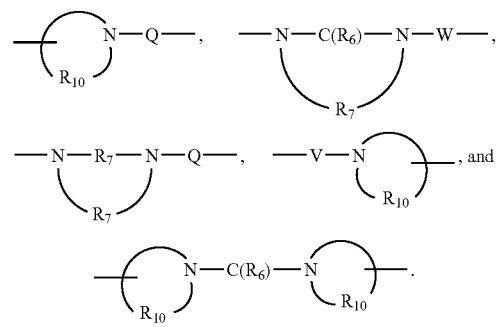

For certain embodiment particularly embodiments of Formulas Ia, Ib, II, IIa, III, IV, V, VI, VII, VIII, IX, X, and XI), Y is —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, or —C($R_6$)—N(O$R_9$)—.

For certain embodiments, a and b are independently integers from 1 to 6 with the proviso that a+b is ≤7.

For certain embodiments, m is 0 to 3. For certain embodiments (particularly embodiments of Formulas IV, V, VI, VII, VIII, IX, X, and XI), m is 0.

For certain embodiments, n is 0 to 4. For certain embodiments, n is 0 to 3. For certain embodiments (particularly embodiments of Formulas II, IIa, and III), n is 0.

For certain embodiments (particularly embodiments of Formulas I, Ia, Ib, II, III, IV, V, VI, VII, VIII, IX, X, and XI), $R_1$' is hydrogen or alkyl, and $R_1$ is selected from the group consisting of hydrogen, alkyl, aryl, substituted aryl, arylalkylenyl, substituted arylalkylenyl, and heteroaryl.

For some embodiments (particularly embodiments of Formulas I, Ia, Ib, II, III, IV, V, VI, VII, VIII, IX, X, and XI), $R_1$' is hydrogen or methyl, and $R_1$ is selected from the group consisting of hydrogen, methyl, ethyl, propyl, butyl, cyclohexyl, phenyl, 4-chlorophenyl, 4-fluorophenyl, 4-methoxyphenyl, benzyl, 4-methoxybenzyl, 2-pyridyl, and 3-pyridyl.

For some embodiments (particularly embodiments of Formulas I, Ia, Ib, II, III, IV, V, VI, VII, VIII, IX X and XI), $R_1$' is hydrogen or methyl, and $R_1$ is selected from the group consisting of hydrogen, methyl, ethyl, propyl, butyl, cyclohexyl, phenyl, 4-methoxyphenyl, benzyl, 4-methoxybenzyl, 2-pyridyl, and 3-pyridyl.

Preparation of the Compounds

Compounds of the invention can be prepared according to Reaction Scheme I, wherein $R_a$, $R_1$, $R_1'$, $R_2$, X', and n are as defined above.

In step (1) of Reaction Scheme I, an amine of Formula HO—X'—$NH_2$ is added to a 4-chloro-3-nitroquinoline of Formula XX to provide a hydroxy-substituted 3-nitroquinolin-4-amine of Formula XXI. The reaction is conveniently carried out by combining an amine of Formula HO—X'—$NH_2$ with a quinoline of Formula XX in the presence of a base such as triethylamine in a suitable solvent such as dichloromethane. The reaction can be carried out at ambient temperature, and the product can be isolated using conventional methods. Some amines of Formula HO—X'—$NH_2$, such as 4-aminobutanol, are commercially available; others can be prepared by known synthetic methods. Compounds of Formula XX are known and can be prepared according to known methods. See, for example; U.S. Pat. Nos. 4,689,338; 4,929,624; 5,268,376; 5,346,905; 5,389,640; and 5,756,747.

In step (2) of Reaction Scheme I, the hydroxy group of a 3-nitroquinolin-4-amine of Formula XXI is chlorinated using conventional methods to provide a 3-nitroquinolin-4-amine of Formula XXII. The chlorination is conveniently carried out by adding thionyl chloride to a solution of the 3-nitroquinolin-4-amine of Formula XXI in a suitable solvent such as dichloromethane. The reaction can be carried out at sub-ambient temperatures, such as 0° C., or at ambient temperature, and the product can be isolated using conventional methods.

In step (3) of Reaction Scheme I, a 3-nitroquinolin-4-amine of Formula XXII is reduced to provide a quinoline-3,4-diamine of Formula XXII. The reduction of the nitro group is conveniently carried out by adding an aqueous solution of sodium dithionite to a 3-nitroquinolin-4-amine of Formula XXII in a suitable solvent such as ethanol or a mixture of acetonitrile and ethanol. The reaction can be carried out at ambient temperature, and the product can be isolated by conventional methods.

Alternatively, step (3) can be carried out by hydrogenation in the presence of a heterogeneous hydrogenation catalyst, such as palladium on carbon or platinum on carbon. The reaction can be conveniently carried out on a Parr apparatus in a suitable solvent such as acetonitrile, ethyl acetate, toluene, or ethanol. The product can be isolated by conventional methods.

In step (4) of Reaction Scheme I, a quinoline-3,4-diamine of Formula XXIII is treated with a carboxylic acid equivalent to provide a 1H-imidazo[4,5-c]quinoline of Formula XXIV. Suitable carboxylic acid equivalents include orthoesters of Formula $R_2C(O\text{-alkyl})_3$, 1,1-dialkoxyalkyl alkanoates of Formula $R_2C(O\text{-alkyl})_2(O\text{—}C(O)\text{-alkyl})$, and acid chlorides of Formula $R_2C(O)Cl$. The selection of the carboxylic acid equivalent is determined by the desired substituent at $R_2$. For example, triethyl orthopropionate will provide a compound where $R_2$ is ethyl, and trimethyl orthovalerate will provide a compound where $R_2$ is a butyl group. The reaction is conveniently carried out by adding the carboxylic acid equivalent to a quinoline-3,4-diamine of Formula XXII in a suitable solvent such as toluene or pyridine. Optionally, catalytic pyridine hydrochloride can be added. The reaction is carried out at a temperature high enough to drive off alcohol or water formed during the reaction, for example, at the reflux temperature of the solvent.

Alternatively, step (4) can be carried out in two steps when an acid chloride of Formula $R_2C(O)Cl$ is used as the carboxylic acid equivalent. Part (i) of step (4) is conveniently carried out by adding the acid chloride to a solution of a quinoline-3,4-diamine of Formula XXIII in a suitable solvent such as dichloromethane or acetonitrile to afford an amide. Optionally, a tertiary amine such as triethylamine, pyridine, or 4-dimethylaminopyridine can be added. The reaction can be carried out at ambient temperature or at a sub-ambient temperature, such as 0° C. The amide product can be isolated and optionally purified using conventional techniques. Part (ii) of step (4) involves heating the amide prepared in part (i) to provide a 1H-imidazo[4,5-c]quinoline of Formula XXIV. The reaction is conveniently carried out in a suitable solvent such as toluene at a temperature sufficient to drive off water formed during the reaction. The reaction can also be carried out in a solvent such as ethanol or methanol in the presence of a base such as aqueous sodium hydroxide. The product can be isolated using conventional methods.

In step (5) of Reaction Scheme I, the chloro group of a 1H-imidazo[4,5-c]quinoline of Formula XIV is displaced with potassium thioacetate to provide a 1H-imidazo[4,5-c]quinoline of Formula XXV. The reaction is conveniently carried out by adding potassium thioacetate to a solution of a 1H-imidazo[4,5-c]quinoline of Formula XXV in a suitable solvent such as N,N-dimethylformamide. The reaction can be carried out at ambient temperature, and the product can be isolated using conventional methods.

In step (6) of Reaction Scheme I, the thioacetate group of a 1H-imidazo[4,5-c]quinoline of Formula XXV is hydrolyzed under basic conditions to provide a thiol-substituted 1H-imidazo[4,5-c]quinoline of Formula XXVI. The reaction is conveniently carried out by adding a solution of sodium methoxide in methanol to a solution of a 1H-imidazo[4,5-c]quinoline of Formula XXV in methanol. The reaction can be carried out at ambient temperature, and the product can be isolated using conventional methods.

In step (7) of Reaction Scheme I, the thiol group of a 1H-imidazo[4,5-c]quinoline of Formula XXVI is oxidized to a sulfonyl chloride of Formula XII. The reaction is conveniently carried out by adding a solution of sodium chlorate in a suitable solvent such as water to a solution of a thiol-substituted 1H-imidazo[4,5-c]quinoline of Formula XXVI in hydrochloric acid. The reaction can be carried out at a sub-ambient temperature such as 0° C., and the product can be isolated using conventional methods.

In step (8) of Reaction Scheme 1, the sulfonyl chloride of Formula XII is treated with an amine or an amine salt to provide a sulfonamide of Formula XIII. The reaction is conveniently carried out by adding an amine of Formula $NH(R_1)(R_1')$ to a sulfonyl chloride of Formula XII in a suitable solvent such as dichloromethane or pyridine. The reaction can be carried out at ambient temperature, and the product can be isolated using conventional methods.

Alternatively, step (8) can be carried out by adding an amine hydrochloride of Formula $(R_1)(R_1')NH\cdot HCl$ followed by aqueous potassium carbonate to a solution of a sulfonyl chloride of Formula XII in a suitable solvent such as dichloromethane. The reaction can be carried out at ambient temperature, and the product can be isolated using conventional methods.

In step (9) of Reaction Scheme I, a 1H-imidazo[4,5-c]quinoline of Formula XIII is oxidized to provide a 1H-imidazo[4,5-c]quinoline-5N-oxide of Formula XXVII using a conventional oxidizing agent capable of forming N-oxides. The reaction is conveniently carried out by adding 3-chloroperoxybenzoic acid to a compound of Formula XIII in a solvent such as dichloromethane or chloroform. The reaction can be carried out at ambient temperature, and the product can be isolated using conventional methods.

In step (10) of Reaction Scheme I, a 1H-imidazo[4,5-c]quinoline-5N-oxide of Formula XXVII is aminated to provide a 1H-imidazo[4,5-c]quinolin-4-amine of Formula II. Step (10) can be carried out by the activation of an N-oxide of Formula XXVII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXVII in a suitable solvent such as dichloromethane or chloroform and then adding p-toluenesulfonyl chloride. The reaction can be carried out at ambient temperature. The product or pharmaceutically acceptable salt thereof can be isolated using conventional methods.

Steps (9) and (10) can also be carried out as a one-pot procedure by first adding 3-chloroperoxybenzoic acid to a 1H-imidazo[4,5-c]quinoline of Formula XIII in a solvent such as dichloromethane or chloroform. After the reaction is stirred for a period long enough to complete the oxidation, ammonium hydroxide and p-toluenesulfonyl chloride are sequentially added. The reaction can be carried out at ambient temperature, and the product of Formula II or a pharmaceutically acceptable salt thereof can be isolated using conventional methods.

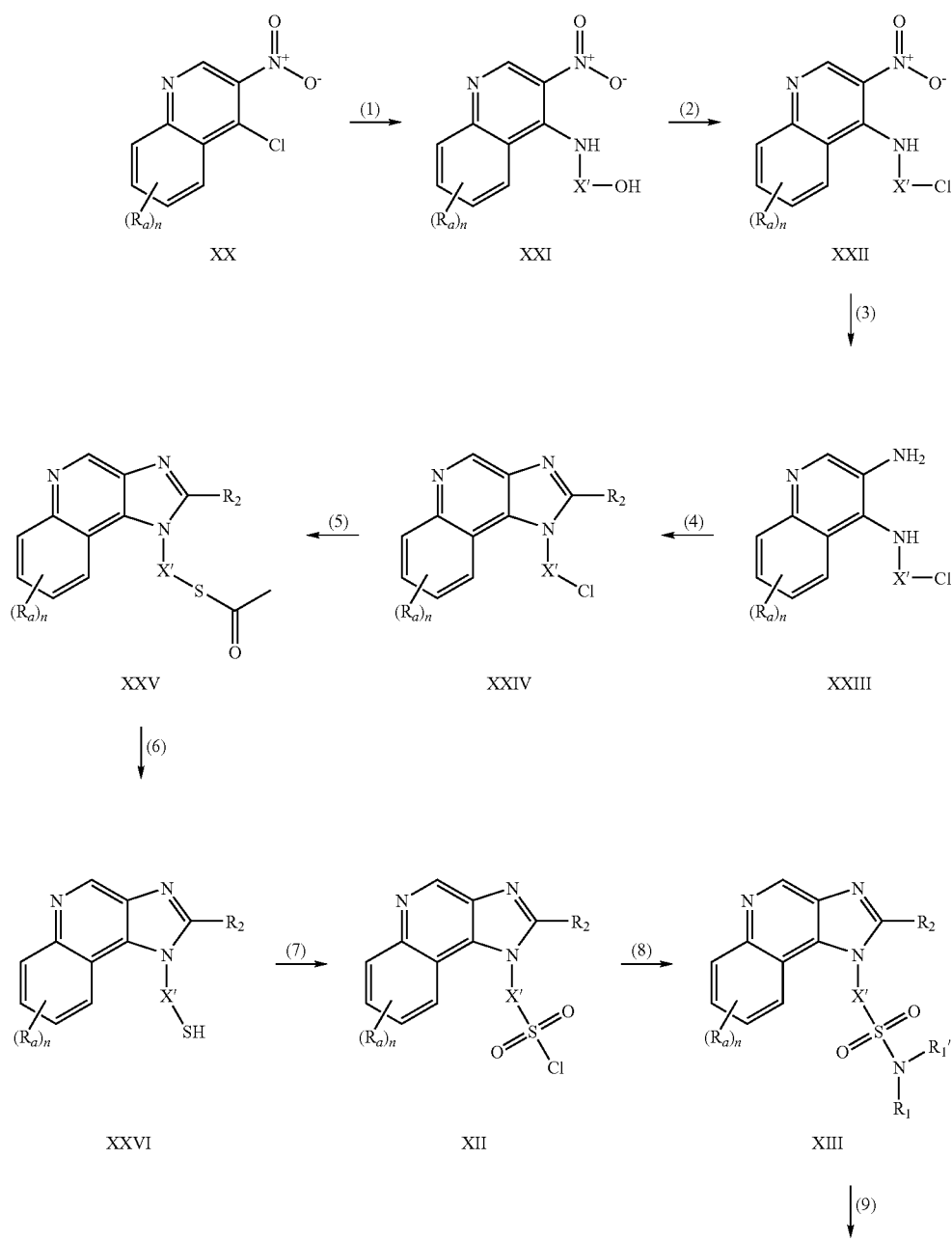

Reaction Scheme I

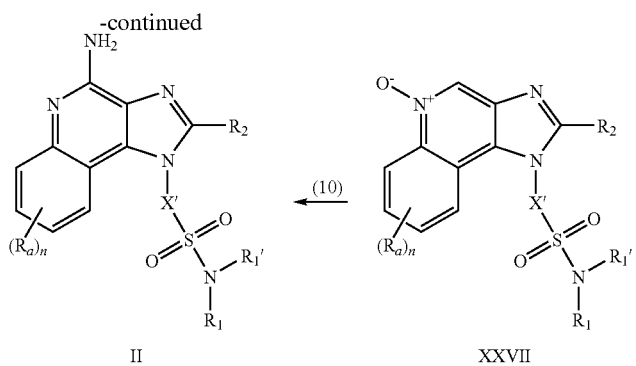

Compounds of the invention can be prepared according to Reaction Scheme II, wherein $R_a$, $R_1$, $R_1'$, $R_2$, $X'$, and n are as defined above.

In step (1) of Reaction Scheme II, a 3-nitroquinolin-4-amine of Formula XXI is reduced to provide a quinoline-3,4-diamine of Formula XXVIII. The reduction of the nitro group can be conveniently carried out as described in step (3) of Reaction Scheme I. The product can be isolated by conventional methods.

In step (2) of Reaction Scheme II, a quinoline-3,4-diamine of Formula XXVIII is reacted with a carboxylic acid or an equivalent thereof to provide a 1H-imidazo[4,5-c]quinoline of Formula XXIX. The reaction can be conveniently carried out as described in step (4) of Reaction Scheme I; the product can be isolated by conventional methods.

In step (3) of Reaction Scheme II, the hydroxyl group of a 1H-imidazo[4,5-c]quinoline of Formula XXIX is brominated using conventional methods to provide a 1H-imidazo[4,5-c]quinoline of Formula XXX. The bromination is conveniently carried out by adding thionyl bromide to a solution of the 1H-imidazo[4,5-c]quinoline of Formula XIXX in a suitable solvent such as dichloromethane. The reaction can be carried out at ambient temperature, and the product can be isolated using conventional methods.

In step (4) of Reaction Scheme II, the bromo group of a 1H-imidazo[4,5-c]quinoline of Formula XXX is displaced with sodium hydrosulfide hydrate to provide a thiol-substituted 1H-imidazo[4,5-c]quinoline of Formula XXVI. The reaction is conveniently carried out by adding sodium hydrosulfide hydrate to a solution of a 1H-imidazo[4,5-c]quinoline of Formula XXX in a suitable solvent such as ethanol. The reaction can be carried out at ambient temperature or at an elevated temperature, such as 45° C. The product can be isolated using conventional methods.

In step (5) of Reaction Scheme II, the thiol group of a 1H-imidazo[4,5-c]quinoline of Formula XXVI is oxidized to a sulfonyl chloride of Formula XII. The reaction can be carried out as described in step (7) of Reaction Scheme I. The product can be isolated using conventional methods.

In step (6) of Reaction Scheme II, the sulfonyl chloride of Formula XII is treated with an amine or an amine salt to provide a sulfonamide of Formula XIII. The reaction can be carried out as described in step (8) of Reaction Scheme I. The product can be isolated using conventional methods.

In step (7) of Reaction Scheme II, a 1H-imidazo[4,5-c]quinoline of Formula XIII is oxidized to provide a 1H-imidazo[4,5-c]quinoline-5N-oxide of Formula XXVII using a conventional oxidizing agent capable of forming N-oxides. The reaction can be carried out as described in step (9) of Reaction Scheme I. The product can be isolated using conventional methods.

In step (8) of Reaction Scheme II, a 1H-imidazo[4,5-c]quinoline-5N-oxide of Formula XXVII is aminated to provide a 1H-imidazo[4,5-c]quinolin-4-amine of Formula II. The reaction can be carried out as described in step (10) of Reaction Scheme I. The product or a pharmaceutically acceptable salt thereof can be isolated using conventional methods.

Reaction Scheme II

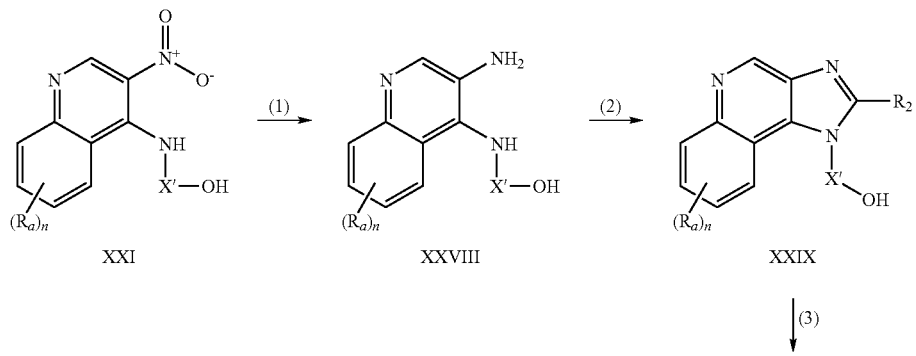

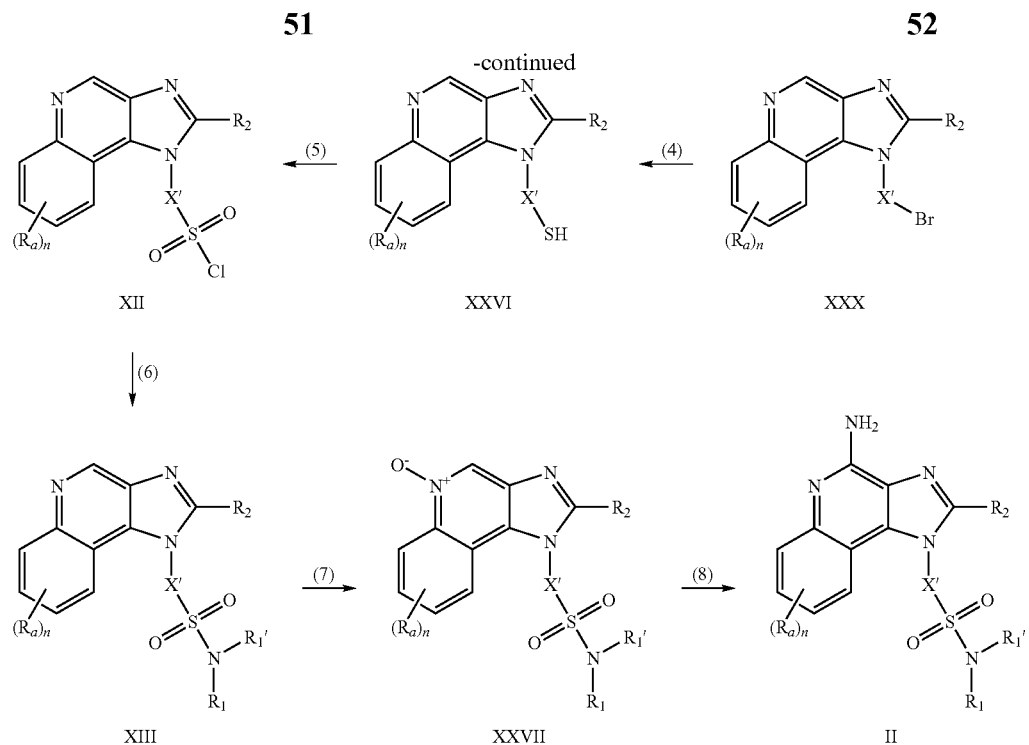

Compounds of the invention can be prepared according to Reaction Scheme III, wherein $R_a$, $R_1$, $R_1'$, $R_2$, $X'$, and n are as defined above.

In step (1) of Reaction Scheme III, the bromo group of a phthalimide of Formula XXXI is displaced with thiourea to provide a phthalimide hydrobromide of Formula XXXII. The reaction is conveniently carried out by combining a phthalimide of Formula XXXI and thiourea in a suitable solvent such as ethanol. The reaction can be carried out at an elevated temperature, such as the reflux temperature, and the product can be isolated using conventional methods. Some phthalimides of Formula XXXI, such as N-(3-bromopropyl)phthalimide, are commercially available; others can be prepared using known synthetic methods.

In step (2) of Reaction Scheme III, a thiourea-substituted phthalimide hydrobromide of Formula XXXII is converted to a thiourea-substituted phthalimide acetate of Formula XXXIII. The reaction is carried out by adding an aqueous solution of sodium acetate to an aqueous solution of the phthalimide hydrobromide of Formula XXXII. The reaction can be carried out at an elevated temperature, such as 100° C., and the product can be isolated using conventional methods.

In step (3) of Reaction Scheme III, the thiourea group of a thiourea-substituted phthalimide of Formula XXXII is converted to a sulfonyl chloride using the conditions described in step (7) of Reaction Scheme I.

In step (4) of Reaction Scheme III, a sulfonyl chloride-substituted phthalimide of Formula XX is treated with an amine to provide a sulfonamido-substituted phthalimide of Formula XXXV. The reaction is conveniently carried out by adding an amine of Formula $NH(R_1)(R_1')$ to a sulfonyl chloride-substituted phthalimide of Formula XXXIV in a suitable solvent such as tetrahydrofuran. The reaction can be carried out at ambient temperature, and the product can be isolated using conventional methods.

In step (5) of Reaction Scheme III, a sulfonamido-substituted phthalimide of Formula XXXV is hydrolyzed to provide a sulfonamido-substituted amine of Formula XXXVI. The reaction is carried out by adding hydrazine hydrate to a suspension of a phthalimide of Formula XXXV in a suitable solvent such as ethanol. The reaction can be carried out at an elevated temperature, such as reflux temperature, and the product can be isolated using conventional methods.

In step (6) of Reaction Scheme m, sulfonamido-substituted amine of Formula XXXVI is reacted with a 4-chloro-3-nitroquinoline of Formula XX to provide a 3-nitroquinolin-4-amine of Formula XXVII. The reaction is conveniently carried out by combining the amine of Formula XVI with a quinoline of Formula XX in the presence of a base such as triethylamine in a suitable solvent such as N,N-dimethylformamide. The reaction can be carried out at ambient temperature, and the product can be isolated using conventional methods.

In step (7) of Reaction Scheme III, a 3-nitroquinolin-4-amine of Formula XXXVII is reduced to provide a quinoline-3,4-diamine of Formula XXXVIII. The reduction of the nitro group is carried out by hydrogenation in the presence of a heterogeneous hydrogenation catalyst, such as palladium on carbon or platinum on carbon. The reaction can be conveniently carried out on a Parr apparatus in a suitable solvent such as ethanol. The product can be isolated by conventional methods.

In step (8) of Reaction Scheme III, a quinoline-3,4-diamine of Formula XXXVIII is reacted with a carboxylic acid or an equivalent thereof to provide a 1H-imidazo[4,5-c]quinoline of Formula XIII. The reaction can be conveniently carried out as described in step (4) of Reaction Scheme I; the product can be isolated by conventional methods.

In step (9) of Reaction Scheme III, a 1H-imidazo[4,5-c]quinoline of Formula XIII is oxidized to provide a 1H-imidazo[4,5-c]quinoline-5N-oxide of Formula XXVII using a conventional oxidizing agent capable of forming N-oxides. The reaction can be carried out as described in step (9) of Reaction Scheme I. The product can be isolated using conventional methods.

In step (10) of Reaction Scheme III, a 1H-imidazo[4,5-c]quinoline-5N-oxide of Formula XXVII is aminated to provide a 1H-imidazo[4,5-c]quinolin-4-amine of Formula II. The reaction can be carried out as described in step (10) of Reaction Scheme I. The product or a pharmaceutically acceptable salt thereof can be isolated using conventional methods.
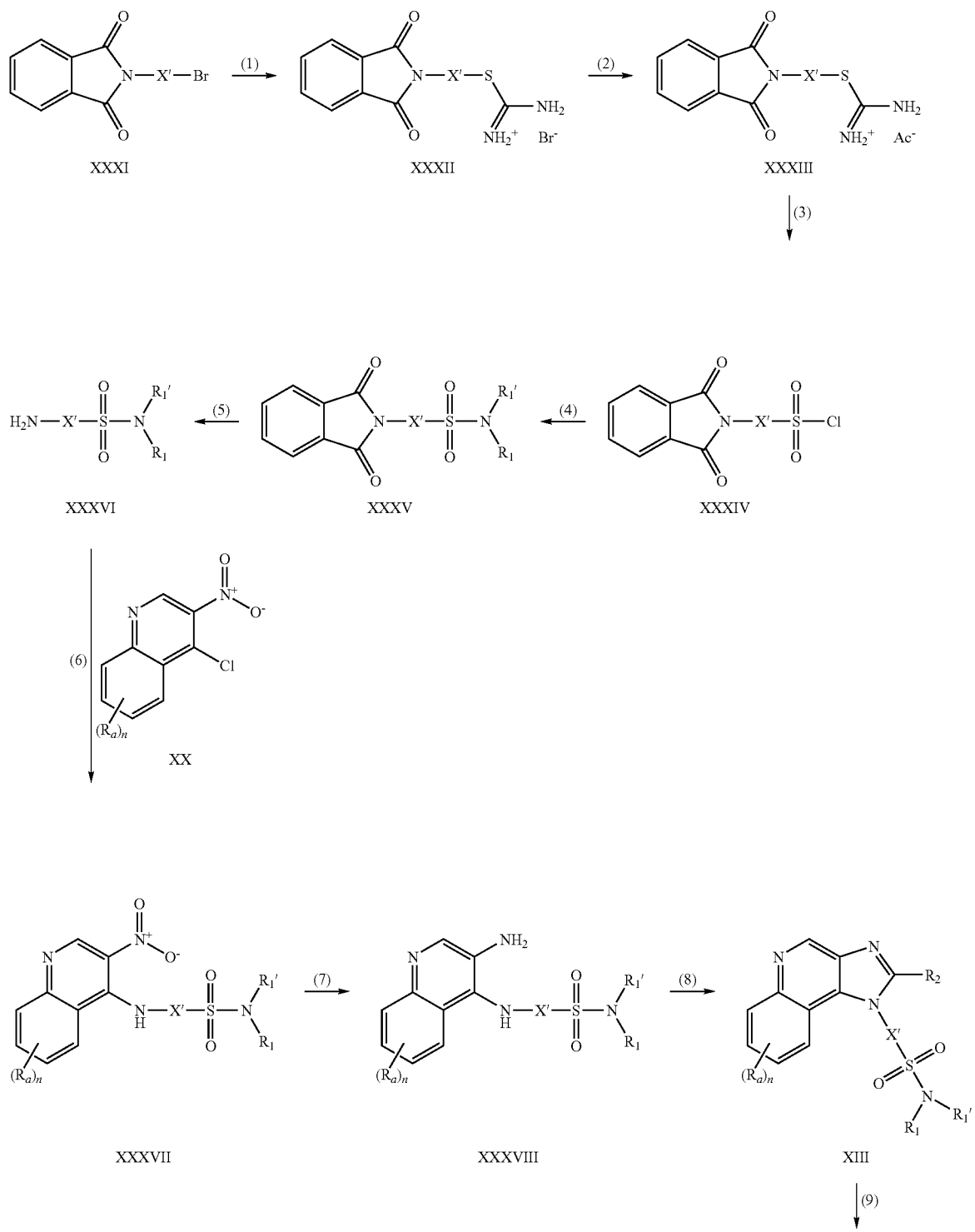

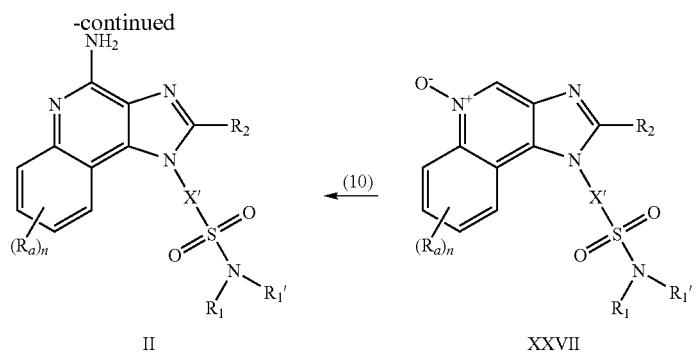

Compounds of the invention can also be prepared according to Reaction Scheme IV, wherein $R_d$ is alkyl, alkoxy, or $-N(R_9)_2$ and $R_{2b}$, $R_{1b}$, and $R_{1b'}$ are subsets of $R_2$, $R_1$, and $R_1'$ as defined above that do not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents.

As shown in Reaction Scheme IV, an 1H-imidazo[4,5-c] quinoline of Formula IIb can be reduced to a 6,7,8,9-tetrahydro-1H-imidazo[4,5-c]quinolin-4-amine of Formula IIIb. The reaction is conveniently carried out under heterogeneous hydrogenation conditions by adding platinum (IV) oxide to a solution of the compound of Formula IIb in trifluoroacetic acid and placing the reaction under hydrogen pressure. The reaction can be carried out on a Parr apparatus at ambient temperature. The product or pharmaceutically acceptable salt thereof can be isolated by conventional methods.

Reaction Scheme IV

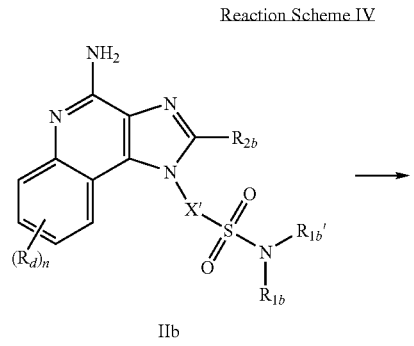

Compounds of the invention can be prepared according to Reaction Scheme V, wherein $R_b$, $R_1$, $R_1'$, $R_2$, X', and m are as defined above. Reaction Scheme V begins with a 4-chloro-3-nitro[1,5]naphthyridine of Formula XL. Compounds of Formula XL and their preparation are known; see, for example, U.S. Pat. No. 6,194,425 (Gerster) and U.S. Pat. No. 6,518,280 (Gerster). Steps (1) through (10) of Reaction Scheme V can be carried out as described for the corresponding steps (1) through (10) of Reaction Scheme I to provide a 1H-imidazo[4,5-c][1,5]naphthyridin-4-amine of Formula IV. The product or pharmaceutically acceptable salt thereof can be isolated by conventional methods.

Reaction Scheme V

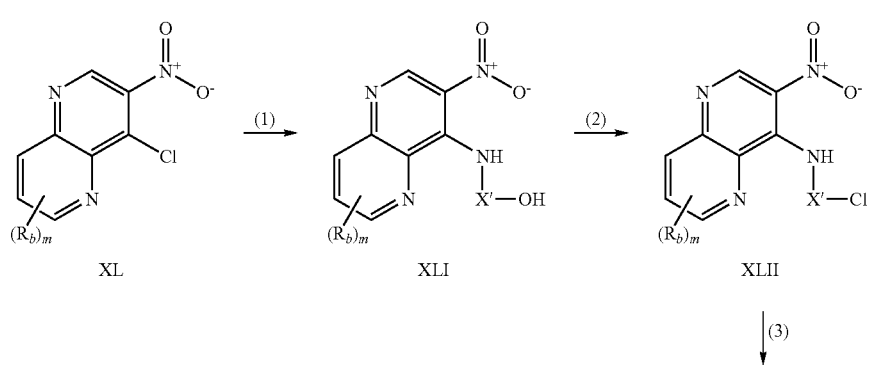

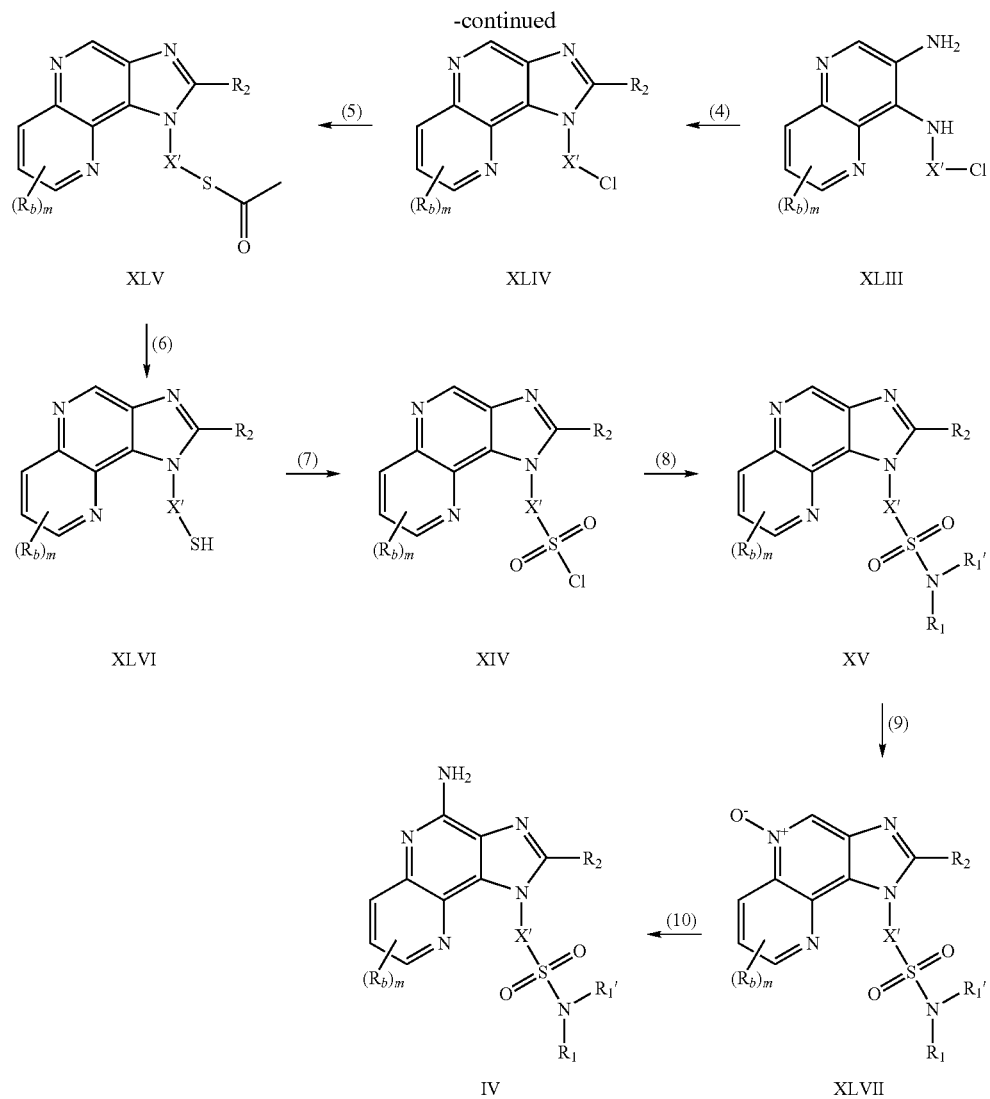

For some embodiments, pyridines of the invention are prepared according to Reaction Scheme VI, where $R_1$, $R_1'$, $R_2$, $R_A$, $R_B$, and X' are as defined above and Ph is phenyl. In step (1) of Reaction Scheme VI, the chloro group of a 7H-imidazo[4,5-c]tetrazolo[1,5-a]pyridine of Formula XLVIII is displaced with potassium thioacetate to provide a 7H-imidazo[4,5-c]tetrazolo[1,5-a]pyridine of Formula XLIX. The reaction can be carried out as described in step (5) of Reaction Scheme I; the product can be isolated by conventional methods. Compounds of Formula XLVIII and their preparation are known. See, for example, Dellaria et al, U.S. Publication No. US 2004/0010007 and International Publication No. WO 03/103584.

In step (2) of Reaction Scheme VI, the thioacetate group of a 7H-imidazo[4,5-c]tetrazolo[1,5-a]pyridine of Formula XLIX is hydrolyzed under basic conditions to provide a thiol-substituted 7H-imidazo[4,5-c]tetrazolo[1,5-a]pyridine of Formula L. The reaction can be carried out as described in step (6) of Reaction Scheme I; the product can be isolated by conventional methods.

In step (3) of Reaction Scheme VI, the thiol group of a 7H-imidazo[4,5-c]tetrazolo[1,5-a]pyridine of Formula L is oxidized to a sulfonyl chloride of Formula XVI according to the method described in step (7) of Reaction Scheme I. The product can be isolated by conventional methods.

In step (4) of Reaction Scheme VI, a sulfonyl chloride of Formula XVI is treated with an amine or an amine salt to provide a sulfonamide of Formula XVII. The reaction can be carried out according to the methods described in step (8) of Reaction Scheme I, and the 7H-imidazo[4,5-c]tetrazolo[1,5-a]pyridine of Formula XVII can be isolated by conventional methods.

In step (5) of Reaction Scheme VI, the tetrazolo ring is reductively removed from a 7H-imidazo[4,5-c]tetrazolo[1,5-a]pyridine of the Formula XVII to provide a 1H-imidazo[4,5-c]pyridin-4-anine of the Formula Ib or a pharmaceutically acceptable salt thereof. The reaction can be carried out by reacting the 7H-imidazo[4,5-c]tetrazolo[1,5-a]pyridine of Formula XVII with hydrogen in the presence of a catalyst and an acid. The hydrogenation can be conveniently run at ambient temperature on a Parr apparatus with a suitable catalyst, such as platinum (IV) oxide, and a suitable acid, such as trifluoroacetic acid. The product or pharmaceutically acceptable salt thereof can be isolated from the reaction mixture using conventional methods.

Alternatively, the tetrazolo ring can be removed from a 7H-imidazo[4,5-c]tetrazolo[1,5-a]pyridine of Formula XVII as shown in step (5a) by reaction with triphenylphosphine to form an N-triphenylphosphinyl intermediate of Formula LI. The reaction with triphenylphosphine can be run in a suitable solvent such as toluene or 1,2-dichlorobenzene under an atmosphere of nitrogen with heating, for example at the reflux temperature. In step (5b) of Reaction Scheme VI an N-triphenylphosphinyl intermediate of Formula LI is hydrolyzed to provide a 1H-imidazo[4,5-c]pyridin-4-amine of Formula Ib. The hydrolysis can be carried out by general methods well known to those skilled in the art, for example, by heating in a lower alkanol in the presence of an acid. The product can be isolated from the reaction mixture using conventional methods as the compound of Formula Ib or as a pharmaceutically acceptable salt thereof.

For some embodiments, naphthyridines of the invention are prepared from tetrazolo compounds of Formulas LII and LV according to Reaction Scheme VII, wherein $R_1$, $R_1'$, $R_2$, $R_b$, X' and m are as defined above and —OTf is a trifluoromethanesulfonate group. Compounds of Formula LII and LV and synthetic routes to these compounds are known; see, for example, U.S. Pat. No. 6,194,425 (Gerster) and U.S. Pat. No. 6,518,280 (Gerster).

In steps (1) and (1a) of Reaction Scheme VII, a tetrazolonaphthyridine of Formula LII or LV is reacted with an amino alcohol of the Formula HO—X'—$NH_2$ to form a compound of Formula LIII or LVI. The reaction can be carried out as described in step (1) of Reaction Scheme I. A hydroxy-substituted tetrazolonaphthyridine of Formula LIII or LVI is

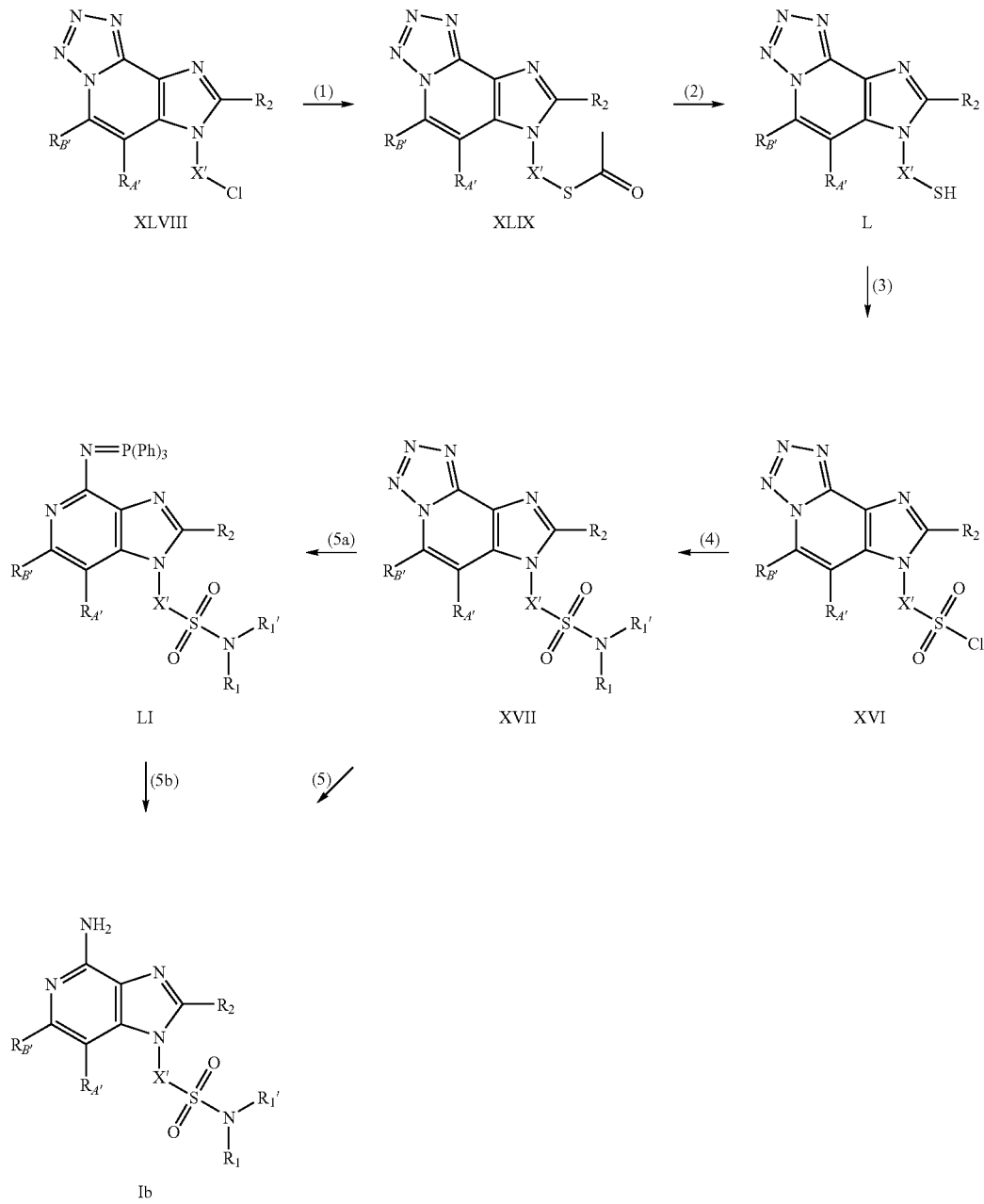

converted to a compound of Formula LIV or LVII according to the methods of steps (2) through (8) of Reaction Scheme I. The tetrazolo group of a compound of Formula LIV or LVII can then be removed to provide a 1H-imidazo[4,5-c]naphthyridin-4-amine of Formula VII or VI. The removal of the tetrazolo group can be carried out as described in step (5) or steps (5a) and (5b) of Reaction Scheme VI or by methods described in U.S. Pat. No. 6,194,425 (Gerster) and U.S. Pat. No. 6,518,280 (Gerster). The product or pharmaceutically acceptable salt thereof can be isolated by conventional methods.

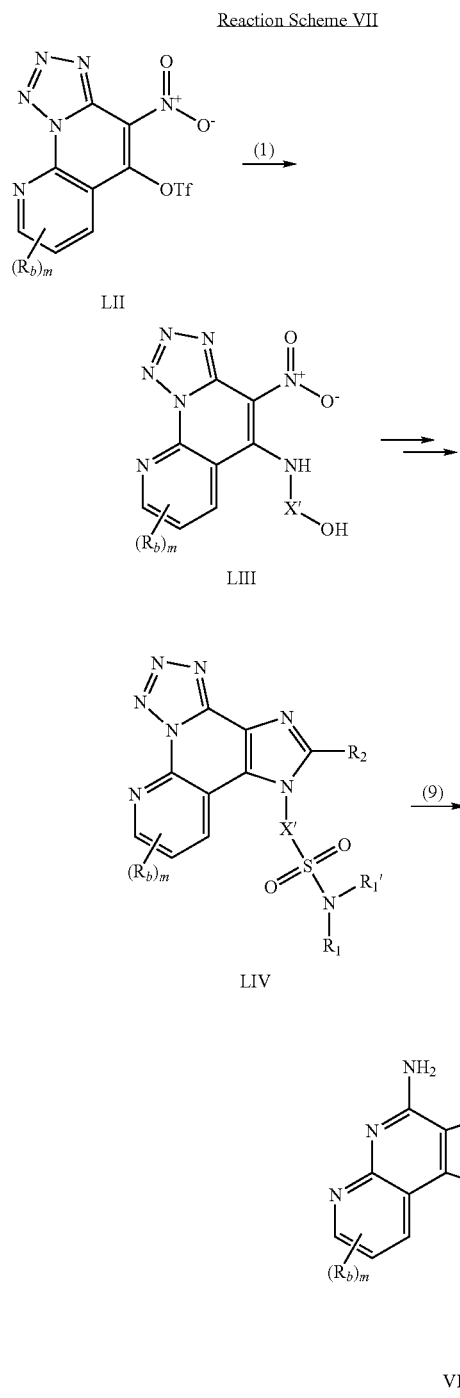

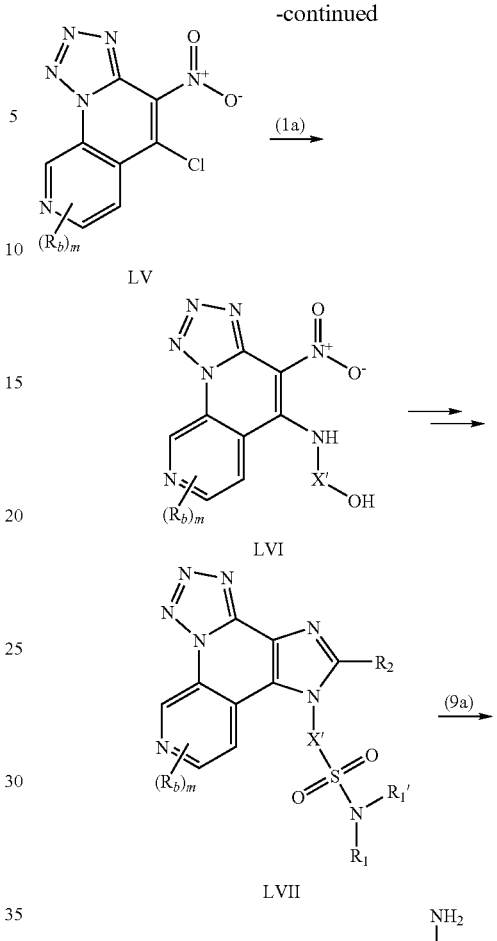

Compounds of the invention can be prepared according to Reaction Scheme VIII, wherein $R_a$, $R_1$, $R_1'$, $R_2$, X', and n are as defined above.

In step (1) of Reaction Scheme VIII, a chloro-substituted 1H-imidazo[4,5-c]quinoline of Formula XXIV is oxidized and then aminated to provide a chloro-substituted 1H-imidazo[4,5-c]quinoline of Formula LVIII. The reactions can be carried out as described in steps (9) and (10) of Reaction Scheme I. The product can be isolated using conventional methods.

In step (2) of Reaction Scheme VIII, the chloro group of a 1H-imidazo[4,5-c]quinolin-4-amine of Formula LVIII is displaced with potassium thioacetate to provide a thioacetate-substituted 1H-imidazo[4,5-c]quinoline of Formula LIX. The reaction can be carried out as described in step (5) of Reaction Scheme I. The product can be isolated using conventional methods.

In step (3) of Reaction Scheme VIII, a thioacetate-substituted 1H-imidazo[4,5-c]quinolin-4-amine of Formula LIX is hydrolyzed provide a thiol-substituted 1H-imidazo[4,5-c]quinoline of Formula LX. The reaction can be carried out as described in step (6) of Reaction Scheme I. The product can be isolated using conventional methods.

In step (4) of Reaction Scheme VIII, a thiol-substituted 1H-imidazo[4,5-c]quinoline of Formula LX is oxidized to a sulfonyl chloride of Formula LXI. The reaction can be carried out as described in step (7) of Reaction Scheme I. The product can be isolated using conventional methods.

In step (5) of Reaction Scheme VIII, a sulfonyl chloride of Formula LXI is treated with an amine or an amine salt to provide a sulfonamide of Formula II. The reaction can be carried out as described in step (8) of Reaction Scheme I. The product or a pharmaceutically acceptable salt thereof can be isolated using conventional methods.

In step (3) of Reaction Scheme IX, a 3,4-diaminoquinolinyl p-toluenesulfonate of Formula LXIII is reacted with a carboxylic acid or an equivalent thereof to provide a 1H-imidazo[4,5-c]quinoline of Formula LXIV. The reaction can be carried out as described in step (3) of Reaction Scheme I and the product can be isolated using conventional methods.

In step (4) of Reaction Scheme IX, the p-toluenesulfonate group of a 1H-imidazo[4,5-c]quinoline of Formula LXIV is displaced with potassium thiocyanate to provide a thiocyanate substituted 1H-imidazo[4,5-c]quinoline of Formula LXV. The reaction can be carried out by adding potassium thiocyanate to a solution of a 1H-imidazo[4,5-c]quinoline of Formula LXIV in a suitable solvent such as n-propanol. The reaction can be carried out at an elevated temperature, such as

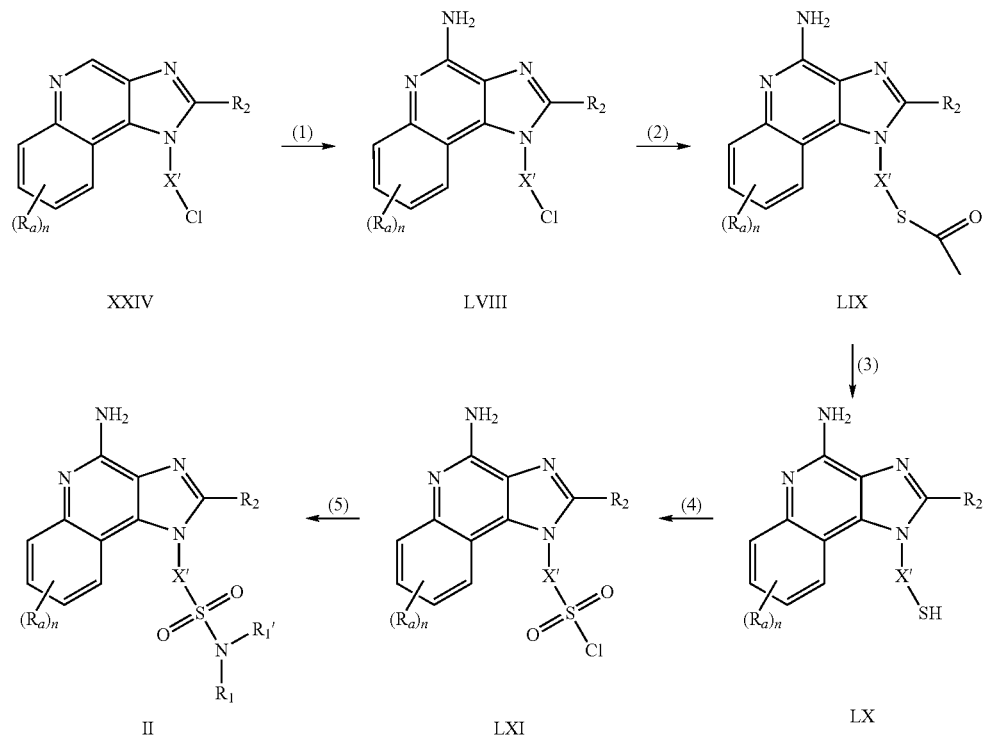

Reaction Scheme VIII

Compounds of the invention can be prepared according to Reaction Scheme IX, wherein $R_a$, $R_1$, $R_1'$, $R_2$, $X'$, and n are as defined above and Ts is (4-methylphenyl)sulfonyl.

In step (1) of Reaction Scheme IX, a hydroxy substituted 3-nitroquinolin-4-amine of Formula XXI is reacted with tosyl chloride to provide a 4-amino-3-nitroquinolinyl p-toluenesulfonate of Formula LXII. The reaction is conveniently carried out by combining tosyl chloride with a quinoline of Formula XXI in the presence of 4-dimethylaminopyridine in a suitable solvent such as pyridine. The reaction can be carried out at ambient temperature and the product can be isolated using conventional methods.

In step (2) of Reaction Scheme IX, a 4-amino-3-nitroquinolinyl p-toluenesulfonate of Formula LXII is reduced to provide a 3,4-diaminoquinolinyl p-toluenesulfonate of Formula LXIII. The reduction can be carried out as described in step (3) of Reaction Scheme I and the product can be isolated using conventional methods.

180-190° C., using a microwave synthesizer and the product can be isolated using conventional methods.

In step (5) of Reaction Scheme IX, the thiocyanate group of a 1H-imidazo[4,5-c]quinoline of Formula LXV is cleaved to provide a thiol substituted 1H-imidazo[4,5-c]quinoline of Formula XXVI. The reaction can be carried out by adding sodium borohydride to a solution of a 1H-imidazo[4,5-c]quinoline of Formula LXV in a suitable solvent such as ethanol. The reaction can be carried out at a sub-ambient temperature such as 0° C. and the product can be isolated using conventional methods.

In step (6) of Reaction Scheme IX, the thiol group of a 1H-imidazo[4,5-c]quinoline of Formula XXVI is oxidized to provide a sulfonyl chloride of Formula XXI. The reaction is carried out by treating a solution of a 1H-imidazo[4,5-c]quinoline of Formula XXVI in a suitable solvent such as dichloromethane with chlorine, prepared in situ from benzyltrimethylammonium chloride and trichloroisocyanuric acid.

The reaction can be carried out at a sub-ambient temperature such as 0° C. and the product can be isolated using conventional methods.

In step (7) of Reaction Scheme IX, a sulfonyl chloride of Formula XXI is reacted with an amine or amine salt to provide a sulfonamide substituted 1H-imidazo[4,5-c]quinoline of Formula XIII. The reaction can be carried out at described in step (8) of Reaction Scheme I and the product can be isolated using conventional methods.

Steps (6) and (7) are preferably carried out as a one pot procedure by first treating a chilled solution of a 1H-imidazo[4,5-c]quinoline of Formula XXVI in a suitable solvent such as dichloromethane with chlorine, prepared in situ from benzyltrimethylammonium chloride and trichloroisocyanuric acid. After the reaction is stirred for a period long enough to complete the oxidation, the amine is added and the reaction mixture is allowed to warm to ambient temperature.

In steps (8) and (9) of Reaction Scheme IX, a 1H-imidazo[4,5-c]quinoline of Formula XIII is oxidized and then aminated to provide a 1H-imidazo[4,5-c]quinoline-4-amine of Formula II. The reactions can be carried out as described in steps (9) and (10) respectively of Reaction Scheme I. The product or a pharmaceutically acceptable salt thereof can be isolated using conventional methods.

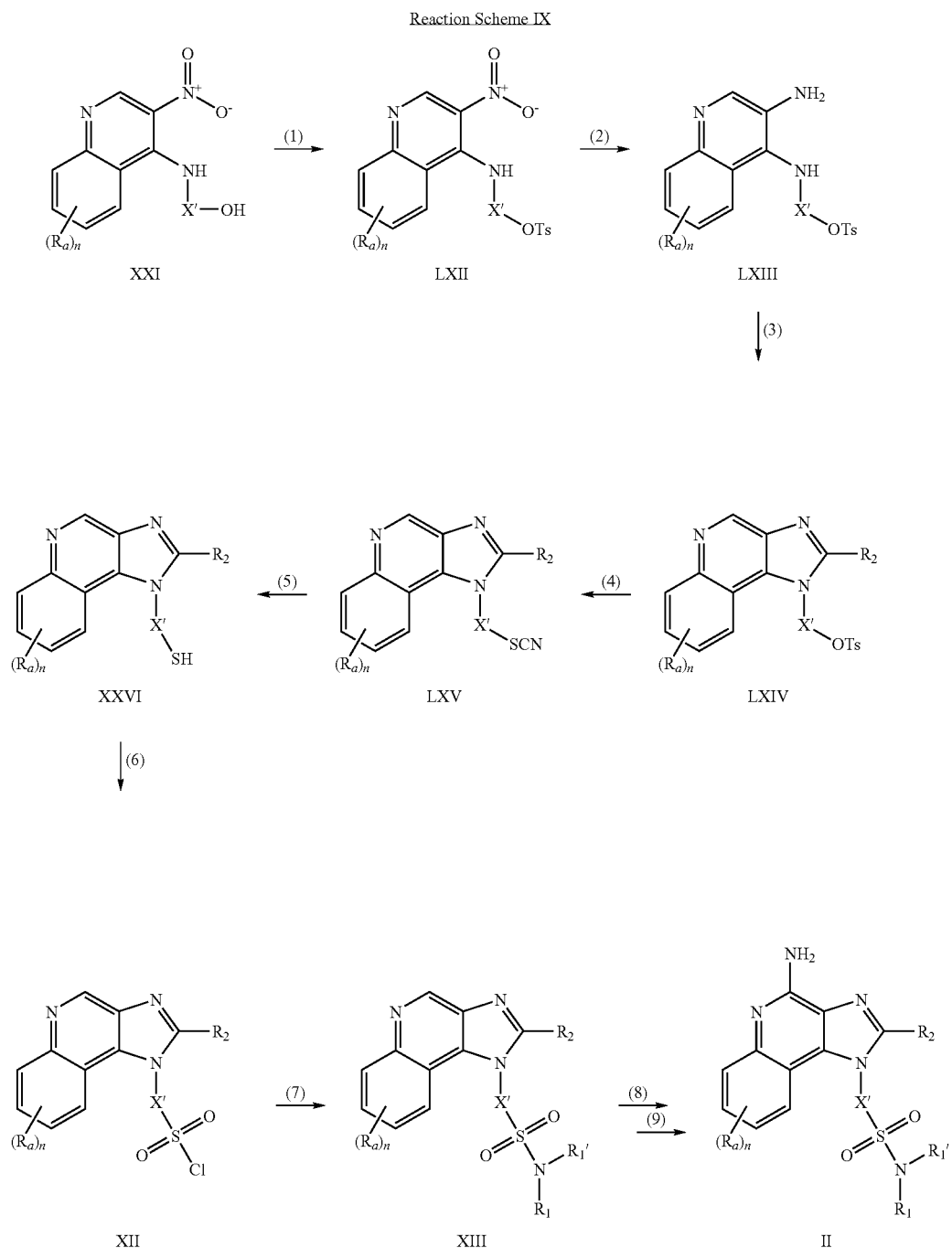

Reaction Scheme IX

Compounds of the invention can also be prepared using variations of the synthetic routes shown in Reaction Schemes I through IX. For example, tetrahydronaphthyridines can be prepared using the reduction method described in Reaction Scheme IV for the preparation of tetrahydroquinolines. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the test set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxyirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chiamydia, Mycoplasma, Pneumococcus, Neisseria, Clostridium, Bacillus, Corynebacterium, Mydobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, compounds or salts of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirs, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

Objects and advantages of this invention are further illustrated by the following examples, but the particular materials and amounts thereof recited in these examples, as well as other conditions and details, should not be construed to unduly limit this invention.

EXAMPLES

In the examples below high performance flash chromatography (HPFC) was carried out using either a HORIZON HPFC system (an automated high-performance flash purification product available from Biotage, Inc, Charlottesville, Va., USA) or an INTELLIFLASH Flash Chromatography System (an automated flash purification system available from AnaLogix, Inc, Burlington, Wis., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

N-Methyl 3-(4-amino-2-ethyl-1H-imidazo[4,5-c]quinolin-1-yl)propane-1-sulfonamide

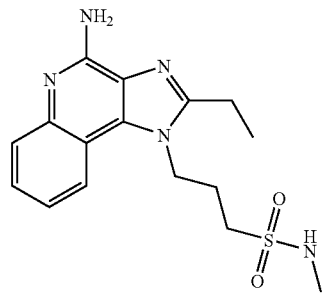 [SMILES: CCc1nc2c(N)nc3ccccc3c2n1CCCS(=O)(=O)NC]

Part A

A suspension of N-(3-bromopropyl)phthalimide (10.0 g, 37.3 mmol, 1.0 eq,) and thiourea (2.84 g, 1.0 eq.) was heated at reflux for 8 hours and then allowed to cool to ambient temperature overnight. The resulting precipitate was isolated by filtration and rinsed with ethanol (3×7 mL) to provide 12.16 g of 2-[3-(1,3-dioxo-1,3-dihydroisoindol-2-yl)propyl]isothiourea hydrobromide as a white solid, m.p. 170-172° C.

Part B

Saturated hot aqueous sodium acetate (~7 mL, ~4 eq.) was added to a stirred solution of 2-[3-(1,3-dioxo-1,3-dihydroisoindol-2-yl)propyl]isothiourea hydrobromide (12.16 g, 35.32 mmol) in hot (100° C.) water (90 mL). The reaction mixture was allowed to cool to ambient temperature overnight. The resulting precipitate was isolated by filtration, washed with cold water (2×15 mL), and dried at 35° C. under vacuum to provide 8.77 g of 2-[4-(1,3-dioxo-1,3-dihydroisoindol-2-yl)propyl]isothiourea acetic acid salt as a white solid, m.p. 152-153° C.

Part C

A solution of sodium chlorate (983 mg, 1.25 eq.) in water (2 mL) was added dropwise with stirring over a period of 5 minutes to a chilled (0° C.) suspension of 2-[3-(1,3-dioxo-1, 3-dihydroisoindol-2-yl)propyl]isothiourea acetic acid salt (2.39 g, 7.39 mmol, 1.0 eq.) in concentrated hydrochloric acid (10 mL). The reaction mixture was stirred for 30 minutes. A pale yellow solid was isolated by filtration, washed with ice cold water (2×10 mL), and dried under vacuum to provide 1.81 g of product. This material was stirred with chloroform (25 mL) and then filtered to remove an insoluble white solid. The filtrate was concentrated under reduced pressure to provide 1.33 g of 3-(1,3-dioxo-1,3-dihydroisoindol-2-yl)propane-1-sulfonyl chloride as a crystalline solid, m.p. 76-79° C.
Part D Methylamine (4.45 mL of 2.0 M in tetrahydrofuran, 2.0 eq.) was added dropwise with stirring to a solution of 3-(1,3-dioxo-1,3-dihydroisoindol-2-yl)propane-1-sulfonyl chloride (1.28 g, 4.45 mmol. 1.0 eq.) in tetrahydrofuran (THF). The reaction mixture was stirred for 2 hours and then concentrated under reduced pressure. The residue was taken up in chloroform (110 mL) and washed with water (35 mL). The aqueous wash was back extracted with chloroform (40 mL). The combined organics were dried over magnesium sulfate and concentrated under reduced pressure to provide 1.11 g of N-methyl 3-(1,3-dioxo-1,3-dihydroisoindol-2-yl)propane-1-sulfonamide as a white solid.
Part E Hydrazine hydrate (290 µL, 1.3 eq.) was added dropwise with stirring to a suspension of N-methyl 3-(1,3-dioxo-1,3-dihydroisoindol-2-yl)propane-1-sulfonamide (1.10 g, 3.90 mmol, 1.0 eq.) in ethanol (20 mL). The reaction mixture was heated to reflux. After 3.5 hours analysis by 1H NMR indicated that the reaction was about a 60:40 mixture of product and starting material. At 4.5 hours additional hydrazine hydrate (0.7 eq.) was added. After an additional 2 hours analysis by 1H NMR indicated that the reaction was complete. The reaction was allowed to cool to ambient temperature over the weekend and then concentrated under reduced pressure. The residue was dissolved in water (10 mL). Concentrated hydrochloric acid (0.65 mL, 2.0 eq.) was added dropwise to provide a thick white precipitate. The mixture was diluted with water (10 mL), stirred for 20 minutes, and filtered; the filter cake was rinsed with water (3×10 mL). The filtrate was concentrated under reduced pressure to provide 0.82 g of N-methyl 3-aminopropane-1-sulfonamide hydrochloride as a pale yellow solid.
Part F Triethylamine (1.14 mL, 2.1 eq.) was added to a stirred solution of N-methyl 3-aminopropane-1-sulfonamide hydrochloride (0.82 g, 3.90 mmol, 1.0 eq.) in N,N-dimethylformamide (DMF, 19.5 mL). 4-Chloro-3-nitroquinoline (813 mg, 3.90 mmol, 1.0 eq) was added to the resulting suspension in a single portion. The reaction mixture was stirred at ambient temperature for 1 hour and then concentrated under reduced pressure. The residue was partitioned between chloroform (100 mL) and water (30 mL). The aqueous layer was back extracted with chloroform (20 mL). The combined organics were dried over magnesium sulfate and then concentrated under reduced pressure to provide crude product as a yellow solid. The solid was triturated with diethyl ether (30 mL), isolated by filtration, and rinsed with diethyl ether (3×10 mL) to provide 0.85 g of N-methyl 3-[(3-nitroquinolin-4-yl)amino]propane-1-sulfonamide as a yellow solid.
Part G A suspension of N-methyl 3-[(3-nitroquinolin-4-yl)amino]propane-1-sulfonamide (0.45 g, 1.39 mmol) and 5% platinum on carbon (90 mg) in ethanol (30 mL) was hydrogenated at 35 psi (2.4×10⁵ Pa). After 3 hours analysis by thin layer chromatography (TLC) indicated that the reaction was complete. The reaction mixture was filtered to remove the catalyst and the filter cake was rinsed with ethanol (2×15 mL). The filtrate was concentrated under reduced pressure to provide 0.43 g of N-methyl 3-[(3-aminoquinolin-4-yl)amino]propane-1-sulfonamide as an orange oil.

Part H

Triethyl orthopropionate (308 µL, 1.1 eq.) was added to a stirred solution of the material from Part G (1.39 mmol, 1.0 eq.) in pyridine (7 mL). Pyridine hydrochloride (16 mg, 0.1 eq.) was added and the reaction mixture was heated at 100° C. for 2 hours. Analysis by TLC indicated that the reaction was complete at 1.5 hours. The reaction mixture was cooled to ambient temperature and then concentrated under reduced pressure. The residue was partitioned between chloroform (60 mL) and water (35 mL). The aqueous layer was back extracted with chloroform (20 mL). The combined organics were dried over magnesium sulfate and then concentrated under reduced pressure to provide crude product as a brown oil. The oil was purified by column chromatography (silica gel eluting with 10/90 methanol/chloroform) to provide 336 mg of N-methyl 3-(2-ethyl-1H-imidazo[4,5-c]quinolin-1-yl)propane-1-sulfonamide as a tan solid.
Part I 3-Chloroperoxybenzoic acid (98 mg, 1.2 eq.) was added to a suspension of N-methyl 3-(2-ethyl-1H-imidazo[4,5-c]quinolin-1-yl)propane-1-sulfonamide (110 mg, 0.33 mmol, 1.0 eq.) in chloroform (1.7 mL). All of the suspended material gradually went into solution. After 30 minutes analysis by TLC indicated that all the starting material had been consumed. After 1 hour concentrated ammonium hydroxide (2 mL) was added followed by tosyl chloride (76 mg, 1.2 eq.). The resulting biphasic mixture was stirred vigorously for 3 hours then the organic layer was separated. The aqueous layer was extracted with chloroform (3×2 mL). The extracts were combined with the original organic layer, dried over magnesium sulfate and concentrated under reduced pressure to provide 0.12 g of crude product as a tan foam. The foam was recrystallized from THF (~3 mL), isolated by filtration, and rinsed with ice cold THF (2×2 mL) to provide 32 mg of N-methyl 3-(4-amino-2-ethyl-1H-imidazo[4,5-c]quinolin-1-yl)propane-1-sulfonamide as a tan powder, mp 225-228° C. ¹H NMR (300 MHz, DMSO-d₆): δ 8.11 (d, J=7.6 Hz, 1H), 7.61 (dd, J=1.1, 8.4 Hz, 1H), 7.42 (t, J=7.2 Hz, 1H), 7.25 (dd, J=1.2, 8.1 Hz, 1H), 6.95 (q, J=4.9 Hz, 1H), 6.45 (s, 2H), 4.64 (t, J=7.7 Hz, 2H), 3.29 (m, 2H), 2.96 (q, J=7.5 Hz, 2H), 2.56 (d, J=4.9 Hz, 3H), 2.14 (m, 2H), 1.38 (t, J=7.4 Hz, 3H); MS (APCI) m/z: 348 (M+H). Anal. calcd. for C₁₆H₂₁N₅O₂S.0.08THF.0.14H₂O: C, 55.10; H, 6.21; N, 19.69. Found: C, 55.04; H, 6.19; N, 19.37.

Example 2

N,N-Dimethyl 3-(4-amino-2-ethyl-1H-imidazo[4,5-c]quinolin-1-yl)propane-1-sulfonamide

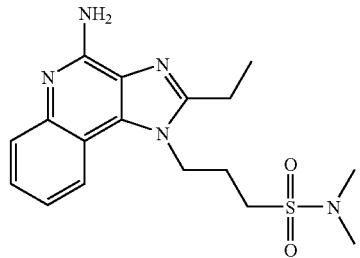 [SMILES: CCc1nc2c(N)nc3ccccc3c2n1CCCS(=O)(=O)N(C)C]

Part A

Dimethylamine (4.7 mL of 2.0 M in tetrahydrofuran, 2.1 eq.) was added dropwise with stirring to a solution of 3-(1,3-dioxo-1,3-dihydroisoindol-2-yl)propane-1-sulfonyl chloride (5.04 g, 17.5 mmol. 1.0 eq.) in tetrahydrofuran (THF). The reaction mixture was stirred for 1.5 hours and then concentrated under reduced pressure. The residue was dissolved in chloroform (120 mL), washed with water (50 mL), dried over magnesium sulfate and concentrated under reduced pressure to provide 3.80 g of crude N,N-dimethyl 3-(1,3-dioxo-1,3-dihydroisoindol-2-yl)propane-1-sulfonamide as a white solid.

Part B

Hydrazine hydrate (0.95 mL, 1.3 eq.) was added dropwise with stirring to a suspension of the crude product from Part A (1.0 eq.) in ethanol (60 mL). The reaction mixture was heated at reflux for 3 hours, allowed to cool to ambient temperature, and then concentrated under reduced pressure. The residue was suspended in water (80 mL). Concentrated hydrochloric acid (1.6 mL, 1.5 eq.) was added dropwise. The resulting suspension was stirred vigorously for 45 minutes and filtered; the filter cake was rinsed with water (2×35 mL). The filtrate was concentrated under reduced pressure to provide a white solid. This material was combined with methanol (50 mL) and then concentrated under reduced pressure. This procedure was repeated with acetonitrile (100 mL) to provide 2.50 g of N,N-dimethyl 3-aminopropane-1-sulfonamide hydrochloride as a white solid.

Part C

4-Chloro-3-nitroquinoline (2.34 g, 11.2 mmol, 1.0 eq.) was added in a single portion to a stirred solution of the material from Part B (12.3 mmol, 1.10 eq.) in DMF (45 mL). Triethylamine (3.3 mL, 2.1 eq.) was added dropwise. After 1 hour analysis by TLC indicated that the reaction was complete. The reaction mixture was concentrated under reduced pressure. The residue was partitioned between chloroform (200 mL) and water (50 mL). The aqueous layer was back extracted with chloroform (75 mL). The combined organics were dried over magnesium sulfate and then concentrated under reduced pressure to provide 2.72 g of N,N-dimethyl 3-[(3-nitroquinolin-4-yl)amino]propane-1-sulfonamide as a red solid.

Part D

Sodium borohydride (1.20 g, 4.0 eq.) was slowly added to a stirred solution of N,N-dimethyl 3-[(3-nitroquinolin-4-yl)amino]propane-1-sulfonamide (2.68 g, 7.92 mmol, 1.0 eq.) and nickel (II) chloride hexahydrate (188 mg, 0.1 eq.) in 1/1 methanol/chloroform (40 mL). After 30 minutes analysis by TLC indicated that the reaction was complete. The reaction mixture was concentrated under reduced pressure. The residue was suspended in chloroform (200 mL), washed with water (2×60 mL), dried over magnesium sulfate, and then concentrated under reduced pressure to provide a brown oil. TLC analysis of the oil showed multiple components. The combined aqueous washes were made basic (pH 8-9) and then extracted with chloroform (2×75 mL). The chloroform extracts were combined, dried over magnesium sulfate, and then concentrated under reduced pressure to provide 1.46 g of N,N-dimethyl 3-[(3-aminoquinolin-4-yl)amino]propane-1-sulfonamide as a brown foam.

Part E

Pyridine hydrochloride (55 mg, 0.1 eq.) was added to a stirred solution of the material from Part D (4.73 mmol, 1.0 eq.) in pyridine (24 mL). Triethyl orthopropionate (1.05 mL, 1.1 eq.) was added and the reaction mixture was heated at 100° C. for 2.5 hours. Analysis by TLC indicated that the reaction was complete. The reaction mixture was concentrated under reduced pressure. The residue was dissolved in chloroform (140 mL), washed with water (2×35 mL), dried over magnesium sulfate, and then concentrated under reduced pressure to give crude product as a brown foam. This material was purified by column chromatography (silica gel eluting with 1.5/98.5 methanol/chloroform) to provide 1.08 g of N,N-dimethyl 3-(2-ethyl-1H-imidazo[4,5-c]quinolin-1-yl)propane-1-sulfonamide as a brown foam.

Part F

3-Chloroperoxybenzoic acid (810 mg, 1.2 eq.) was added in a single portion to a solution of N,N-dimethyl 3-(2-ethyl-1H-imidazo[4,5-c]quinolin-1-yl)propane-1-sulfonamide (0.95 g, 2.74 mmol, 1.0 eq.) in chloroform (14 mL). After 30 minutes analysis by TLC indicated that all of the starting material had been consumed. After 2 hours concentrated ammonium hydroxide (14 mL) was added followed by tosyl chloride (679 mg, 1.3 eq.). The resulting biphasic mixture was stirred vigorously for 2.5 hours then the organic layer was separated. The aqueous layer was extracted with chloroform (2×20 mL). All organics were combined, dried over magnesium sulfate and then concentrated under reduced pressure to provide 1.25 g of crude product as a brown foam. The foam was triturated with ethyl acetate (7 mL), combined with petroleum ether, isolated by filtration, rinsed with 1/1 ethyl acetate petroleum ether (3×2 mL), and dried under vacuum at 70° C. for 4 days to provide 770 mg of an off white powder. This powder was combined with chloroform (80 mL), washed with saturated aqueous sodium bicarbonate (30 mL), dried over magnesium sulfate, and then concentrated under reduced pressure. The resulting solid was recrystallized from ethanol (~25 mL), isolated by filtration, rinsed with ice cold ethanol (2×5 mL), and then dried to provide 553 mg of N,N-dimethyl 3-(4-amino-2-ethyl-1H-imidazo[4,5-c]quinolin-1-yl)propane-1-sulfonamide as an off white powder, mp 209-211° C. $^1$H NMR (300 MHz, DMSO-$d_6$): δ 8.11 (m, 1H), 7.61 (dd, J=1.0, 8.3 Hz, 1H), 7.42 (m, 1H), 7.25 (m, 1H), 6.45 (br s, 2H), 4.64 (t, J=8.0 Hz, 2H), 3.35 (m, 2H), 2.96 (q, J=7.4 Hz, 2H), 2.77 (s, 6H), 2.18 (m, 2H), 1.38 (t, J=7.4 Hz, 3H); MS (APCI) m/z: 362 (M+H)$^+$; Anal. calcd. for $C_{17}H_{23}N_5O_2S$: C, 56.49; H, 6.41; N, 19.37. Found: C, 56.56; H, 6.31; N, 19.44

Example 3

N,N-Dimethyl 4-(4-amino-2-ethyl-1H-imidazo[4,5-c]quinolin-1-yl)butane-1-sulfonamide

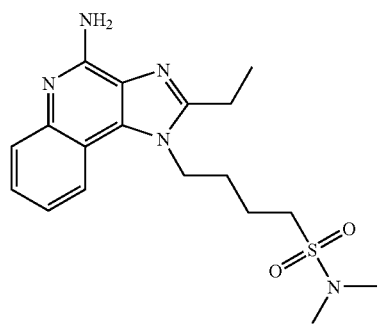 [SMILES: CCc1nc2c(N)nc3ccccc3c2n1CCCCS(=O)(=O)N(C)C]

Part A

Triethylamine (11.8 g, 57.2 mmol, 1.1. eq.) was added to a suspension of 4-chloro-3-nitroquinoline (20 g, 47.9 mmol, 1 eq.) in dichloromethane (200 mL). A solution of 4-aminobutanol (9.6 g, 52.7 mmol, 1.1 eq.) in dichloromethane (50 mL) was slowly added. After 2 hours the reaction mixture was concentrated under reduced pressure. The residue was slurried with water for about an hour. The resulting solid was isolated by filtration and air dried to provide crude product.

This material was purified by column chromatography (silica gel eluting sequentially with dichloromethane and 5% methanol in dichloromethane) to provide 24.1 g of 4-[(3-nitroquinolin-4-yl)amino]butanol.

Part B

A suspension of 4-[(3-nitroquinolin-4-yl)amino]butanol (18.2 g, 69.6 mmol) and 5% palladium on carbon in a mixture of toluene (450 mL) and ethanol (60 mL) was hydrogenated on a Parr apparatus until analysis by TLC indicated that the starting material had been consumed. The reaction mixture was filtered through a layer of CELITE filter aid and then concentrated under reduced pressure to provide 17 g of 4-[(3-aminoquinolin-4-yl)amino]butanol.

Part C

Triethyl orthopropionate (15.1 mL, 76.1 mmol, 1.1 eq.) and pyridine hydrochloride (catalytic amount) were added to a solution of 4-[(3-aminoquinolin-4-yl)amino]butanol (16 g, 69 mmol, 1 eq.) in pyridine (150 mL). The reaction mixture was heated at reflux for 1 hour at which time analysis by TLC indicated that all of the starting material had been consumed. The reaction mixture was concentrated under reduced pressure. The residue was triturated with water (300 mL). The resulting solid was isolated by filtration, recrystallized from ethyl acetate, isolated by filtration, washed with cold ethyl acetate, and then air dried to provide 8.2 g of 4-(2-ethyl-1H-imidazo[4,5-c]quinolin-1-yl)butanol as a solid.

Part D

Triphenylphosphine (3.35 g, 1.1 eq.) was added to a stirred suspension of 4-(2-ethyl-1H-imidazo[4,5-c]quinolin-1-yl) butanol (3.13 g, 11.6 mmol, 1.0 eq.) in THF (50 mL). N-bromosuccinimide (2.28 g, 1.1 eq.) was added in portions over a period of ~1 min. After 45 minutes additional triphenylphosphine (0.2 eq.) and N-bromosuccinimide (0.2 eq.) were added. After an additional hour analysis by TLC indicated that the reaction was essentially complete. The reaction mixture was quenched with methanol (2 mL) and then concentrated under reduced pressure. The residue was dissolved in chloroform (200 mL), washed sequentially with water (50 mL), 5% sodium sulfite (50 mL), and brine (50 mL), dried over magnesium sulfate, and then concentrated under reduced pressure. The residue was purified by column chromatography (silica gel eluting with a gradient of 100% chloroform to 4/96 methanol/chloroform) to provide 3.07 g of 1-(4-bromobutyl)-2-ethyl-1H-imidazo[4,5-c]quinoline as an orange solid.

Part E

A suspension of the material from Part D (9.21 mmol, 1.0 eq.) was gently warmed until a solution was obtained. The solution was allowed to cool to near ambient temperature and then sodium hydrosulfide hydrate (671 mg, 1.3 eq.) was added in a single portion. The reaction mixture was stirred at ambient temperature over the weekend then warmed to 45° C. for 4 hours. The reaction mixture was cooled to ambient temperature overnight and then additional sodium hydrosulfide hydrate (0.3 eq.) was added. After 6 hours chloroform (10 mL) was added. The reaction mixture was stirred overnight and then concentrated under reduced pressure. The residue was combined with chloroform (175 mL), washed sequentially with water (2×50 mL) and brine (75 mL), dried over magnesium sulfate, and then concentrated under reduced pressure to provide 2.75 g of a pink foam. This material was purified by column chromatography (silica gel eluting with a gradient of 3/97 to 4/96 methanol/chloroform) to provide 1.87 g of 4-(2-ethyl-1H-imidazo[4,5-c]quinolin-1-yl)butane-1-thiol as a white foam.

Part F

A solution of sodium chlorate (103 mg, 1.3 eq.) in water (0.5 mL) was added dropwise with stirring to a chilled (0° C.) solution of 4-(2-ethyl-1H-imidazo[4,5-c]quinolin-1-yl)butane-1-thiol (211 mg, 0.74 mmol, 1.0 eq.) in concentrated hydrochloric acid (1.0 mL). The reaction mixture was stirred for 1.5 hours. Chloroform (5 mL) was added followed by the addition of a solution of sodium dihydrogenphosphate (2.76 g, 23 mmol) in water (4 mL) to pH ~3. The reaction mixture was further diluted with water (20 mL) and chloroform (30 mL) and then aqueous saturated sodium bicarbonate was added with stirring until pH ~5. The layers were separated and the aqueous layer was extracted with chloroform (30 mL). The combined organics were dried over magnesium sulfate and then concentrated under reduced pressure to provide 190 mg of 4-(2-ethyl-1H-imidazo[4,5-c]quinolin-1-yl)butane-1-sulfonyl chloride as a light yellow semisolid.

Part G

Dimethylamine (160 μL of 40% w/w in water, 2.4 eq.) was added to a stirred solution of the material from Part F (0.54 mmol, 1.0 eq.) in dichloromethane (5.4 mL). After 1 hour additional dimethylamine (1 eq) was added. The reaction mixture was allowed to stand over the weekend and then was concentrated under reduced pressure. The residue was diluted with chloroform (60 mL), washed sequentially with water (2×25 mL) and saturated sodium bicarbonate (25 mL), dried over magnesium sulfate, and then concentrated under reduced pressure to provide 138 mg of a yellow oil. The oil was combined with the material from another run and purified by column chromatography (silica gel eluting with 5/95 methanol/chloroform) to provide 222 mg of N,N-dimethyl 4-(2-ethyl-1H-imidazo[4,5-c]quinolin-1-yl)butane-1-sulfonamide as a white foam.

Part H

Using the general method of Example 2 Part F, the material from Part G was oxidized with 3-chloroperoxybenzoic acid (167 mg, 1.1 eq) and then aminated (3 mL concentrated ammonium hydroxide and 135 mg of tosyl chloride). The crude product was purified by column chromatography (silica gel eluting with 5/95 methanol chloroform), triturated with ethyl acetate, and then dried under vacuum at 65° C. for 12 hours to provide 129 mg of N,N-dimethyl 4-(4-amino-2-ethyl-1H-imidazo[4,5-c]quinolin-1-yl)butane-1-sulfonamide as a white powder, mp 193-195° C. $^1$H NMR (300 MHz, DMSO-$d_6$): δ 8.05 (d, J=8.1 Hz, 1H), 7.60 (dd, J=1.2, 8.4 Hz, 1H), 7.41 (ddd, J=1.4, 7.1, 8.4 Hz, 1H), 7.25 (ddd, J=1.2, 7.1, 8.4 Hz, 1H), 6.43 (s, 2H), 4.56 (t, J=7.5 Hz, 2H), 3.10 (t, J=7.5 Hz, 2H), 2.96 (q, J=7.5 Hz, 2H), 2.73 (s, 6H), 1.88, (m, 4H), 1.38 (t, J=7.5 Hz, 3H); MS (APCI) m/z: 376 (M+H); Anal. calcd. for $C_{18}H_{25}N_5O_2S$: C, 57.58; H, 6.71; N, 18.65. Found: C, 57.54; H, 6.58; N, 18.65.

Example 4

N-Methyl 4-(4-amino-2-ethyl-1H-imidazo[4,5-c]quinolin-1-yl)butane-1-sulfonamide

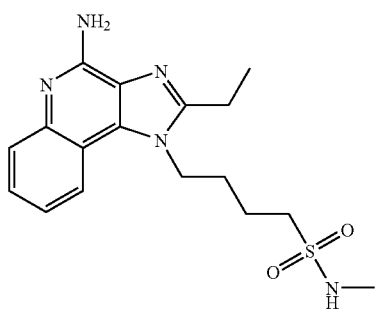 [SMILES: CCc1nc2c(N)nc3ccccc3c2n1CCCCS(=O)(=O)NC]

Part A

Methylamine hydrochloride (504 mg, 2.1 eq.) was added to a stirred mixture of 4-(2-ethyl-1H-imidazo[4,5-c]quinolin-1-yl)butane-1-sulfonyl chloride (1.25 g, 3.55 mmol, 1.0 eq.) and dichloromethane (36 mL). Aqueous potassium carbonate (1.30 mL of 6M, 2.2 eq.) was added. After 2 hours the reaction mixture was diluted with chloroform (100 mL), washed with brine (30 mL), dried over magnesium sulfate, and then concentrated under reduced pressure to provide 1.24 g of N-methyl 4-(2-ethyl-1H-imidazo[4,5-c]quinolin-1-yl)butane-1-sulfonamide as a light brown solid.

Part B

3-Chloroperoxybenozic acid (1.02 g of 77% max, 1.15 eq.) was added in a single portion to a stirred solution of the material from Part A (1.0 eq) in chloroform (36 mL). After 50 minutes concentrated ammonium hydroxide (8 mL) and tosyl chloride (819 mg, 1.2 eq.) were added. The reaction mixture was stirred for 2 hours and then the bulk of the chloroform was removed under reduced pressure. The residue was filtered, washed sequentially with water (10 mL) and isopropanol (2×8 mL), and then dried under vacuum to provide 722 mg of a tan solid. This material was recrystallized from 1,2-dichloroethane (~45 mL) then dried under vacuum at 50° C. for 18 hours to provide 491 mg of N-methyl 4-(4-amino-2-ethyl-1H-imidazo[4,5-c]quinolin-1-yl)butane-1-sulfonamide as an off-white powder, mp 190-191° C. $^1$H NMR (300 MHz, DMSO-$d_6$): δ 8.03 (d, J=8.4 Hz, 1H), 7.61 (dd, J=1.2, 8.4 Hz, 1H), 7.41 (ddd, J=1.2, 7.1, 8.3 Hz, 1H), 7.25 (ddd, J=1.2, 7.1, 8.3 Hz, 1H), 6.90 (q, J=4.8 Hz, 1H), 6.43 (br s, 2H), 4.54 (t, J=7.3 Hz, 2H), 3.08 (t, J=7.3 Hz, 2H), 2.96 (q, J=7.5 Hz, 2H), 2.54 (d, J=4.8 Hz, 3H), 1.94 (m, 2H), 1.81 (m, 2H), 1.38 (t, J=7.5 Hz, 3H); MS (APCI) m/z: 362 (M+H); Anal. calcd. for $C_{17}H_{23}N_5O_2S$·0.05 $C_2H_4Cl_2$: C, 56.05; H, 6.38; N, 19.11. Found: C, 55.83; H, 6.13; N, 18.92.

Example 5

N-(4-Methoxybenzyl) 4-(4-amino-2-ethyl-1H-imidazo[4,5-c]quinolin-1-yl)butane-1-sulfonamide

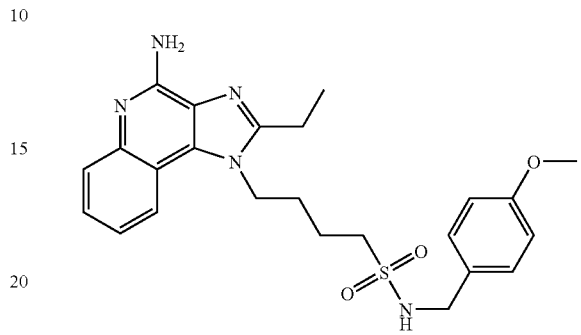

Part A

Aqueous potassium carbonate (0.35 mL of 6M, 1.2 eq.) was added to a stirred solution of 4-(2-ethyl-1H-imidazo[4,5-c]quinolin-1-yl)butane-1-sulfonyl chloride (0.62 g, 1.76 mmol, 1.0 eq.) in dichloromethane (17 mL). 4-Methoxybenzylamine (0.25 mL, 1.1 eq.) was added dropwise and the reaction mixture was stirred for 2 hours. Additional aqueous potassium carbonate (1.2 eq.) and 4-methoxybenzylamine (1.1 eq.) were added and the reaction mixture was stirred over the weekend. The reaction mixture was diluted with chloroform (140 mL), washed with water (2×40 mL), dried over magnesium sulfate, and then concentrated under reduced pressure to provide a brown oil. The oil was twice purified by column chromatography (silica gel eluting with 5/95 methanol/chloroform) to provide 412 mg of N-(4-methoxybenzyl) 4-(2-ethyl-1H-imidazo[4,5-c]quinolin-1-yl)butane-1-sulfonamide as a white foam.

Part B

3-Chloroperoxybenzoic acid (257 mg of 77% max, 1.15 eq.) was added to a stirred solution of the material from Part A (1.0 eq) in chloroform (9.1 mL). After 1 hour concentrated ammonium hydroxide (3 mL) and tosyl chloride (207 mg, 1.2 eq.) were added. The reaction mixture was stirred vigorously for 20 hours, diluted with water (4 mL), and partially concentrated under reduced pressure. The residue was diluted with water (5 mL) and then extracted with chloroform (1×40 mL, then 4×20 mL). The combined extracts were dried over magnesium sulfate and then concentrated under reduced pressure to provide 0.47 g of a brown foam. The foam was purified by column chromatography (silica gel eluting with 25/75 80/18/2 chloroform/methanol/ammonium hydroxide (CMA)/chloroform) to provide 0.20 g of a tan foam. This material was reconcentrated from hot ethyl acetate/diethyl ether, recrystallized from ethanol, isolated by filtration, rinsed with ethanol (2×2 mL), and dried under vacuum at 80° C. for 24 hours to provide 80 mg of N-(4-methoxybenzyl) 4-(4-amino-2-ethyl-1H-imidazo[4,5-c]quinolin-1-yl)butane-1-sulfonamide as a white powder, mp 176-177° C. $^1$H NMR (300 MHz, DMSO-$d_6$): δ 8.00 (d, J=8.1 Hz, 1H), 7.61 (dd, J=1.1, 8.3 Hz, 1H), 7.56 (t, J=5.9 Hz, 1H), 7.42 (ddd, J=1.1, 7.2, 8.3 Hz, 1H), 7.25 (m, 3H), 6.84 (m, 2H), 6.43 (br s, 2H), 4.48 (t, J=7.6 Hz, 2H), 4.03 (d, J=5.9 Hz, 2H), 3.67 (s, 3H), 2.93 (m, 4H), 1.80 (m, 4H), 1.38 (t, J=7.5 Hz, 3H); MS (APCI) m/z: 468 (M+H); Anal. calcd. for $C_{24}H_{29}N_5O_3S \cdot 0.05$ EtOH, C, 61.60; H, 6.28; N, 14.90. Found: C, 61.39; H, 6.53; N, 14.84.

Example 6

4-(4-Amino-2-ethyl-1H-imidazo[4,5-c]quinolin-1-yl)butane-1-sulfonamide

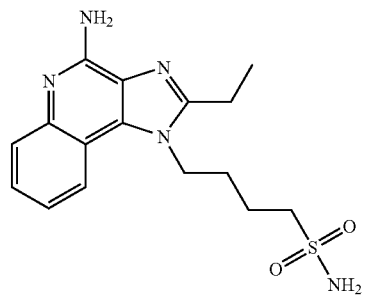 [SMILES: CCc1nc2c(N)nc3ccccc3c2n1CCCCS(N)(=O)=O]

N-(4-Methoxybenzyl) 4-(4-amino-2-ethyl-1H-imidazo[4,5-c]quinolin-1-yl)butane-1-sulfonamide (180 mg) was dissolved in trifluoroacetic acid (3 mL) and stirred for 5.5 hours. The reaction mixture was concentrated under reduced pressure. The residue was suspended in methanol (15 mL) and then concentrated under reduced pressure. The residue was triturated with methanol (~3 mL), isolated by filtration, rinsed with methanol (2 mL), and then dried under vacuum to provide 168 mg of a white solid. This solid was triturated with hot dichloromethane (~3 mL), isolated by filtration, washed with dichloromethane (2×2 mL), and then dried under vacuum to provide 124 mg of a solid. This material was recrystallized from methanol (~8 mL evaporated to ~3 mL) to provide 67 mg of 4-(4-amino-2-ethyl-1H-imidazo[4,5-c]quinolin-1-yl)butane-1-sulfonamide trifluoroacetate as a white powder, mp 225-227° C. $^1$H NMR (300 MHz, DMSO-$d_6$): δ 13.43 (br s, 1H), 8.89 (br, 2H), 8.24 (d, J=8.1 Hz, 1H), 7.83 (d, J=8.4 Hz, 1H), 7.72 (t, J=8.0 Hz, 1H), 7.58 (dd, J=1.2, 8.3 Hz, 1H), 6.80 (br s, 2H), 4.62 (t, J=7.3 Hz, 2H), 3.05 (m, 4H), 1.92 (m, 4H), 1.41 (t, J=7.3 Hz, 3H); MS (APCI) m/z: 348 (M+H); Anal. calcd. for $C_{16}H_{21}N_5O_2S \cdot CF_3CO_2H$: C, 46.85; H, 4.81; N, 15.18. Found: C, 46.65; H, 4.82; N, 15.07.

Example 7

N,N-Dimethyl 3-(4-amino-1H-imidazo[4,5-c]quinolin-1-yl)propane-1-sulfonamide

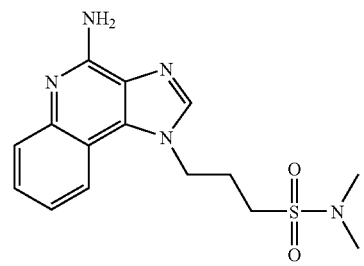 [SMILES: CN(C)S(=O)(=O)CCCn1cnc2c(N)nc3ccccc3c21]

Part A

A solution of sodium dithionite (4.12 g of 85%, 5.0 eq.) in water (16 mL) was added dropwise to a stirred solution of N,N-dimethyl 3-[(3-nitroquinolin-4-yl)amino]propane-1-sulfonamide (1.60 g, 4.72 mmol, 1.0 eq.) in 1/1 acetonitrile/methanol (48 mL). A white precipitate formed during the addition. The reaction mixture was stirred vigorously for 1 hour and then filtered. The filter cake was rinsed with methanol (2×20 mL). The filtrate was concentrated under reduced pressure and then dried under vacuum overnight to provide 4.1 g of crude N,N-dimethyl 3-[(3-aminoquinolin-4-yl)amino]propane-1-sulfonamide as a yellow/orange solid.

Part B

Trimethyl orthoformate (0.62 mL, 1.2 eq.) and pyridine hydrochloride (55 mg, 0.1 eq.) were added sequentially to a stirred suspension of the material from Part A (1.0 eq.) in pyridine. The reaction was heated to 100° C. and stirred for 2 hours. Additional trimethyl orthoformate (1.2 eq.) was added and the reaction mixture was heated for an additional 6 hours. The reaction mixture was allowed to cool to ambient temperature overnight; analysis by TLC indicated that the reaction was complete. The reaction mixture was concentrated under reduced pressure and the residue was partitioned between dichloromethane (100 mL) and water (75 mL). The aqueous layer was back extracted with dichloromethane (50 mL). The combined organics were dried over magnesium sulfate and concentrated under reduced pressure N,N-dimethyl 4-(2-ethyl-1H-imidazo[4,5-c]quinolin-1-yl)butane-1-sulfonamide to provide a yellow foam. This material was purified by HPFC (silica gel eluting sequentially with 0-10% methanol in chloroform for 10 column volumes and 10% methanol in chloroform for 5 column volumes). The resulting material was reconcentrated from acetonitrile then dried under vacuum overnight to provide 1.26 g of N,N-dimethyl 3-(1H-imidazo[4,5-c]quinolin-1-yl)propane-1-sulfonamide as an orange foam.

Part C

3-Chloroperoxybenozic acid (1.17 g of 77% max, 1.2 eq.) was added to a stirred solution of the material from Part B (1.0 eq) in chloroform (20 mL). After 1 hour concentrated ammonium hydroxide (2 mL) and tosyl chloride (943 mg, 1.25 eq.) were added with vigorous stirring. A white precipitate formed after 10 minutes; analysis by TLC indicated that the reaction was complete. After 1 hour the reaction mixture was filtered and the filter cake was rinsed with chloroform (2×15 mL). The filtrate was washed with water (20 mL). The aqueous was back extracted with chloroform (2×25 mL). The combined organics were dried over magnesium sulfate and concentrated under reduced pressure to provide 1.5 g of a brown foam. The foam was triturated with methanol (10-15 mL), isolated by filtration, rinsed with methanol (3×4 mL), and dried under vacuum at 100° C. to provide 435 mg of a white solid. This material was slurried with methanol (3 mL) containing several drops of 10% aqueous sodium hydroxide, isolated by filtration, rinsed with methanol (2×2 mL), and dried under vacuum [0.10 Torr (13 Pa)] at 110° C. for 6 hours to provide 330 mg of N-methyl 3-(4-amino-1H-imidazo[4,5-c]quinolin-1-yl)propane-1-sulfonamide as a white powder, mp 155-157° C. $^1$H NMR (300 MHz, DMSO-$d_6$): δ 8.19 (s, 1H), 8.11 (d, J=7.5 Hz, 1H), 7.63 (dd, J=8.3, 0.8 Hz, 1H), 7.46 (m, 1H), 7.27 (m, 1H), 6.59 (br s, 2H), 4.72 (t, J=7.2 Hz, 2H), 3.19 (t, J=7.6 Hz, 2H), 2.74 (s, 6H), 2.27 pentet, J=7.4 Hz, 2H); MS (APCI) m/z 334 (M+H)+; Anal. calcd for $C_{15}H_{19}N_5O_2S$: C, 54.04; H, 5.74; N, 21.01. Found: C, 53.71; H, 6.06; N, 20.96.

Example 8

N-(4-Methoxyphenyl) 4-(4-amino-2-ethoxymethyl-1H-imidazo[4,5-c]quinolin-1-yl)butane-1-sulfonamide

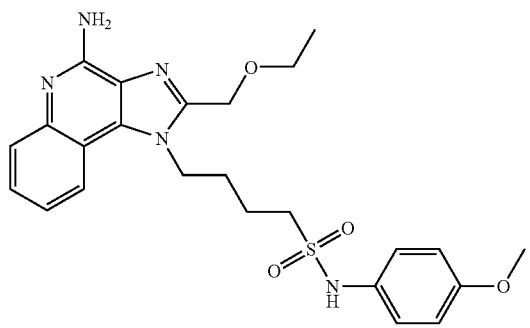 [SMILES: CCOCc1nc2c(N)nc3ccccc3c2n1CCCCS(=O)(=O)Nc1ccc(OC)cc1]

Part A

A solution of thionyl chloride (49.6 g, 1.1 eq.) in dichloromethane (100 mL) was added dropwise with stirring to a chilled (0°) suspension of 4-[(3-nitroquinolin-4-yl)amino]butanol (99 g, 379 mmol, 1 eq.) in dichloromethane (900 mL). The reaction mixture was stirred at ambient temperature overnight and then the pH was adjusted to pH 10 by adding aqueous potassium carbonate (6M). The layers were separated and the aqueous layer was extracted with dichloromethane (4×100 mL). The combined organics were washed with brine, dried over magnesium sulfate, and then concentrated under reduced pressure to provide crude product. This material was purified by chromatography (silica gel eluting with 7% methanol in dichloromethane to provide ~96 g of N-(4-chlorobutyl)-3-nitroquinolin-4-amine.

Part B

A solution of sodium dithionite (3.00 g, 5.0 eq) in water (11 mL) was added dropwise to a stirred suspension of N-(4-chlorobutyl)-3-nitroquinolin-4-amine (964 mg, 3.45 mmol, 1.0 eq.) in ethanol (34 mL). A precipitate formed during the addition. After 45 minutes the reaction mixture was filtered and the filter cake was rinsed with ethanol (3×12 mL). The filtrate was concentrated under reduced pressure and the residue was partitioned between dichloromethane (150 mL) and 50% sodium bicarbonate (60 mL). The organic layer was washed with 50% sodium bicarbonate (60 mL), dried over magnesium sulfate, and then concentrated under reduced pressure to provide 0.45 g of $N^4$-(4-chlorobutyl)quinoline-3,4-diamine as a yellow semisolid.

Part C

Ethoxyacetyl chloride (243 mg, 1.1. eq.) was added dropwise with stirring to a chilled (0°) solution of the material from Part B (1.0 eq.) in dichloromethane (9 mL). The reaction mixture was stirred for 5 minutes then allowed to warm to ambient temperature and stirred for 1 hour. The reaction mixture was concentrated under reduced pressure to provide crude N-[4-(4-chlorobutyl)aminoquinolin-3-yl]-2-ethoxyacetamide hydrochloride as a yellow oil.

Part D

Aqueous sodium hydroxide (1.28 mL of 2M, 1.5 eq.) was added to a stirred solution of the material from Part C (1.0 eq.) in ethanol (17 mL). The reaction mixture was heated at 60-70° C. for 30 minutes at which time analysis by high performance liquid chromatography (HPLC) indicated that the reaction was complete. The reaction mixture was allowed to cool to ambient temperature over the weekend and then concentrated under reduced pressure. The residue was combined with material from another run and then partitioned between ethyl acetate (120 mL) and water (40 mL). The organic layer was dried over magnesium sulfate and concentrated under reduced pressure to provide 0.55 g of a yellow oil. This material was purified by HPFC (silica gel eluting with a gradient from 100% ethyl acetate to 10% methanol in ethyl acetate) to provide 1-(4-chlorobutyl)-2-ethoxymethyl-1H-imidazo[4,5-c]quinoline as a yellow oil.

Part E

Potassium thioacetate (2.95 g, 1.1 eq.) was added in a single portion to a stirred solution of 1-(4-chlorobutyl)-2-ethoxymethyl-1H-imidazo[4,5-c]quinoline (7.46 g, 23.5 mmol, 1.0 eq.) in DMF (110 mL). The solution was stirred overnight at ambient temperature and then concentrated under reduced pressure. The residue was dissolved in dichloromethane (200 mL), washed sequentially with water (100 mL) and brine (100 mL), dried over magnesium sulfate, and concentrated under reduced pressure to provide 8.06 g of product as a brown solid. The solid was further purified by washing with water and stirring over activated charcoal to provide S-[4-(2-ethoxymethyl-1H-imidazo[4,5-c]quinolin-1-yl)butyl]thioacetate.

Part F

A stirred solution of S-[4-(2-ethoxymethyl-1H-imidazo[4,5-c]quinolin-1-yl)butyl]thioacetate (4.19 g, 11.7 mmol, 1.0 eq.) in methanol (59 mL) was degassed with nitrogen for several minutes. Sodium methoxide (5.90 mL of 25 wt % in methanol, 2.2 eq.) was added and the reaction mixture was degassed for several more minutes. After 1 hour the reaction mixture was concentrated under reduced pressure. The residue was diluted with dichloromethane (150 mL) and water (50 mL); then hydrochloric acid (2M) was added to pH ~7. The layers were separated and the aqueous layer was back extracted with dichloromethane (50 mL). The combined organics were dried over magnesium sulfate and concentrated under reduced pressure to provide 3.72 g of crude product as a yellow oil. This oil was purified by HPFC (silica gel eluting with 0-20% CMA in chloroform for 5 column volumes and then with 20% CMA in chloroform for 5 column volumes) to provide 2.20 g of 4-(2-ethoxymethyl-1H-imidazo[4,5-c]quinolin-1-yl)butane-1-thiol as a yellow oil.

Part G

A solution of sodium chlorate (965 mg, 1.3 eq.) was added dropwise with stirring to a chilled (0° C.) solution of the material from Part F (1.0 eq.) in hydrochloric acid (17 mL of 7M). The reaction mixture was allowed to stir for 90 minutes and then dichloromethane (100 mL) was added. Aqueous potassium carbonate (10 mL of 6M) was added dropwise. The reaction mixture was allowed to warm to ambient temperature and then it was poured into a mixture of dichloromethane (100 mL) and water (50 mL). The pH was adjusted to pH 4 by the addition of aqueous potassium carbonate (6M). The layers were separated and the aqueous layer was back extracted with dichloromethane (50 mL). The combined organics were dried over magnesium sulfate and concentrated under reduced pressure to provide 2.04 g of 4-(2-ethoxymethyl-1H-imidazo[4,5-c]quinolin-1-yl)butane-1-sulfonyl chloride as a yellow foam.

Part H

4-Anisidine (689 mg, 1.2 eq.) was added to a stirred solution of 4-(2-ethoxymethyl-1H-imidazo[4,5-c]quinolin-1-yl)butane-1-sulfonyl chloride (1.78 g, 4.66 mmol, 1.0 eq.) in pyridine (15 mL). The reaction mixture was stirred at ambient temperature for 1 hour and then concentrated under reduced pressure. The residue was dissolved in dichloromethane (350 mL), washed sequentially with water (2×100 mL) and brine (100 mL), dried over magnesium sulfate and concentrated under reduced pressure to provide 1.90 g of crude product as a red oil. The oil was purified by HPFC (silica gel eluting with 0-20% CMA in chloroform for 5 column volumes and then with 20% CMA in chloroform for 7 column volumes) to provide 1.19 g of N-(4-methoxyphenyl) 4-(2-ethoxymethyl-1H-imidazo[4,5-c]quinolin-1-yl)butane-1-sulfonamide as a tan solid.

Part I

3-Chloroperoxybenozic acid (622 mg of 77% max, 1.2 eq.) was added to a stirred solution of N-(4-methoxyphenyl) 4-(2-ethoxymethyl-1H-imidazo[4,5-c]quinolin-1-yl)butane-1-sulfonamide (986 mg, 2.10 mmol, 1.0 eq) in chloroform (21 mL). After 45 minutes analysis by TLC indicated that the oxidation was complete. Concentrated ammonium hydroxide (2 mL) and tosyl chloride (943 mg, 1.25 eq.) were added with vigorous stirring. After 30 minutes analysis by TLC indicated that the reaction was complete. After 1 hour the reaction mixture was partitioned between chloroform (200 mL) and water (60 mL). The aqueous layer was back extracted with chloroform (50 mL). The combined organics were dried over magnesium sulfate and concentrated under reduced pressure to provide 1.38 g of crude product as a brown foam. This material was purified by HPFC (silica gel eluting with 0-25% CMA in chloroform for 12 column volumes and then with 25% CMA in chloroform for 6 column volumes) followed by trituration with chloroform to provide 207 mg of a white solid. This material was dissolved in hot 9/1 methanol/chloroform (400 mL) and then concentrated under reduced pressure to provide 130 mg of N-(4-methoxyphenyl) 4-(4-amino-2-ethoxymethyl-1H-imidazo[4,5-c]quinolin-1-yl)butane-1-sulfonamide as a tan powder, mp 229-230° C. $^1$H NMR (300 MHz, DMSO-$d_6$): δ 9.48 (br s, 1H), 8.01 (d, J=7.9 Hz, 1H), 7.61 (dd, J=1.0, 8.3 Hz, 1H), 7.45 (m, 1H), 7.25 (m, 1H), 7.10 (m, 2H), 6.85 (m, 2H), 6.61 (br s, 2H), 4.75 (s, 2H), 4.57 (t, J=6.8 Hz, 2H), 3.70 (s, 3H), 3.52 (q, J=7.0 Hz, 2H), 3.03 (m, 2H), 1.87 (m, 4H), 1.11 (t, J=7.0 Hz, 3H); MS (APCI) nm/z 484 (M+H)$^+$; Anal. calcd for $C_{24}H_{29}N_5O_4S$: C, 59.61; H, 6.04; N, 14.48. Found: C, 59.43; H, 6.41; N, 14.31.

Example 9

2-Ethoxymethyl-1-[4-(4-morpholine-4-sulfonyl)butyl]-1H-imidazo[4,5-c]quinoline-4-amine

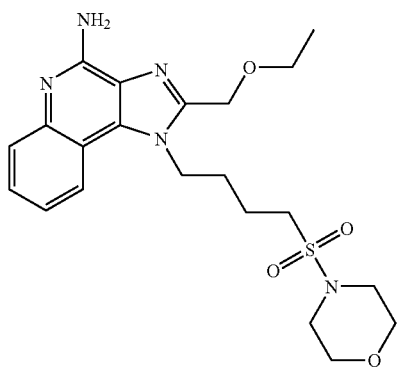 [SMILES: CCOCc1nc2c(N)nc3ccccc3c2n1CCCCS(=O)(=O)N1CCOCC1]

Part A

Morpholine (0.54 mL, 1.2 eq.) was added to a stirred solution of 4-(2-ethoxymethyl-1H-imidazo[4,5-c]quinolin-1-yl) butane-1-sulfonyl chloride (1.95 g, 5.0 mmol, 1.0 eq.) in pyridine (20 mL). The reaction mixture was stirred at ambient temperature for 1.5 hours and then concentrated under reduced pressure. The residue was dissolved in dichloromethane (300 mL) and washed with aqueous 50% sodium bicarbonate. The aqueous layer was back extracted with dichloromethane (100 mL). The combined organics were dried over magnesium sulfate and concentrated under reduced pressure to provide 1.39 g of crude product as a brown oil. The oil was purified by HPFC (silica gel eluting with 0-20% CMA in chloroform for 8 column volumes and then with 20% CMA in chloroform for 5 column volumes) to provide 1.05 g of 2-ethoxymethyl-1-[4-(4-morpholine-4-sulfonyl)butyl]-1H-imidazo[4,5-c]quinoline as a light yellow foam.

Part B

3-Chloroperoxybenozic acid (711 mg of 77% max, 1.2 eq.) was added to a stirred solution of the material from Part A (1.0 eq) in chloroform (24 mL). After 45 minutes concentrated ammonium hydroxide (2.4 mL) and tosyl chloride (573 mg, 1.25 eq.) were added with vigorous stirring. After 10 minutes analysis by TLC indicated that the reaction was complete. After 1 hour the reaction mixture was partitioned between chloroform (100 mL) and water (50 mL) containing 10% sodium hydroxide (3 mL), aqueous pH ~11. The organic layer was dried over magnesium sulfate and concentrated under reduced pressure to provide 1.7 g of crude product as a brown foam. This material was purified by HPFC (silica gel eluting with 0-20% CMA in chloroform for 12 column volumes and then with 20% CMA in chloroform for 6 column volumes) followed by trituration with ethyl acetate to provide 695 mg of a white solid. This material was dissolved in chloroform (200 mL), washed with 10% sodium hydroxide (~15 mL), dried over magnesium sulfate, and concentrated under reduced pressure. The residue was triturated with 10% sodium hydroxide, isolated by filtration, washed with water (2×4 mL), and dried under vacuum to provide 624 mg of a tan solid. This material was purified by HPFC (silica gel eluting with 10-20% CMA in chloroform for 5 column volumes and then with 20% CMA in chloroform for 7 column volumes) to provide 410 mg of a white solid. This material was triturated with ethyl acetate (~7 mL), isolated by filtration, rinsed with ethyl acetate (2×2 mL), and dried under vacuum [0.10 Torr, (13 Pa)] at 60° C. over the weekend to provide 365 mg of 2-ethoxymethyl-1-[4-(4-morpholine-4-sulfonyl)butyl]-1H-imidazo[4,5-c]quinoline-4-amine as a white powder, 206-208° C. $^1$H NMR (300 MHz, DMSO-$d_6$): δ 8.08 (d, J=7.8 Hz, 1H), 7.62 (dd, J=1.0, 8.3 Hz, 1H), 7.45 (m, 1H), 7.27 (m, 1H), 6.59 (br s, 2H), 4.78 (s, 2H), 4.63 (t, J=7.3 Hz, 2H), 3.59 (m, 6H), 3.13 (m, 6H), 2.00 (m, 2H), 1.87 (m, 2H), 1.18 (t, J=7.0

Hz, 3H); MS (APCI) m/z 448 (M+H)$^+$; Anal. calcd for C$_{21}$H$_{29}$N$_5$O$_4$S: C, 56.36; H, 6.53; N, 15.65. Found: C, 56.13; H, 6.62; N, 15.47.

Example 10

N-Methyl 4-(4-amino-2-ethoxymethyl-1H-imidazo[4,5-c]quinolin-1-yl)butane-1-sulfonamide

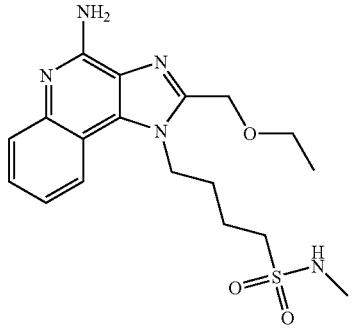 [SMILES: CCOCc1nc2c(N)nc3ccccc3c2n1CCCCS(=O)(=O)NC]

Part A

Methylamine hydrochloride (2.2 eq) was added to a mixture of 4-(2-ethoxymethyl-1H-imidazo[4,5-c]quinolin-1-yl)butane-1-sulfonyl chloride (2 g, 5.23 mmol, 1 eq.) and dichloromethane (20 mL). Aqueous potassium carbonate (2 mL of 6M, 2.2 eq.) was added and the reaction mixture was stirred overnight. The reaction mixture was diluted with water (10 mL). The organic layer was separated, washed sequentially with water (2×10 mL) and brine, dried over magnesium sulfate, and concentrated under reduced pressure to provide 1.39 g of N-methyl 4-(2-ethoxymethyl-1H-imidazo[4,5-c]quinolin-1-yl)butane-1-sulfonamide.

Part B

3-Chloroperoxybenzoic acid (1.08 g of 65%, 1.1 eq.) was added in portions to a solution of the material from Part A in dichloromethane (15 mL). After 45 minutes concentrated ammonium hydroxide (5 mL) was added. Tosyl chloride (1.58 g, 1.1 eq.) was added in portions and the reaction mixture was allowed to stir for 2 hours. The pH was adjusted to pH 8 by the addition of hydrochloric acid (6M). The reaction mixture was filtered to remove solids. The organic layer was concentrated under reduced pressure to provide 2 g of crude product as a black oil. This material was purified by chromatography. The residue was recrystallized from toluene containing activated charcoal then dried under vacuum with heating to provide 0.18 g of N-methyl 4-(4-amino-2-ethoxymethyl-1H-imidazo[4,5-c]quinolin-1-yl)butane-1-sulfonamide as yellow granules, mp 170.0-172.0° C. $^1$H NMR (300 MHz, DMSO d$_6$) δ 8.06 (d, J=7.6 Hz, 1H), 7.61 (dd, J=8.2, 0.9 Hz, 1H), 7.45 (m, 1H), 7.27 (m, 1H), 6.89 (q, J=4.9 Hz, 1H), 6.58 (s, 2H), 4.78 (s, 2H), 4.60 (t, J=7.5 Hz, 2), 3.57 (q, J=7.0 Hz, 2H), 3.07 (t, J=7.5 Hz, 2H), 2.56 (d, J=4.9 Hz, 3H), 1.98 (m, 2H), 1.84 (m, 2H), 1.17 (t, J=7.0 Hz, 3H); MS (APCI) m/z 392 (M+H)$^+$; Anal. Calcd for C$_{18}$H$_{25}$N$_5$O$_3$S: C, 55.22; H, 6.44; N, 17.89. Found: C, 55.16; H, 6.56; N, 17.78.

Example 11

N,N-Dimethyl 4-(4-amino-2-ethoxymethyl-1H-imidazo[4,5-c]quinolin-1-yl)butane-1-sulfonamide

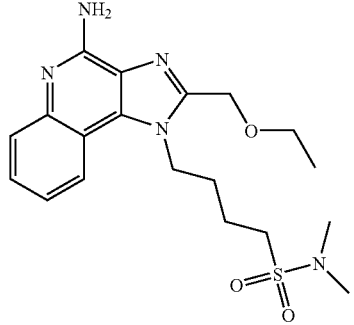 [SMILES: CCOCc1nc2c(N)nc3ccccc3c2n1CCCCS(=O)(=O)N(C)C]

Part A

Dimethylamine hydrochloride (0.65 g, 2.2 eq) was added to a mixture of 4-(2-ethoxymethyl-1H-imidazo[4,5-c]quinolin-1-yl)butane-1-sulfonyl chloride (1.4 g, 3.6 mmol, 1 eq.) and dichloromethane (15 mL). Aqueous potassium carbonate (2 mL of 6M, 2.2 eq.) was added and the reaction mixture was stirred overnight. The reaction mixture was diluted with water (10 mL). The organic layer was separated, washed sequentially with water (2×10 mL) and brine, dried over magnesium sulfate, and concentrated under reduced pressure to provide 1.26 g of N,N-dimethyl 4-(2-ethoxymethyl-1H-imidazo[4,5-c]quinolin-1-yl)butane-1-sulfonamide.

Part B

3-Chloroperoxybenzoic acid (1.23 g of 65%, 1.1 eq.) was added in portions to a solution of the material from Part A in dichloromethane (16 mL). After 30 minutes additional 3-chloroperoxybenzoic acid (0.1 g) was added and the reaction mixture was allowed to stir overnight. Concentrated ammonium hydroxide (5 mL) was added. Tosyl chloride (4.9 g, 1.1 eq.) was added in portions and the reaction mixture was allowed to stir for 2 hours. The reaction mixture was diluted with water (100 mL) and dichloromethane (50 mL). The organic layer was separated and concentrated under reduced pressure to provide 2.6 g of crude product as a brown oil. This material was purified by chromatography (silica gel eluting with 5% methanol in dichloromethane). The product was further purified by HPFC (silica gel eluting with 5% methanol in ethyl acetate) to provide 0.3 g of a solid. This material was recrystallized from toluene and then dissolved in hot methanol. The methanol was removed under vacuum to provide 0.17 g of N,N-dimethyl 4-(4-amino-2-ethoxymethyl-1H-imidazo[4,5-c]quinolin-1-yl)butane-1-sulfonamide as a light yellow powder, mp 173.0-174.0° C. $^1$H NMR (300 MHz, DMSO d$_6$) δ 8.07 (d, J=7.4 Hz, 1H), 7.62 (dd, J=8.3, 1.1 Hz, 1H), 7.45 (m, 1H), 7.27 (m, 1H), 6.59 (s, 2H), 4.78 (s, 2H), 4.62 (t, J=7.5 Hz, 2H), 3.57 (q, J=7.0 Hz, 2H), 3.09 (t, J=7.5 Hz, 2H), 2.74 (s, 6H), 1.99 (m, 2H), 1.86 (m, 2H), 1.17 (t, J=6.9 Hz, 3H); MS (APCI) m/z 406 (M+H)+; Anal. Calcd for $C_{19}H_{27}N_5O_3S$: C, 56.28; H, 6.71; N, 17.27. Found: C, 55.90; H, 6.44; N, 17.17.

Example 12

2-Ethoxymethyl-1-[4-(piperidine-1-sulfonyl)butyl]-1H-imidazo[4,5-c]quinoline-4-amine

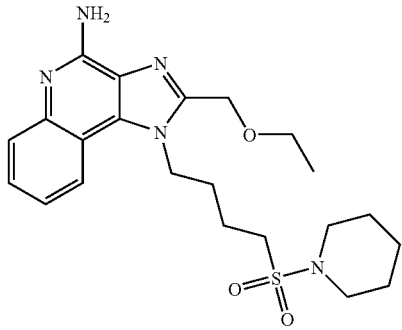 [SMILES: CCOCc1nc2c(N)nc3ccccc3c2n1CCCCS(=O)(=O)N1CCCCC1]

Part A

Piperidine (0.71 mL, 1.1 eq.) was added to a mixture of 4-(2-ethoxymethyl-1H-imidazo[4,5-c]quinolin-1-yl)butane-1-sulfonyl chloride (2.5 g, 6.5 mmol, 1 eq.) and dichloromethane (25 mL). Aqueous potassium carbonate (2 mL of 6M, 2.2 eq.) was added and the reaction mixture was stirred for 2 days. The organic layer was separated and concentrated under reduced pressure to provide 2.4 g of crude product as a brown oil. The oil was purified by HPFC (silica gel eluting with 10% CMA in chloroform) to provide 2 g of 2-ethoxymethyl-1-[4-(piperidine-1-sulfonyl)butyl]-1H-imidazo[4,5-c]quinoline.

Part B

3-Chloroperoxybenzoic acid (1.35 g of 65%, 1.1. eq.) was added to a solution of the material from Part A (1.0 eq.) in chloroform (20 mL). The reaction mixture was stirred until analysis by HPLC indicated that the oxidation was complete. Concentrated ammonium hydroxide (6 mL) was added and a precipitate formed. Tosyl chloride (1.05 g, 1.2 eq.) was added in portions with vigorous stirring. The reaction mixture was stirred until analysis indicated that it was complete. The reaction mixture was diluted with dichloromethane (50 mL). The layers were separated and the aqueous layer was extracted with dichloromethane (3×30 mL). The combined organics were washed sequentially with water and brine, dried over magnesium sulfate, and concentrated under reduced pressure to provide 0.6 g of a brown oil. The oil was purified by HPFC (silica gel eluting with a gradient of 10-18% CMA in chloroform, 1200 mL total) followed by recrystallization from 1,2-dichloroethane to provide 80 mg of 2-ethoxymethyl-1-[4-(piperidine-1-sulfonyl)butyl]-1H-imidazo[4,5-c]quinoline-4-amine as a white powder, mp 185.0-188.0° C. $^1$H NMR (300 MHz, DMSO $d_6$) δ 8.07 (d, J=7.7 Hz, 1H), 7.61 (dd, J=8.3, 1.1 Hz, 1H), 7.45 (m, 1H), 7.26 (m, 1H), 6.61 (s, 2H), 4.78 (s, 2H), 4.62 (t, J=7.3 Hz, 2H), 3.57 (q, J=7.0 Hz, 2H), 3.08 (m, 6H), 1.98 (m, 2H), 1.84 (m, 2H), 1.48 (m, 6H), 1.17 (t, J=7.0 Hz, 3H); MS (APCI) m/z 446 (M+H)+; Anal. Calcd for $C_{22}H_{31}N_5O_3S$: C, 59.30; H, 7.01; N, 15.72. Found: C, 59.05; H, 7.35; N, 15.62.

Example 13

N-Cyclohexyl 4-(4-amino-2-ethoxymethyl-1H-imidazo[4,5-c]quinolin-1-yl)butane-1-sulfonamide

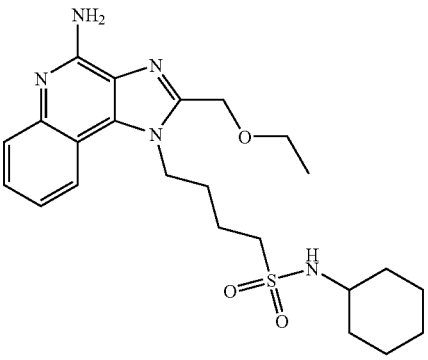 [SMILES: CCOCc1nc2c(N)nc3ccccc3c2n1CCCCS(=O)(=O)NC1CCCCC1]

Part A

Cyclohexylamine (1.48 g, 2.2 eq.) was added to a mixture of 4-(2-ethoxymethyl-1H-imidazo[4,5-c]quinolin-1-yl)butane-1-sulfonyl chloride (2.6 g, 6.8 mmol, 1 eq.) and dichloromethane (25 mL). Aqueous potassium carbonate (2 mL of 6M, 2.2 eq.) was added and the reaction mixture was stirred for 2 hours. The reaction mixture was diluted with water (10 mL) and dichloromethane (25 mL). The organic layer was separated, washed sequentially with water (2×10 mL) and brine, dried over magnesium sulfate, and concentrated under reduced pressure. The residue was purified by HPFC (silica gel eluting with 2% methanol in chloroform) to provide 2 g of N-cyclohexyl 4-(2-ethoxymethyl-1H-imidazo[4,5-c]quinolin-1-yl)butane-1-sulfonamide.

Part B

3-Chloroperoxybenzoic acid (2 g of 65%, 1.1. eq.) was added to a solution of the material from Part A (1.0 eq.) in dichloromethane (20 mL). The reaction mixture was stirred for 1 hour. Concentrated ammonium hydroxide (6 mL) was added. Tosyl chloride (1.03 g, 1.2 eq.) was added in portions with vigorous stirring and the reaction mixture was allowed to stir for 4 hours. The pH was adjusted to pH 8 by the addition of hydrochloric acid (6M). The reaction mixture was filtered to remove solids. The organic layer was concentrated under reduced pressure to provide 2.2 g of crude product as a light brown oil. The oil was purified by HPFC (silica gel eluting with 3% CMA in chloroform) followed by recrystallization from ethanol to provide 0.88 g of N-cyclohexyl 4-(4-amino-2-ethoxymethyl-1H-imidazo[4,5-c]quinolin-1-yl)butane-1-sulfonamide as a light yellow powder, mp 197.0-198.0° C. $^1$H NMR (300 MHz, DMSO $d_6$) δ 8.04 (d, J=7.8 Hz, 1H), 7.62 (dd, J=8.2, 0.9 Hz, 1H), 7.45 (dd, J=7.8, 0.7, Hz, 1H), 7.26 (dd, J=8.0, 1.0 Hz, 1H), 7.03 (d, J=7.6 Hz, 1H), 6.59 (s, 2H), 4.78 (s, 2H), 4.60 (t, J=7.4 Hz, 2H), 3.56 (q, J=7.0 Hz, 2H), 3.04 (t, J=7.5 Hz, 3H), 1.98 (m, 2H), 1.79 (m, 4H), 1.63 (m, 2H), 1.50 (m, 1H), 1.17 (t, J=6.9 Hz, 3H), 1.13 (m, 5H); MS (APCI) m/z 460 (M+H)+; Anal. Calcd for $C_{23}H_{33}N_5O_3S$: C, 60.11; H, 7.24; N, 15.24. Found: C, 59.83; H, 7.07; N, 15.06.

Example 14

N-Butyl 4-(4-amino-2-ethoxymethyl-1H-imidazo[4,5-c]quinolin-1-yl)butane-1-sulfonamide

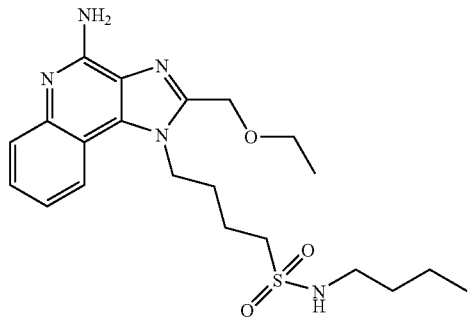 [SMILES: CCCCNS(=O)(=O)CCCCn1c(COCC)nc2c(N)nc3ccccc3c21]

Part A

Butylamine (0.71 mL, 1.1 eq.) was added to a mixture of 4-(2-ethoxymethyl-1H-imidazo[4,5-c]quinolin-1-yl)butane-1-sulfonyl chloride (2.5 g, 6.5 mmol, 1 eq.) and dichloromethane (25 mL). Aqueous potassium carbonate (2.0 mL of 6M, 2.2 eq.) was added and the reaction mixture was stirred overnight. The organic layer was decanted away from the salts and concentrated under reduced pressure. The residue was purified by HPFC (silica gel eluting with 2% methanol in chloroform) to provide 2 g of N-butyl 4-(2-ethoxymethyl-1H-imidazo[4,5-c]quinolin-1-yl)butane-1-sulfonamide.

Part B

3-Chloroperoxybenzoic acid (1.39 g of 65%, 1.1. eq.) was added to a solution of the material from Part A (1.0 eq.) in chloroform (20 mL). The reaction mixture was stirred for 2 hours then additional 3-chloroperoxybenzoic acid (0.1 eq.) was added and the reaction mixture was stirred overnight. Concentrated ammonium hydroxide (6 mL) was added and a precipitate formed. Tosyl chloride (1.14 g, 1.2 eq.) was added in portions with vigorous stirring. The reaction mixture was stirred for 4 hours and then diluted with dichloromethane (60 mL) and water (20 mL). The organic layer was washed sequentially with 10% sodium hydroxide and brine, dried over magnesium sulfate, and concentrated under reduced pressure to provide 1.8 g of crude product as a foam. The foam was purified by HPFC (silica gel eluting with 14% CMA in chloroform) to provide a pale yellow solid. This material was recrystallized from ethanol and dried under vacuum at 50° C. for 4 hours to provide 0.6 g of N-butyl 4-(4-amino-2-ethoxymethyl-1H-imidazo[4,5-c]quinolin-1-yl)butane-1-sulfonamide as a white powder, mp 148.0-149.0° C. $^1$H NMR (300 MHz, DMSO $d_6$) δ 8.05 (d, J=8.0 Hz, 1H), 7.61 (dd, J=8.3, 1.0 Hz, 1H), 7.45 (m, 1H), 7.27 (m, 1H), 7.02 (t, J=5.9 Hz, 1H), 6.61 (br s, 2H), 4.78 (s, 2H), 4.60 (t, J=7.5 Hz, 2H), 3.56 (q, J=7.0 Hz, 2H), 3.05 (t, J=7.5 Hz, 2H), 2.88 (q, J=6.5 Hz, 2H), 1.97 (m, 2H), 1.84 (m, 2H), 1.40 (m, 2H), 1.29 (m, 2H), 1.17 (t, J=7.0 Hz, 3H), 0.85 (t, J=7.2 Hz, 3H); MS (APCI) m/z 434 (M+H)+; Anal. Calcd for $C_{21}H_{31}N_5O_3S$: C, 58.17; H, 7.21; N, 16.15. Found: C, 58.23; H, 7.28; N, 16.16.

Example 15

N,N-Dimethyl 3-[2-(4-amino-2-ethoxymethyl-1H-imidazo[4,5-c]quinolin-1-yl)ethoxy]propane-1-sulfonamide

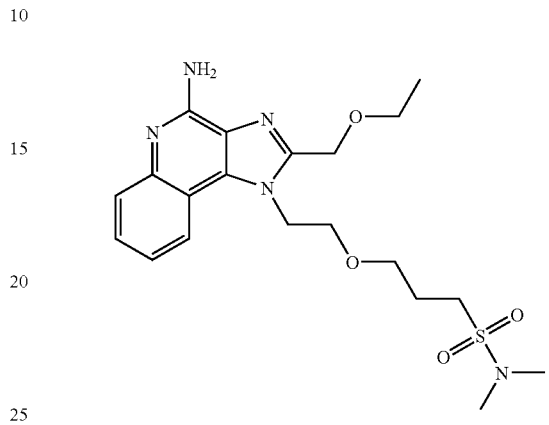

Part A

Triethylamine (46.8 mL, 3.5 eq.) and 4-chloro-3-nitroquinoline (20.0 g, 95.9 mmol, 1.0 eq) were added sequentially to a stirred mixture of 3-(2-aminoethoxy)propanol (29.9 g, 2.0 eq.) and dichloromethane (320 mL). The reaction mixture was stirred for 1 hour at which time analysis by TLC showed that all of the starting material had been consumed. The reaction mixture was diluted with dichloromethane (250 mL) and washed with water (300 mL). The organic layer was dried over magnesium sulfate and concentrated under reduced pressure to provide 32 g of crude product as a yellow oil. The oil was dissolved in chloroform and filtered through a plug of silica gel (300 g) eluting sequentially with chloroform (100 mL) and 2/98 methanol/chloroform (2 L) to provide 25.78 g of 3-{2-[(3-nitroquinolin-4-yl)amino]ethoxy}propanol as a yellow solid.

Part B

Thionyl chloride (3.43 mL, 1.1. eq.)) was added dropwise to a mixture of 3-{2-[(3-nitroquinolin-4-yl)amino]ethoxy}propanol (12.46 g, 42.77 mmol, 1.0 eq.) in dichloromethane (143 mL). A solution resulted and it was stirred for 20 hours. The reaction mixture was diluted with dichloromethane (250 mL) and then quenched with 50% sodium bicarbonate (~250 mL). The organic layer was dried over magnesium sulfate and concentrated under reduced pressure to provide 9.39 g of N-[2-(3-chloropropoxy)ethyl]-3-nitroquinolin-4-amine as a yellow oil which slowly solidified.

Part C

Acetonitrile (50 mL) was added with stirring to a suspension of the material from Part B (1.0 eq.) in warm ethanol (100 mL) to provide a solution. A solution of sodium dithionite (26.30 g of 85%, 5.0 eq.) in water (100 mL) was added. An exotherm was observed (37° C.) and a white precipitate formed. The reaction mixture was stirred vigorously for 30 minutes and then filtered. The filter cake was washed with acetonitrile (2×30 mL). The filtrate was concentrated under reduced pressure. The residue was partitioned between dichloromethane (350 mL) and aqueous saturated sodium bicarbonate (200 mL); aqueous pH ~7). The aqueous was back extracted with dichloromethane (4×75 mL). The combined organics were dried over magnesium sulfate and concentrated under reduced pressure to provide 7.28 g of N⁴-[2-(3-chloropropoxy)ethyl]quinoline-3,4-diamine as a yellow oil.

Part D

Ethoxyacetyl chloride (2.93 mL, 1.1 eq.) was added dropwise to a stirred solution of the material from Part C (1.0 eq.) in dichloromethane (130 mL). After 1 hour the reaction mixture was concentrated under reduced pressure to provide N-{4-[2-(3-chloropropoxy)ethylamino]quinoline-3-yl}-2-ethxoyacetamide as a yellow foam.

Part E

Sodium hydroxide (19.5 mL of 2M, 1.5 eq.) was added to a stirred solution of the material from Part D in ethanol (130 mL). The reaction mixture was warmed to 50° C. and stirred for 1.5 hours at which time analysis by TLC indicated that the reaction was complete. The reaction mixture was cooled to ambient temperature and then concentrated under reduced pressure. The residue was partitioned between dichloromethane (250 mL) and water (75 mL). The aqueous was back extracted with dichloromethane (50 mL). The combined organics were washed with brine (50 mL), dried over magnesium sulfate, and concentrated under reduced pressure to provide 8.40 g of crude product as an oil. The oil was purified by HPFC (silica gel eluting with 0-20% CMA in chloroform for 5 column volumes and then 20% CMA in chloroform for 4 column volumes) to provide 7.64 g of 1-[2-(3-chloropropoxy)ethyl]-2-ethoxymethyl-1H-imidazo[4,5-c]quinoline as a yellow oil.

Part F

Potassium thioacetate (1.01 g, 1.1 eq.) was added to a stirred solution of 1-[2-(3-chloropropoxy)ethyl]-2-ethoxymethyl-1H-imidazo[4,5-c]quinoline (2.80 g, 8.05 mmol, 1.0 eq.) in DMF (16 mL). The resulting suspension was stirred vigorously overnight. Additional potassium thioacetate (0.1 eq.) was added and the reaction mixture was stirred for another 2 hours. The reaction mixture was concentrated under reduced pressure. The residue was diluted with dichloromethane (250 mL) and washed sequentially with water (75 mL) and brine (100 mL). The organic layer was dried over magnesium sulfate and concentrated under reduced pressure to provide 3.07 g of S-{3-[2-(2-ethoxymethyl-1H-imidazo[4,5-c]quinolin-1-yl)ethoxy}propyl thioacetate as a light yellow solid.

Part G

A stirred solution of the material from Part F (1.0 eq.) in methanol (40 mL) was degassed with nitrogen for a few minutes. Sodium methoxide (4.0 mL of 25 wt % in methanol, 2.2 eq.) was added and the degassing was continued for a few more minutes. After 1 hour the reaction mixture was concentrated under reduced pressure. The residue was diluted with dichloromethane (200 mL) and water (100 mL) and the pH was adjusted to pH~7 with 2M hydrochloric acid. The layers were separated and the aqueous layer was back extracted with dichloromethane (50 mL). The combined organics were dried over magnesium sulfate and concentrated under reduced pressure to provide 2.80 g of crude product as a yellow oil. The oil was purified by HPFC (silica gel eluting with 0-20% CMA in chloroform over 5 column volumes then with 20% CMA in chloroform for 5 column volumes) to provide 2.39 g of 3-[2-(2-ethoxymethyl-1H-imidazo[4,5-c]quinolin-1-yl)ethoxy]propane-1-thiol as a yellow oil.

Part H

A solution of sodium chlorate (953 mg, 1.3 eq.) in water (1.5 mL) was added dropwise over a period of ~30 seconds to a chilled (0° C.) solution of the material from Part G (1.0 eq) in hydrochloric acid (17 mL of 7M). The reaction mixture was stirred for 90 minutes and then degassed with nitrogen for a few minutes. Dichloromethane (60 mL) was added followed by the dropwise addition of aqueous potassium carbonate (10 mL of 6M). The reaction mixture was allowed to warm to ambient; the aqueous layer was pH~2. The reaction mixture was poured into dichloromethane (150 mL) and water (60 mL) and the pH was adjusted to pH 4 with 6M potassium carbonate. The layers were separated and the aqueous layer was back extracted with dichloromethane (50 mL). The combined organics were dried over magnesium sulfate and concentrated under reduced pressure to provide 2.25 g of 3-[2-(2-ethoxymethyl-1H-imidazo[4,5-c]quinolin-1-yl)ethoxy]propane-1-sulfonyl chloride as a light yellow oil.

Part I

Dimethylamine hydrochloride (935 mg, 2.1 eq.) was added to a stirred solution of the material from Part H (1.0 eq.) in dichloromethane (27 mL). Aqueous potassium carbonate (2.0 mL of 6M, 2.2 eq.) was added and a white precipitate formed. Analysis by TLC indicated that the reaction was complete in 10 minutes. After 1 hour the reaction mixture was diluted with dichloromethane (125 mL) and washed with water (40 mL). The organic layer was dried over magnesium sulfate and concentrated under reduced pressure to provide 2.03 g of crude product as a yellow oil. The oil was purified by HPFC (silica gel eluting with 0-20% CMA in chloroform over 9 column volumes then with 20% CMA in chloroform for 4 column volumes) to provide 1.46 g of N,N-dimethyl 3-[2-(2-ethoxymethyl-1H-imidazo[4,5-c]quinoline-1-yl)ethoxy]propane-1-sulfonamide as a yellow oil.

Part J

3-Chloroperoxybenzoic acid (1.02 g of 70%, 1.2 eq.) was added to a stirred solution of the material from Part I in chloroform (17 mL). After 1 hour concentrated ammonium hydroxide (3 mL) and tosyl chloride (822 mg, 1.25 eq.) were added sequentially with vigorous stirring. After 10 minutes analysis by TLC indicated that the reaction was nearly complete. After 1 hour the reaction mixture was partitioned between chloroform (100 mL) and water (50 mL) containing 10% sodium hydroxide (3 mL); aqueous pH~11. The organic layer was dried over magnesium sulfate and concentrated under reduced pressure to provide 1.7 g of crude product as a brown foam. The foam was purified by HPFC (silica gel eluting with 0-20% CMA in chloroform over 12 column volumes then with 20% CMA in chloroform over 6 column volumes) to provide 0.847 g of a light brown foam. The foam was warmed in hexanes (~15-20 mL) until the foam started to melt. An equal volume of dichloromethane was added with swirling until solids formed. The mixture was triturated until all of the oily material was solidified. The solids were isolated by filtration, rinsed with 3/1 hexanes/dichloromethane (2×3 mL), and dried under vacuum [0.1 Torr (13 Pa.)] at 40° C. for 3 days to provide 614 mg of N,N-dimethyl 3-[2-(4-amino-2-ethoxymethyl-1H-imidazo[4,5-c]quinoline-1-yl)ethoxy]propane-1-sulfonamide as a white powder, mp 61-64° C. $^1$H NMR (300 MHz, DMSO-$d_6$): δ 8.13 (d, J=7.6 Hz, 1H), 7.61 (dd, J=1.0, 8.3 Hz, 1H), 7.44 (m, 1H), 7.24 (m, 1H), 6.57 (br s, 2H), 4.83 (t, J=5.3 Hz, 2H), 4.79 (s, 2H), 3.87 (t, J=5.4 Hz, 2H), 3.56 (q, J=7.0 Hz, 2H), 3.42 (t, J=6.1 Hz, 2H), 2.79 (m, 2H), 2.63 (s, 6H), 1.75 (m, 2H), 1.17 (t, J=7.0 Hz, 3H); MS (APCI) m/z 436 (M+H)+; Anal. calcd for $C_{20}H_{29}N_5O_4S$: C, 55.15; H, 6.71; N, 16.08. Found: C, 54.94; H, 7.00; N, 16.00.

Example 16

N-Methyl 5-(4-amino-2-ethoxymethyl-1H-imidazo[4,5-c]quinolin-1-yl)pentane-1-sulfonamide

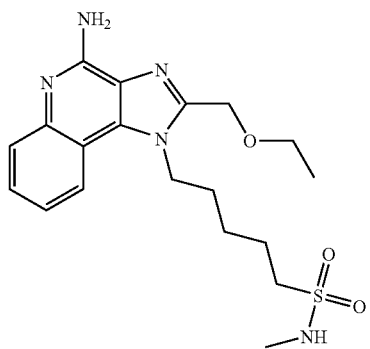 [SMILES: CCOCc1nc2c(N)nc3ccccc3c2n1CCCCCS(=O)(=O)NC]

Part A

Triethylamine (26.68 g, 1.1 eq.) was added to a suspension of 4-chloro-3-nitroquinoline (50 g, 240 mmol, 1.0 eq.) in dichloromethane (500 mL) and all of the solids dissolved. A solution of 5-aminopentanol (27.2 g, 1.1 eq.) in dichloromethane (100 mL) was added dropwise over a period of 30 minutes. The reaction mixture was stirred overnight and then concentrated under reduced pressure to a volume of ~200 mL. Ice water was added and the mixture was triturated for about an hour. Hydrochloric acid (10%) was added to lower the pH from 10 to ~7 and a precipitate formed. The mixture was stirred for about 1 hour. The solid was isolated by filtration and air dried to provide 59 g of 5-[(3-nitroquinolinyl)amino]pentanol.

Part B

A solution of thionyl chloride (20 mL, 1.1 eq) in dichloromethane (50 mL) was added dropwise with stirring to a chilled (0° C.) suspension of 5-[(3-nitroquinolin-4-yl)amino]pentanol (50.4 g, 183 mmol, 1.0 eq.) in dichloromethane (300 mL). The reaction mixture was stirred for 3 hours and then filtered to remove solids. The pH of the filtrate was adjusted to 7-8 with aqueous 5% sodium carbonate. The layers were separated. The aqueous layer was back extracted with dichloromethane (6×20 mL). The combined organics were washed sequentially with water and brine, dried over magnesium sulfate, and concentrated under reduced pressure to provide 47.4 g of N-(5-chloropentyl)-3-nitroquinolin-4-amine.

Part C

A mixture of the material from Part B, catalyst (5% platinum on carbon), and acetonitrile (1.5 L) was hydrogenated on a Parr apparatus until analysis by TLC indicated that the reaction was complete. The reaction mixture was filtered to remove the catalyst and the filtrate was concentrated under reduced pressure to provide 39.8 g of $N^4$-(5-chloropentyl)quinoline-3,4-diamine as a yellow brown oil.

Part D

Ethoxyacetyl chloride (21.66 g, 1.1 eq.) was added dropwise over a period of 15 minutes to a chilled (0° C.) solution of the material from Part C (1.0 eq.) in dichloromethane (400 mL). The reaction mixture was allowed to warm to ambient temperature overnight and then was concentrated under reduced pressure to provide 51.7 g of N-[4-(5-chloropentyl)aminoquinolin-3-yl]-2-ethoxyacetamide.

Part E

A solution of the material from Part D (1.0 eq.) in ethanol and sodium hydroxide (82 mL of 2M) was heated to 60° C. After 4 hours analysis by HPLC indicated that the reaction was complete and the reaction mixture was concentrated under reduced pressure. The residue was combined with dichloromethane (200 mL) and then filtered to remove solids. The filtrate was concentrated under reduced pressure to provide 45.1 g of 1-(5-chloropentyl)-2-ethoxymethyl-1H-imidazo[4,5-c]quinoline as a dark oil.

Part F

A mixture of the material from Part E (1.0 eq.), potassium thioacetate (18.2 g, 1.1 eq.), and DMF (100 mL) was stirred at ambient temperature overnight. The reaction mixture was partitioned between dichloromethane (3000 mL) and cold water (100 mL). The organic layer was washed with water (8×100 mL). The combined aqueous was back extracted with dichloromethane (50 mL). The combined organics were washed with brine, dried over magnesium sulfate, and concentrated under reduced pressure. The residue was purified by eluting through a plug of silica gel to provide 50 g of S-[5-(2-ethoxymethyl-1H-imidazo[4,5-c]quinoline-1-yl)pentyl]thioacetate as a brown oil.

Part G

A solution of S-[5-(2-ethoxymethyl-1H-imidazo[4,5-c]quinolin-1-yl)pentyl]thioacetate (6.4 g, 17.2 mmol, 1.0 eq.) in methanol (50 mL) was degassed with nitrogen for about 20 minutes. Sodium methoxide (4.1 g of 25 wt % in methanol, 1.1 eq.) was diluted with methanol (20 mL) and similarly degassed. The two solutions were combined and stirred for 1 hour at which time analysis by HPLC indicated that all of the starting material had been consumed. The reaction mixture was concentrated under reduced pressure. The residue was diluted with dichloromethane (50 mL) and water (30 mL) and the pH was adjusted to pH 8 with 6M hydrochloric acid. The layers were separated and the aqueous layer was back extracted with dichloromethane (20 mL). The combined organics were washed with brine, dried over magnesium sulfate, and concentrated under reduced pressure to provide 5.9 g of 5-[2-(2-ethoxymethyl-1H-imidazo[4,5-c]quinolin-1-yl)ethoxy]pentane-1-thiol as a yellow green oil.

Part H

A solution of sodium chlorate (1.67 g, 1.3 eq.) in water (3 mL) was added dropwise to a chilled solution of 5-[2-(2-ethoxymethyl-1H-imidazo[4,5-c]quinolin-1-yl)ethoxy]pentane-1-thiol (4 g, 12 mmol, 1.0 eq.) in hydrochloric acid (50 mL of 6N). After about an hour the reaction mixture was diluted with dichloromethane (120 ml) and then potassium carbonate was added to adjust the aqueous to pH 6. The organic layer was concentrated under reduced pressure to provide 3.5 g of 5-[2-(2-ethoxymethyl-1H-imidazo[4,5-c]quinolin-1-yl)ethoxy]pentane-1-sulfonyl chloride.

Part I

A mixture of the material from Part H (1 eq), methylamine hydrochloride (1.5 g, 2.2. eq.), potassium carbonate (1.53 g, 2.2 eq.) and dichloromethane was stirred overnight. Additional methylamine hydrochloride (1 eq.) and potassium carbonate (1 eq.) were added and the reaction mixture was stirred overnight. The reaction mixture was combined with that from another run and then diluted with sufficient water to dissolve the salts that were present. The organic layer was concentrated under reduced pressure to provide 3.65 g of N-methyl 5-(2-ethoxymethyl-1H-imidazo[4,5-c]quinolin-1-yl)pentane-1-sulfonamide as an oil.

Part J

3-Chloroperoxybenzoic acid (2.61 g of 65%, 1.1 eq.) was added in portions to a stirred solution of the material from Part I (1 eq.) in dichloromethane (20 mL). After 2 hours additional 3-chloroperoxybenzoic acid (0.6 eq) was added and the reaction mixture was stirred for 45 minutes. The reaction mixture was diluted with water (15 mL). The aqueous layer was back extracted with dichloromethane (5 mL). The combined organics were washed with brine, dried over magnesium sulfate, and then concentrated under reduced pressure. Ammonium hydroxide (5 mL of 18M) was added to the residue. Tosyl chloride (2.04 g, 1.2 eq.) was added in portions and the reaction mixture was stirred overnight. The reaction mixture was diluted with dichloromethane (100 mL). The aqueous layer was back extracted with dichloromethane (20 mL). The combined organics were washed sequentially with water and brine, dried over magnesium sulfate, filtered, and then concentrated under reduced pressure to provide a tan solid. The solid was recrystallized from toluene, isolated by filtration, rinsed with toluene, and dried under vacuum overnight to provide 1.7 g of N-methyl 5-(4-amino-2-ethoxymethyl-1H-imidazo[4,5-c]quinolin-1-yl)pentane-1-sulfonamide as yellow granules, mp 175.0-179.0° C. $^1$H NMR (300 MHz, DMSO d$_6$) δ 8.02 (d, J=8.0 Hz, 1H), 7.62 (dd, J=8.3, 0.7 Hz, 1H), 7.45 (t, J=7.5 Hz, 1H), 7.28 (m, 1H), 6.85 (q, J=4.9 Hz, 1H), 6.60 (s, 2H), 4.78 (s, 2H), 4.56 (t, J=7.5 Hz, 2H), 3.56 (q, J=6.9 Hz, 2H), 3.01 (t, J=7.5 Hz, 2H), 2.54 (d, J=4.8 Hz, 3H), 1.89 (m, 2H), 1.70 (m, 2H), 1.58 (m, 2H), 1.16 (t, J=6.9 Hz, 3H); MS (APCI) m/z 406 (M+H)$^+$; Anal. Calcd for C$_{19}$H$_{27}$N$_5$O$_3$S: C, 56.28; H, 6.71; N, 17.27. Found: C, 55.97; H, 6.78; N, 17.10.

Example 17

N,N-Dimethyl 5-(4-amino-2-ethoxymethyl-1H-imidazo[4,5-c]quinolin-1-yl)pentane-1-sulfonamide

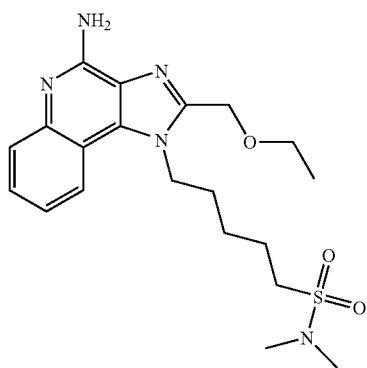 [SMILES: CCOCc1nc2c(N)nc3ccccc3c2n1CCCCCS(=O)(=O)N(C)C]

Part A

Dimethylamine hydrochloride (1.61 g, 2.2 eq.) and a solution of potassium carbonate (1.36 g, 2.2 eq) in water (1 mL) were added sequentially to a solution of 5-[2-(2-ethoxymethyl-1H-imidazo[4,5-c]quinolin-1-yl)ethoxy]pentane-1-sulfonyl chloride (3.5 g, 8.9 mmol, 1 eq) in dichloromethane (60 mL). The reaction mixture was stirred overnight and then diluted with water (10 mL). The organic layer was washed with water and then concentrated under reduced pressure to provide 3.6 g of N,N-dimethyl 5-(2-ethoxymethyl-1H-imidazo[4,5-c]quinolin-1-yl)pentane-1-sulfonamide.

Part B

3-Chloroperoxybenzoic acid (2.38 g of 65%, 1.1 eq.) was added in portions to a stirred solution of the material from Part A (1 eq.) in dichloromethane (20 mL). After 3 hours the reaction mixture was diluted with water (15 mL). The aqueous layer was back extracted with dichloromethane (5 mL). The combined organics were washed with brine, dried over magnesium sulfate, and then concentrated under reduced pressure. Ammonium hydroxide (5 mL of 18M) was added to the residue. Tosyl chloride (1.86 g, 1.2 eq.) was added in portions and the reaction mixture was stirred overnight. The reaction mixture was diluted with dichloromethane (100 mL). The aqueous layer was back extracted with dichloromethane (20 mL). The combined organics were washed sequentially with water and brine, dried over magnesium sulfate, filtered, and then concentrated under reduced pressure to provide a tan solid. The solid was recrystallized from toluene, isolated by filtration, rinsed with toluene, and dried under vacuum overnight to provide 1.7 g of N,N-dimethyl 5-(4-amino-2-ethoxymethyl-1H-imidazo[4,5-c]quinolin-1-yl)pentane-1-sulfonamide as a white powder, mp 138.0-142.0° C. $^1$H NMR (300 MHz, CDCl$_3$) δ 7.93 (dd, J=8.3, 0.7 Hz, 1H), 7.82 (dd, J=8.2, 0.7 Hz, 1H), 7.53 (ddd, J=8.3, 7.2, 1.2 Hz, 1H), 7.35 (m, 1H), 5.38 (s, 2H), 4.80 (s, 2H), 4.59 (t, J=7.8 Hz, 2l), 3.62 (q, J=7.0 Hz, 2H), 2.90 (t, J=7.5 Hz, 2H), 2.85 (s, 6H), 2.04 (m, 2H), 1.91 (m, 2H), 1.67 (m, 2H), 1.25 (s, J=6.9 Hz, 3H); MS (APCI) m/z 420 (M+H)$^+$; Anal. Calcd for C$_{20}$H$_{29}$N$_5$O$_3$S: C, 57.26; H, 6.97; N, 16.69. Found: C, 57.10; H, 7.10; N, 16.58.

Example 18

N-Methyl 4-(4-amino-2-ethoxymethyl-6,7,8,9-tetrahydro-1H-imidazo[4,5-c]quinolin-1-yl)butane-1-sulfonamide

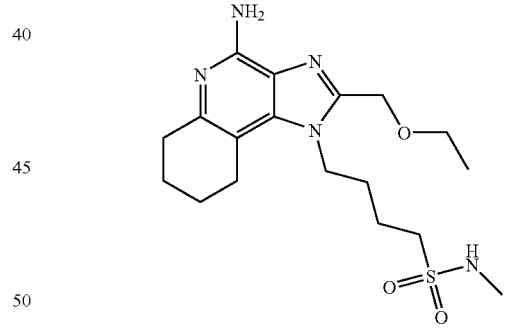

A solution of N-methyl 4-(4-amino-2-ethoxymethyl-1H-imidazo[4,5-c]quinolin-1-yl)butane-1-sulfonamide (1.01 g, 2.5 mmol) in trifluoroacetic acid (2 mL) was combined with a catalytic amount of platinum (IV) oxide and hydrogenated on a Parr apparatus until analysis by HPLC/mass spectroscopy indicated that the reaction was complete. The reaction mixture was filtered through a layer of CELITE filter aid. The filter cake was rinsed with fresh trifluoroacetic acid and the filtrate was concentrated under reduced pressure to provide 0.8 g of crude product as a dark oil. The oil was suspended in hydrochloric acid (5 mL) and stirred for about 1 hour. The pH was adjusted to about 7 with 10% sodium hydroxide. The resulting solid was isolated by filtration, recrystallized from ethanol and then dried under high vacuum at about 78° C. to provide 0.4 g of N-methyl 4-(4-amino-2-ethoxymethyl-6,7,

Example 19

N,N-Dimethyl 4-(4-amino-2-ethoxymethyl-6,7,8,9-tetrahydro-1H-imidazo[4,5-c]quinolin-1-yl)butane-1-sulfonamide

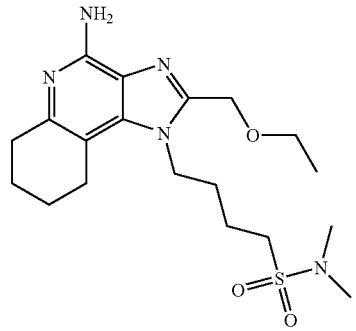 [SMILES: CCOCc1nc2c(N)nc3c(c2n1CCCCS(=O)(=O)N(C)C)CCCC3]

A mixture of N,N-dimethyl 4-(4-amino-2-ethoxymethyl-1H-imidazo[4,5-c]quinolin-1-yl)butane-1-sulfonamide (1.25 g, 3.0 mmol), trifluoroacetic acid (10 mL) and platinum (IV) oxide (1.22 g) was hydrogenated on a Parr apparatus until analysis by LC/mass spectroscopy indicated that the reaction was complete. The reaction mixture was filtered through a layer of CELITE filter aid. The filter cake was rinsed with fresh trifluoroacetic acid (2 mL) and chloroform (20 mL) and the filtrate was concentrated under reduced pressure to provide crude product as an oil. The oil was dissolved in concentrated hydrochloric acid (5 mL) and stirred overnight. The solution was neutralized with 61 potassium carbonate (6 mL), diluted with dichloromethane (25 mL), adjusted to pH 13 with 10% sodium hydroxide, and then stirred for about 2 hours. The organic layer was separated and concentrated under reduced pressure. The residue (0.7 g) was purified by chromatography (silica gel eluting with a gradient of 13% CMA in chloroform to 28% CMA in chloroform over 10.6 column volumes) to provide 0.6 g of a white solid. The white solid was recrystallized from methanol, isolated by filtration, and then dried under high vacuum to provide 0.4 g of N,N-dimethyl 4-(4-amino-2-ethoxymethyl-6,7,8,9-tetrahydro-1H-imidazo[4,5-c]quinolin-1-yl)butane-1-sulfonamide, mp 188-192° C. Anal. calcd. for $C_{18}H_{29}N_5O_3S$: C, 54.66; H, 7.39; N, 17.71. Found: C, 54.42; H, 7.39; N, 17.52.

Example 20

N-(4-Methoxybenzyl) 4-(4-amino-2-ethoxymethyl-1H-imidazo[4,5-c]quinolin-1-yl)butane-1-sulfonamide

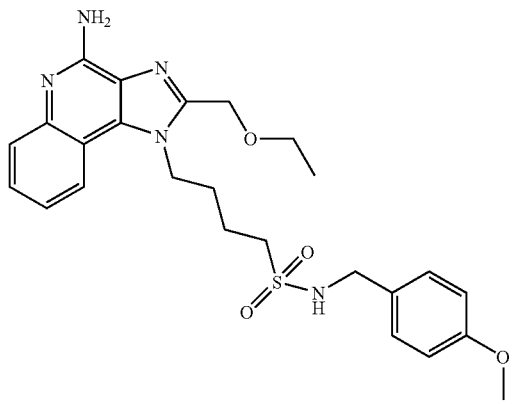 [SMILES: CCOCc1nc2c(N)nc3ccccc3c2n1CCCCS(=O)(=O)NCc1ccc(OC)cc1]

The general procedure of Example 14 was repeated using 4-methoxybenzylamine in lieu of butylamine to provide N-(4-methoxybenzyl) 4-(4-amino-2-ethoxymethyl-1H-imidazo[4,5-c]quinolin-1-yl)butane-1-sulfonamide, mp 101° C. Anal. calcd. for $C_{25}H_{31}N_5O_4S \cdot 0.59H_2O$: C, 59.08; H, 6.38; N, 13.78; Found: C, 59.21; H, 6.74; N, 13.59.

Example 21

4-(4-Amino-2-ethoxymethyl-1H-imidazo[4,5-c]quinolin-1-yl)butane-1-sulfonamide

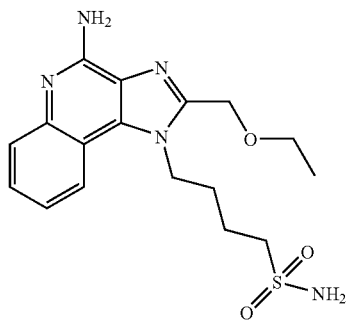 [SMILES: CCOCc1nc2c(N)nc3ccccc3c2n1CCCCS(N)(=O)=O]

A solution of N-(4-methoxybenzyl) 4-(4-amino-2-ethoxymethyl-1H-imidazo[4,5-c]quinolin-1-yl)butane-1-sulfonamide (0.81 g) in trifluoroacetic acid (5 mL) was stirred at ambient temperature until analysis by LC/mass spectroscopy indicated that all of the starting material had been consumed. The reaction mixture was concentrated under reduced pressure and then placed under high vacuum. The residue was suspended in concentrated hydrochloric acid (5 mL) and stirred for about 1 hr. The resulting solid was isolated by filtration, recrystallized from methanol, isolated by filtration, and then dried under high vacuum at 78° C. to provide 0.28 g of 4-(4-amino-2-ethoxymethyl-1H-imidazo[4,5-c]quinolin-1-yl)butane-1-sulfonamide, mp 155-158° C. Anal. calcd. for $C_{17}H_{23}N_5O_3S$: C, 54.09; H, 6.14; N, 18.55 Found: C, 53.86; H, 6.13; N, 18.24.

Example 22

N-(4-Methoxybenzyl) 5-(4-amino-2-ethoxymethyl-1H-imidazo[4,5-c]quinolin-1-yl)pentane-1-sulfonamide

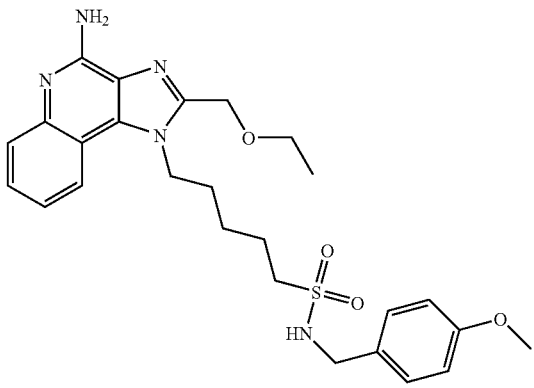 [SMILES: CCOCc1nc2c(N)nc3ccccc3c2n1CCCCCS(=O)(=O)NCc1ccc(OC)cc1]

The general procedure of Example 16 Parts I and J was repeated using 4-methoxybenzylamine in lieu of methylamine to provide N-(4-methoxybenzyl) 5-(4-amino-2-ethoxymethyl-1H-imidazo[4,5-c]quinolin-1-yl)pentane-1-sulfonamide, mp 177-178° C. Anal. calcd. for $C_{26}H_{33}N_5O_4S$: C, 61.04; H, 6.50; N, 13.69 Found: C, 61.07; H, 6.74; N, 13.77.

Example 23

5-(4-Amino-2-ethoxymethyl-1H-imidazo[4,5-c]quinolin-1-yl)pentane-1-sulfonamide

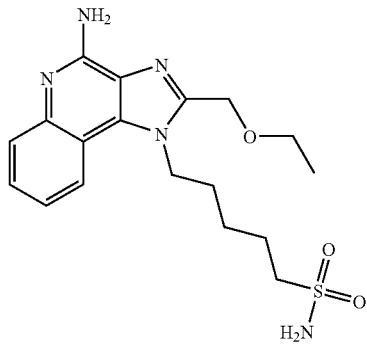 [SMILES: CCOCc1nc2c(N)nc3ccccc3c2n1CCCCCS(N)(=O)=O]

A solution of N-(4-methoxybenzyl) 5-(4-amino-2-ethoxymethyl-1H-imidazo[4,5-c]quinolin-1-yl)pentane-1-sulfonamide (2.3 g) in trifluoroacetic acid (~20 g) was stirred overnight. A portion (~8 mL) was concentrated under reduced pressure. The residue was partitioned between 6M hydrochloric acid (9 mL) and dichloromethane (30 mL). The aqueous layer was chilled in an ice bath and 10% sodium hydroxide was added with stirring to pH 13. The mixture was stirred for about 1 hr and then the pH was adjusted to 7. The resulting precipitate was isolated by filtration, recrystallized from methanol, isolated by filtration, and then dried under high vacuum at 78° C. to provide 0.5 g of 5-(4-amino-2-ethoxymethyl-1H-imidazo[4,5-c]quinolin-1-yl)pentane-1-sulfonamide, mp 176-178° C. Anal. calcd. for $C_{18}H_{25}N_5O_3S$: C, 55.22; H, 6.44; N, 17.89 Found: C, 55.06; H, 6.42; N, 17.84.

Example 24

4-(4-Amino-2-ethoxymethyl-6,7,8,9-tetrahydro-1H-imidazo[4,5-c]quinolin-1-yl)butane-1-sulfonamide

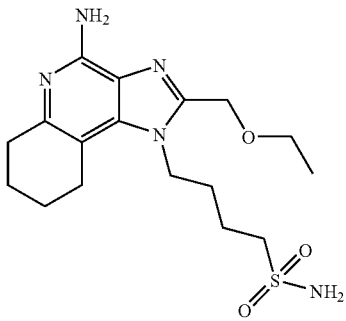 [SMILES: CCOCc1nc2c(N)nc3c(c2n1CCCCS(N)(=O)=O)CCCC3]

A solution of N-(4-methoxybenzyl) 4-(4-amino-2-ethoxymethyl-1H-imidazo[4,5-c]quinolin-1-yl)butane-1-sulfonamide (0.6 g) in trifluoroacetic acid was stirred at ambient temperature until analysis by LC/mass spectroscopy indicated that all of the starting material had been consumed. The solution was combined with platinum (IV) oxide and hydrogenated on a Parr apparatus until analysis by LC/mass spectroscopy indicated that the reaction was complete. The reaction mixture was filtered through a layer of CELITE filter aid. The filter cake was rinsed with fresh trifluoroacetic acid and the filtrate was concentrated under reduced pressure to provide the trifluoroacetate of the product as an oil. This material was converted to the free base using the general method of Example 23, recrystallized sequentially from methanol and then water, and then dried under high vacuum at 91° C. to provide 4-(4-amino-2-ethoxymethyl-6,7,8,9-tetrahydro-1H-imidazo[4,5-c]quinolin-1-yl)butane-1-sulfonamide, mp 224-227° C. Anal. calcd. for $C_{17}H_{27}N_5O_3S$: C, 53.52; H, 7.13; N, 18.36 Found: C, 53.36; H, 7.24; N, 18.06.

Example 25

N,N-Dimethyl 3-(4-amino-2-ethoxymethyl-1H-imidazo[4,5-c]quinolin-1-yl)-2,2-dimethylpropane-1-sulfonamide

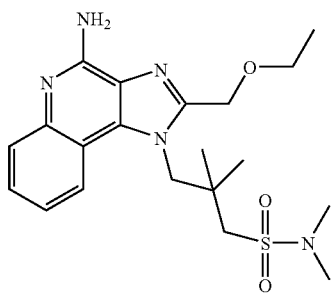 [SMILES: CCOCc1nc2c(N)nc3ccccc3c2n1CC(C)(C)CS(=O)(=O)N(C)C]

Part A

Triethylamine (17.5 mL, 1.3 eq) was added dropwise to a suspension of 4-chloro-3-nitroquinoline (20.14 g, 96.5 mmol, 1.0 eq) in dichloromethane (300 mL). 3-Amino-2,2-dimethylpropanol (10.96 g, 1.1 eq) was added, the reaction mixture was stirred for 45 minutes and then concentrated under reduced pressure. The residue was slurried with water (300 mL) for 1 hr, isolated by filtration, rinsed with water (2×60 mL), and then dried under high vacuum to provide 20.7 g of 2,2-dimethyl-3-[(3-nitroquinolin-4-yl)amino]propanol as a yellow solid.

Part B

A suspension of 2,2-dimethyl-3-[(3-nitroquinolin-4-yl)amino]propanol (1.45 g) and 10% palladium on carbon in ethanol was hydrogenated on a Parr apparatus until analysis by TLC indicated that the reaction was complete. The reaction mixture was filtered through a layer of CELITE filter aid. The filter cake was rinsed with ethanol (3×10 mL). The filtrate was concentrated under reduced pressure. The residue was suspended in toluene (150 mL) and concentrated under reduced pressure to provide 3-[(3-aminoquinolin-4-yl)amino]-2,2-dimethylpropanol.

Part C

Ethoxyacetyl chloride (564 µL, 1.05 eq) was added dropwise to a chilled (0° C.) solution of the material from Part B (1.0 eq) in pyridine (25 mL). The progress of the reaction was monitored by TLC, additional ethoxyacetyl chloride (0.6 eq) was added to drive the reaction to completion. The reaction mixture was allowed to warm to ambient temperature overnight. The reaction mixture was heated at 80° C. for 2 hrs and then at 110° C. for 9 hours. The reaction mixture was cooled to ambient temperature and then concentrated under reduced pressure. The residue was combined with the material obtained from another run and then purified by HPFC (silica gel eluting with 0-40% acetone in chloroform (0.75% ethanol stabilized) over 1 L and then with 40-60% acetone in chloroform over 1.8 L) to provide 1.66 g of 3-(2-ethoxymethyl-1H-imidazo[4,5-c]quinolin-1-yl)-2,2-dimethylpropanol as a clear oily semisolid.

Part D

Tosyl chloride (1.18 g, 1.2 eq) and 4-dimethylaminopyridine (13 mg, 0.02 eq) were added sequentially to a solution of 3-(2-ethoxymethyl-1H-imidazo[4,5-c]quinolin-1-yl)-2,2-dimethylpropanol (1.61 g, 5.14 mmol, 1.0 eq) in pyridine (6 mL). The reaction mixture was stirred at ambient temperature for 20 hrs, quenched with brine (75 mL), and then extracted with ethyl acetate (1×75 mL). The extract was dried over magnesium sulfate, filtered, and then concentrated under reduced pressure. The residue was dissolved in dichloromethane (20 mL), diluted with heptanes (125 mL), concentrated under reduced pressure, and then dried under high vacuum to provide 2.12 g of 3-(2-ethoxymethyl-1H-imidazo[4,5-c]quinolin-1-yl)-2,2-dimethylpropyl p-toluenesulfonate as a light brown oil.

Part E

Sodium hydrosulfide hydrate (1.23 g, 5.0 eq) was added to a solution of the material from Part D (1.0 eq) in ethanol (22 mL). The reaction was heated at 75° C. for 30 hours and then allowed to cool to ambient temperature over the weekend. Analysis by TLC indicated that the reaction was not complete. Additional sodium hydrosulfide hydrate (3 eq) was added and the reaction mixture was heated for an additional 48 hrs. The reaction mixture was concentrated under reduced pressure. The residue was suspended in water (100 mL) and then extracted with dichloromethane (3×100 mL). The combined extracts were dried over magnesium sulfate and then concentrated under reduced pressure to provide 1.23 g of a white foam. This material was purified by HPFC (silica gel eluting with 0-10% CMA in chloroform over 2 column volumes, 10-25% CMA in chloroform over 7 column volumes, 25-35% CMA in chloroform over 1.5 column volumes, and 35% CMA in chloroform over 5 column volumes) to provide 0.87 g of 3-(2-ethoxymethyl-1H-imidazo[4,5-c]quinolin-1-yl)-2,2-dimethylpropane-1-thiol as a clear oil.

Part F

Using the general method of Example 8 Part G, 3-(2-ethoxymethyl-1H-imidazo[4,5-c]quinolin-1-yl)-2,2-dimethylpropane-1-thiol (0.75 g) was oxidized to provide 0.67 g of 3-(2-ethoxymethyl-1H-imidazo[4,5-c]quinolin-1-yl)-2,2-dimethylpropane-1-sulfonyl chloride as an oily yellow foam.

Part G

Using the general method of Example 11 Part A, the material from Part F was reacted with dimethylamine hydrochloride. The crude product was purified by HPFC (silica gel eluting with 0-30% CMA in chloroform for 8 column volumes and then 30% CMA in chloroform for 3 column volumes) to provide 0.36 g of N,N-dimethyl 3-(2-ethoxymethyl-1H-imidazo[4,5-c]quinolin-1-yl)-2,2-dimethylpropane-1-sulfonamide as an off white foam.

Part H

Using the general method of Example 11 Part B, the material form Part G was oxidized and then aminated. The crude product was purified by (silica gel eluting with 0-30% CMA in chloroform for 15 column volumes and then 30% CMA in chloroform for 2 column volumes) to provide 0.19 g of a brown oil. The oil was dissolved in ethanol (8 mL), combined with 7 M hydrochloric acid (65 µL), stirred for 10 minutes and then concentrated to a sticky brown oil. The oil was triturated with hot ethyl acetate to provide a solid, concentrated, triturated with hot acetonitrile (6-7 mL), and then cooled to ambient temperature. The resulting solid was isolated by filtration, rinsed with acetonitrile (3×1 mL), and dried (0.10 Torr (13 Pa) at 50° C. for 3 days; then at 0.12 Torr (16 Pa) at 60° C. for 16 hrs) to provide 133 mg of the hydrochloride salt of N,N-dimethyl 3-(4-amino-2-ethoxymethyl-1H-imidazo[4,5-c]quinolin-1-yl)-2,2-dimethylpropane-1-sulfonamide as a tan powder, mp 193-195° C. Anal. calcd. for $C_{20}H_{29}N_5O_3S \cdot HCl \cdot 0.15H_2O$: C, 52.37; H, 6.66; N, 15.27 Found: C, 52.07; H, 6.75; N, 15.08.

Example 26

N,N-Dimethyl 4-(4-Amino-6,7-dimethyl-2-propyl-1H-imidazo[4,5-c]pyridin-1-yl)butane-1-sulfonamide

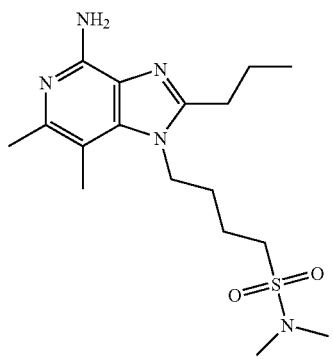

Part A

Under a nitrogen atmosphere, triethylamine (38 mL, 2.0 eq) was added in a single portion to a mixture of 2,4-dichloro-5,6-dimethyl-3-nitropyridine (30.0 g, 136 mmol, 1.0 eq) and N,N-dimethylformamide (DMF, 450 mL). The reaction mixture was stirred for 10 minutes, 4-amino-1-butanol (17.6 mL, 1.4 eq) was added, and the reaction mixture was stirred overnight. The reaction mixture was concentrated under reduced pressure to provide crude product as an oil. The oil was partitioned between chloroform (500 mL) and water/brine (1:1 50 mL). The organic phase was separated, washed with water/brine (1:1 3×30 mL), dried over magnesium sulfate, filtered, and then concentrated under reduced pressure to provide an orange solid. This material was dried under high vacuum at 40° C. and then recrystallized from ethyl acetate/hexanes to provide 23.0 g of 4-(2-chloro-5,6-dimethyl-3-nitropyridin-1-yl)butan-1-ol.

Part B

Under a nitrogen atmosphere, a mixture of 4-(2-chloro-5,6-dimethyl-3-nitropyridin-1-yl)butan-1-ol (24.5 g, 89.5 mmol, 1.0 eq), sodium azide (11.6 g, 2.0 eq.), cerium (III) chloride heptahydrate (16.7 g, 0.5 eq), and acetonitrile/water (9:1 250 mL) was heated at reflux overnight. The reaction mixture was filtered while still hot and the filter cake was rinsed with warm acetonitrile and DMF. The filtrate was concentrated under reduced pressure and then dried under high vacuum at 50° C. for 2 hrs to provide 25 g of crude 4-[(5,6-dimethyl-8-nitrotetraazolo[1,5-a]pyridin-7-yl) amino]butan-1-ol.

Part C

Under a nitrogen atmosphere, thionyl chloride (9.8 mL, 1.5 eq) was added dropwise with stirring to a mixture of the material from Part B and chloroform (500 mL). The reaction mixture was heated at a vigorous reflux for 3.5 hrs, cooled to ambient temperature, and then diluted with water (200 mL). The phases were separated and the aqueous phase was extracted with chloroform (3×100 mL). The combined organics were washed with water (3×50 mL), dried over magnesium sulfate, filtered, concentrated under reduced pressure, and then dried under high vacuum to provide 30 g of crude N-(4-chlorobutyl)-5,6-dimethyl-8-nitrotetraazolo[1,5-a]pyridin-7-amine as an orange oil.

Part D

The material from Part C was combined in a pressure vessel with catalyst (2.5 g of 5% platinum on carbon), and ethyl acetate (500 mL). The reaction mixture was placed under hydrogen pressure ((30 psi, $(2.1 \times 10^5$ Pa)) for 2 days. Analysis by HPLC indicated that the reaction was not complete. More catalyst (~1.3 g) was added and the reaction was continued until analysis by HPLC indicated that the reaction was complete. The reaction mixture was filtered through a layer of CELITE filter aid and the filter cake was washed with chloroform. The filtrate was concentrated under reduced pressure to provide 20.0 g of $N^7$-(4-chlorobutyl)-5,6-dimethyltetraazolo[1,5-a]pyridine-7,8-diamine as an off white solid.

Part E

Under a nitrogen atmosphere, pyridine hydrochloride (1.62 g, 0.375 eq) and trimethyl orthobutyrate (6.5 mL, 1.1. eq) were added sequentially to a suspension of $N^7$-(4-chlorobutyl)-5,6-dimethyltetraazolo[1,5-a]pyridine-7,8-diamine (10.0 g, 37.2 mmol, 1 eq) in toluene (250 mL). The reaction mixture was heated at reflux for 1 hour, allowed to stand at ambient temperature over the weekend, and then concentrated under reduced pressure. The resulting white solid was partitioned between chloroform (400 mL) and saturated aqueous sodium bicarbonate (50 mL). The phases were separated and the aqueous phase was extracted with chloroform (2×20 mL). The combined organics were washed with saturated aqueous sodium bicarbonate (3×25 mL), dried over magnesium sulfate, filtered, concentrated under reduced pressure, and then dried under high vacuum to provide 11.75 g of 7-(4-chlorobutyl)-5,6-dimethyl-8-propyl-7H-imidazo[4,5-c]tetraazolo[1,5-a]pyridine an off white solid.

Part F

A mixture of the material from Part E (1.0 eq), potassium thioacetate (4.6 g, 1.1 eq), and DMF (250 mL) was stirred under a nitrogen atmosphere overnight. The reaction mixture was concentrated under reduced pressure and the residue was partitioned between chloroform (300 mL) and water/brine (1:1 100 mL). The phases were separated and the aqueous phase was extracted with chloroform (2×75 mL). The combined organics were washed with water/brine (1:1, 3×50 mL), dried over magnesium sulfate, filtered, concentrated under reduced pressure, and then dried under high vacuum with gentle heating to provide 13.0 g of S-[4-(5,6-dimethyl-8-propyl-7H-imidazo[4,5-c]tetraazolo[1,5-a]pyridin-7-yl)butyl]thioacetate as a brown solid.

Part G

A solution of S-[4-(5,6-dimethyl-8-propyl-7H-imidazo[4,5-c]tetraazolo[1,5-a]pyridin-7-yl)butyl]thioacetate (6.5 g, 18.0 mmol, 1.0 eq) in methanol (150 mL) was degassed with nitrogen for about 10 minutes. Sodium methoxide (10.3 mL of 25 wt % in methanol, 2.5 eq) was added dropwise over a period of 5 minutes. The solution was stirred at ambient temperature for 2 hrs and then concentrated under reduced pressure. The residue was partitioned between dichloromethane (300 mL) and water (50 mL). The pH was adjusted to 7 by the addition of 1N hydrochloric acid. The phases were separated and the aqueous phase was extracted with dichloromethane (2×75 mL). The combined organics were washed with brine (50 mL), dried over magnesium sulfate, filtered, and then concentrated under reduced pressure to provide 4-(5,6-dimethyl-8-propyl-7H-imidazo[4,5-c]tetraazolo[1,5-a]pyridin-7-yl)butane-1-thiol as a yellow solid.

Part H

Under a nitrogen atmosphere, the material from Part G (1.0 eq) was combined with concentrated hydrochloric acid (30 mL) and water (20 mL) and then cooled to 0° C. A solution of sodium chlorate (2.50 g, 1.3 eq) in water (10 mL) was added over a period of 10 minutes with vigorous stirring. The reaction mixture was stirred for 2 hrs at 0° C. and then diluted with dichloromethane (100 mL). The pH was adjusted to 7 by slowly adding 6M potassium carbonate (~30 mL). A white precipitate formed during the addition. The reaction mixture was diluted with dichloromethane (100 mL) and water (100 mL) and then allowed to warm to ambient temperature. The aqueous layer was separated and then extracted with dichloromethane (2×50 mL). The combined organics were dried over magnesium sulfate, filtered and then concentrated under reduced pressure to provide 2.6 g of 4-(5,6-dimethyl-8-propyl-7H-imidazo[4,5-c]tetraazolo[1,5-a]pyridin-7-yl)butane-1-sulfonyl chloride as a yellow solid.

Part I

Under a nitrogen atmosphere, dimethylamine hydrochloride (1.16 g, 2.1 eq) was added to a suspension of the material from Part H (1.0 eq) in dichloromethane (65 mL). 6M potassium carbonate (2.81 mL, 2.5 eq) was added dropwise and the reaction mixture was stirred at ambient temperature for 2 hours. More dimethylamine hydrochloride (0.21 eq) and 6M potassium carbonate (0.25 eq) were added and the reaction mixture was stirred for 1 hr. The reaction mixture was diluted with dichloromethane (150 mL) and saturated aqueous sodium bicarbonate (75 mL) and the phases were separated. The aqueous phase was extracted with dichloromethane (3×50 mL). The combined organics were washed with aqueous sodium bicarbonate (2×50 mL), dried over magnesium sulfate, filtered, and then concentrated under reduced pressure to provide crude product as a yellow foam. The crude product was purified by HPFC (silica gel eluting with 2-30% CMA in chloroform) to provide 0.8 g of N,N dimethyl 4-(5,6-dimethyl-8-propyl-7H-imidazo[4,5-c]tetraazolo[1,5-a]pyridin-7-yl)butane-1-sulfonamide as a white solid.

Part J

The material from Part I, platinum (IV) oxide (160 mg), and trifluoroacetic acid (20 mL) were combined in a pressure vessel and placed under hydrogen pressure (50 psi, 3.4×10⁵ Pa) over the weekend. The reaction mixture was concentrated under reduced pressure. The residue was diluted with 1N hydrochloric acid (~10 mL) and then stirred at ambient temperature for 1 hr. The solution was cooled to 0° C., the pH was adjusted to 7-8 by adding saturated aqueous sodium bicarbonate, and then it was extracted with chloroform (3×75 mL). The combined organics were washed with aqueous sodium bicarbonate (3×40 mL), dried over sodium sulfate, filtered, concentrated under reduced pressure, and then dried under high vacuum to provide crude product. The crude product was recrystallized from ethyl acetate/hexanes, isolated by filtration, washed with ethyl acetate, and then dried under high vacuum overnight to provide 448 mg of N,N-dimethyl 4-(4-amino-6,7-dimethyl-2-propyl-1H-imidazo[4,5-c]pyridin-1-yl)butane-1-sulfonamide as a white powder, mp 127.0-128.0° C. $^1$H NMR (300 MHz, DMSO-$d_6$) δ 5.59 (s, 2H), 4.24 (dd, J=7.2, 6.4 Hz, 2H), 3.09 (dd, J=7.2, 6.8 Hz, 2H), 2.81-2.68 (m, 8H), 2.37 (s, 3H), 2.30 (s, 3H), 1.86-1.67 (m, 6H), 1.00 (t, J=7.4 Hz, 3H); MS (APCI) m/z 368 (M)⁺; Anal. calcd for $C_{17}H_{29}N_5O_2S$: C, 55.56; H, 7.95; N, 19.06; Found: C, 55.35; H, 8.08; N, 19.02.

Example 27

N-Methyl 4-(4-Amino-6,7-dimethyl-2-propyl-1H-imidazo[4,5-c]pyridin-1-yl)butane-1-sulfonamide

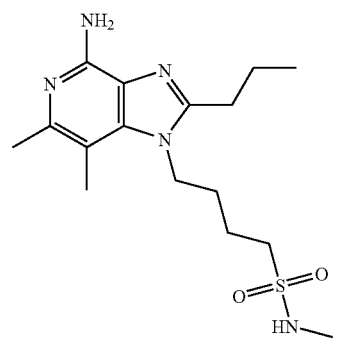

Part A

Using the general method of Example 26 Part I, 4-(5,6-dimethyl-8-propyl-7H-imidazo[4,5-c]tetraazolo[1,5-a]pyridin-7-yl)butane-1-sulfonyl chloride (2.0 g, 5.2 mmol, 1.0 eq) was reacted with methylamine hydrochloride (740 mg, 2.1 eq) to provide 1.86 g of N-methyl 4-(5,6-dimethyl-8-propyl-7H-imidazo[4,5-c]tetraazolo[1,5-a]pyridin-7-yl)butane-1-sulfonamide.

Part B

The material from Part A, platinum IV oxide (~500 mg), and trifluoroacetic acid (50 mL) were combined in a pressure vessel and placed under hydrogen pressure (50 psi, 3.4×10⁵ Pa) until analysis by HPLC indicated that the reaction was complete. The reaction mixture was filtered and the filter cake was washed with methanol. The filtrate was concentrated under reduced pressure. The residue was diluted with 1N hydrochloric acid (~10 mL) and then stirred at ambient temperature for 1 hr. The solution was cooled to 0° C. and the pH was adjusted to 7-8 by adding saturated aqueous sodium bicarbonate. A white precipitate formed. The precipitate was isolated by filtration, rinsed with water, and then dissolved in methanol. The methanol solution was filtered, diluted with toluene, concentrated under reduced pressure, and then dried under high vacuum to provide a white solid. The solid was triturated with ethyl acetate and methanol, isolated by filtration, washed sequentially with ethyl acetate, acetonitrile, chloroform, and ethyl acetate, and then dried under high vacuum. The material was then combined with 1N sodium hydroxide (5 mL), sonicated for 1 minute, and diluted with water (20 mL) and chloroform (100 mL). The phases were separated and the aqueous phase was extracted with chloroform (3×20 mL). The combined organics were washed with 1N sodium hydroxide. The combined aqueous were neutralized to pH 7 by the addition of 1N hydrochloric acid and then back extracted, with chloroform (3×30 mL). The combined organics were dried over sodium sulfate, filtered, concentrated under reduced pressure, dried under high vacuum at 100° C. for 3 hrs, triturated sequentially with ethyl acetate and methanol, and then dried under high vacuum to provide 100 mg of N-methyl 4-(4-amino-6,7-dimethyl-2-propyl-1H-imidazo[4,5-c]pyridin-1-yl)butane-1-sulfonamide as a white powder, mp 164.0-166.0° C. $^1$H NMR (300 MHz, DMSO-$d_6$)

δ 6.88 (q, J=4.9 Hz, 1H), 5.72 (s, 2H), 4.23 (dd, J=7.8, 6.3 Hz, 2H), 3.06 (dd, J=7.6, 6.6 Hz, 2H), 2.77 (t, J=7.4 Hz, 2H), 2.56 (d, J=4.9 Hz, 3H), 2.37 (s, 3H), 2.31 (s, 3H), 1.86-1.65 (m, 6H), 1.00 (t, J=7.4 Hz, 3H); MS (APCI) m/z 354 (M)$^+$; Anal. Calcd for $C_{16}H_{27}N_5O_2S$: C, 54.37; H, 7.699; N, 19.81; Found: C, 54.14; H, 7.76; N, 19.62.

Example 28

N,N-Dimethyl 4-(4-Amino-6,7-dimethyl-2-ethoxymethyl-1H-imidazo[4,5-c]pyridin-1-yl)butane-1-sulfonamide

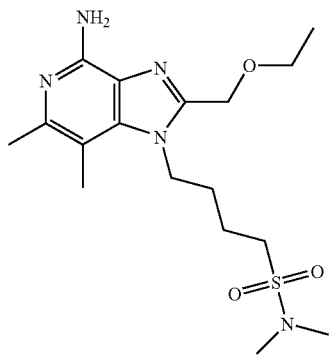

Part A

Ethoxyacetyl chloride (3.93 g, 1.0 eq) was slowly added to a chilled (0° C.) suspension of $N^7$-(4-chlorobutyl)-5,6-dimethyltetraazolo[1,5-a]pyridine-7,8-diamine (7.93 g, 29.5 mmol, 1.0 eq) in dichloromethane (200 mL). The reaction mixture was allowed to warm to ambient temperature overnight. Analysis by HPLC indicated that the reaction was not complete. The reaction mixture was cooled to 0° C., more ethoxyacetyl chloride (0.4 g) was added, and then the reaction mixture was allowed to warm to ambient temperature and stirred overnight; this procedure was repeated. The reaction mixture was diluted with saturated aqueous sodium bicarbonate (~100 mL) and dichloromethane (100 mL). The phases were separated and the aqueous phase was extracted with dichloromethane (3×50 mL). The combined organics were washed with aqueous sodium bicarbonate (2×50 mL), dried over magnesium sulfate, filtered, and then concentrated under reduced pressure to provide 10.5 g of crude product as a brown solid. This material was triturated with ethyl acetate/hexanes then dried under high vacuum to provide 6.4 g of 7-(4-chlorobutyl)-8-ethoxymethyl-5,6-dimethyl-7H-imidazo[4,5-c]tetraazolo[1,5-a]pyridine as a white solid.

Part B

Using the general method of Example 26 Part F, 7-(4-chlorobutyl)-8-ethoxymethyl-5,6-dimethyl-7H-imidazo[4,5-c]tetraazolo[1,5-a]pyridine (7.1 g, 21.1 mmol, 1.0 eq) was reacted with potassium thioacetate (3.61 g, 1.5 eq) to provide 6.5 g of S-[4-(8-ethoxymethyl-5,6-dimethyl-7H-imidazo[4,5-c]tetraazolo[1,5-a]pyridin-7-yl)butyl]thioacetate as a tan solid.

Part C

Using the general method of Example 26 Part G, S-[4-(8-ethoxymethyl-5,6-dimethyl-7H-imidazo[4,5-c]tetraazolo[1,5-a]pyridin-7-yl)butyl]thioacetate (2.00 g, 5.31 mmol, 1.0 eq) was hydrolyzed to provide 4-(8-ethoxymethyl-5,6-dimethyl-7H-imidazo[4,5-c]tetraazolo[1,5-a]pyridin-7-yl)butane-1-thiol as a yellow solid.

Part D

Using the general method of Example 26 Part H, the material from Part C was oxidized to provide 4-(8-ethoxymethyl-5,6-dimethyl-7H-imidazo[4,5-c]tetraazolo[1,5-a]pyridin-7-yl)butane-1-sulfonyl chloride.

Part E

Using the general method of Example 26 Part I, the material from Part D was reacted with dimethylamine hydrochloride. The crude product was purified by HPFC (silica gel eluting with 2-30% CMA in chloroform) to provide 1.1 g of N,N dimethyl 4-(8-ethoxymethyl-5,6-dimethyl-7H-imidazo[4,5-c]tetraazolo[1,5-a]pyridin-7-yl)butane-1-sulfonamide.

Part F

Using the general method of Example 26 Part J, N,N dimethyl 4-(8-ethoxymethyl-5,6-dimethyl-7H-imidazo[4,5-c]tetraazolo[1,5-a]pyridin-7-yl)butane-1-sulfonamide (0.21 g, 0.51 mmol, 1.0 eq) was reduced. The crude product was triturated with ethyl acetate and dried under high vacuum at 100° C. for 3 hrs to provide 0.11 g of N,N-dimethyl 4-(4-amino-6,7-dimethyl-2-ethoxymethyl-1H-imidazo[4,5-c]pyridin-1-yl)butane-1-sulfonamide as a white powder, mp 158.0-160.0° C. $^1$H NMR (300 MHz, DMSO-$d_6$) δ 5.77 (s, 2H), 4.65 (s, 2H), 4.31 (dd, J=8.1, 7.1 Hz, 2H), 3.52 (q, J=7.0 Hz, 2H), 3.08 (dd, J=7.6, 7.3 Hz, 2H), 2.75 (s, 6H), 2.38 (s, 3H), 2.31 (s, 3H), 1.92-1.68 (m, 4H), 1.15 (t, J=7.0 Hz, 3H); MS (APCI) m/z 384 (M)$^+$; Anal. Calcd for $C_{17}H_{29}N_5O_3S \cdot 0.33H_2O$: C, 52.43; H, 7.68; N, 17.98; Found: C, 52.34; H, 7.81; N, 18.11.

Example 29

N,N-Dimethyl 4-(4-Amino-2-ethoxymethyl-1H-imidazo[4,5-c][1,5]naphthyridin-1-yl)butane-1-sulfonamide

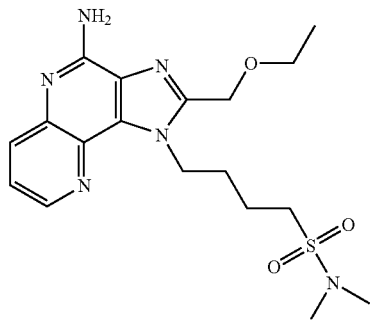 [SMILES: CCOCc1nc2c(N)nc3cccnc3c2n1CCCCS(=O)(=O)N(C)C]

Part A

Phosphorous oxychloride (38 mL, 1.3 eq) was added dropwise over a period of 70 minutes to a suspension of 4-hydroxy-3-nitro[1,5]naphthyridine (60 g, 314 mmol, 1.0 eq). The orange suspension was stirred at ambient temperature for 5 hrs and then poured into ice water (1.9 L) and stirred for 30 minutes. The solid was isolated by filtration, washed with water (3×200 mL), and then dissolved in dichloromethane (1.2 L). The solution was dried over magnesium sulfate, filtered, and concentrated under reduced pressure to provide 61.1 g of 4-chloro-3-nitro[1,5]naphthyridine as an orange solid.

Part B

Triethylamine (6.4 mL, 1.2 eq) was added to a suspension of 4-chloro-3-nitro[1,5]naphthyridine (8.0 g, 38.2 mmol, 1.0 eq) in dichloromethane. The resulting solution was cooled to 5° C. and 4-amino-1-butanol (3.8 mL, 1.1 eq) was added dropwise over a period of 5 minutes. The reaction mixture was allowed to stir at ambient temperature for 3 hrs then it was diluted with saturated aqueous sodium bicarbonate (100 mL). The phases were separated and the aqueous phase was extracted with dichloromethane (2×50 mL). The combined organics were dried over magnesium sulfate, filtered, and then concentrated under reduced pressure to provide 9.94 g of 4-[(3-nitro[1,5]naphthyridin-4-yl)amino]butan-1-ol as a yellow solid.

Part C

Thionyl chloride (3.0 mL, 1.1 eq) was added dropwise to a chilled (0° C.) solution of the material from Part B (1.0 eq) in dichloromethane (190 mL). A white precipitate formed during the addition and additional dichloromethane (170 mL) was added to facilitate stirring. The reaction mixture was allowed to stir at ambient temperature overnight and then it was quenched with 50% saturated sodium bicarbonate (200 mL). The phases were separated and the aqueous phase was extracted with dichloromethane (2×75 mL). The combined organics were dried over magnesium sulfate, filtered, and then concentrated under reduced pressure to provide 10.6 g of N-(4-chlorobutyl)-3-nitro[1,5]naphthyridin-4-amine as yellow solid.

Part D

Catalyst (1.1 g of 5% platinum on carbon) was added to a suspension of the material from Part C in ethyl acetate (190 mL). The mixture was placed under hydrogen pressure ((30 psi ($2.1 \times 10^5$ Pa)) for 2 hours. The reaction mixture was filtered through a layer of CELITE filter aid. The filter cake was rinsed with ethyl acetate (50 mL). The filtrate was concentrated under reduced pressure to provide $N^4$-(4-chlorobutyl)[1,5]naphthyridine-3,4-diamine as a thick yellow oil.

Part E

Ethoxyacetyl chloride (4.5 mL, 1.1 eq) was added dropwise over a period of 10 minutes to a solution of the material from Part D (1.0 eq) in dichloromethane (180 mL). The reaction mixture was allowed to stir at ambient temperature for 1 hr and then it was concentrated under reduced pressure to provide N-[4-(4-chlorobutyl)amino[1,5]naphthyridin-3-yl]-2-ethoxyacetamide hydrochloride.

Part F

The material from Part E was suspended in 3:1 ethanol: water (200 mL). 6M potassium carbonate (9.5 mL, 1.5 eq) was added and the reaction mixture was allowed to stir at ambient temperature for 2 weeks with additional potassium carbonate being added after 1 week. The reaction mixture was concentrated under reduced pressure and the residue was partitioned between dichloromethane (100 mL) and brine (100 mL). The phases were separated and the aqueous phase was extracted with dichloromethane (50 mL). The combined organics were dried over magnesium sulfate, filtered, and then concentrated under reduced pressure to provide 12.2 g of 1-(4-chlorobutyl)-2-ethoxymethyl-1H-imidazo[4,5-c][1,5]naphthyridine as a brown oil.

Part G

Potassium thioacetate (4.75 g, 1.1 eq) was added in a single portion to a solution of the material from Part F (1.0 eq) in DMF (150 mL). The reaction mixture was stirred overnight and then concentrated under reduced pressure. The residue was dissolved in dichloromethane (200 mL), washed sequentially with water (100 mL) and brine (100 mL), dried over magnesium sulfate, filtered, and then concentrated under reduced pressure to provide 14.8 g of crude S-[4-(2-ethoxymethyl-1H-imidazo[4,5-c][1,5]naphthyridin-1-yl)butyl]thioacetate as a brown oil.

Part H

A portion (1.5 g, 1.0 eq) of the material from Part G was dissolved in methanol (20 mL). The solution was degassed with a nitrogen stream and then sodium methoxide (2.4 mL of 25 wt % in methanol, 2.5 eq) was added dropwise over a period of 3 minutes. The reaction mixture was stirred at ambient temperature for 1 hr and then concentrated under reduced pressure. The residue was partitioned between dichloromethane (70 mL) and water (40 mL). The pH was adjusted to 7 by the addition of 2M hydrochloric acid. The phases were separated and the aqueous phase was extracted with dichloromethane (30 mL). The combined organics were washed with brine (40 mL), dried over magnesium sulfate, filtered, and then concentrated under reduced pressure to provide 1.36 g of 4-(2-ethoxymethyl-1H-imidazo[4,5-c][1,5]naphthyridin-1-yl)butane-1-thiol as a tan solid.

Part I

A solution of sodium chlorate (0.58 g, 1.3 eq) in water (2 mL) was added dropwise over a period of 2 minutes to a chilled (0° C.) solution of the material from Part H (1.0 eq) in a mixture of concentrated hydrochloric acid (7 mL) and water (5 mL). The reaction mixture was stirred at 0° C. for 1 hr and then diluted with dichloromethane (50 mL). The pH was adjusted to 5 by the addition of 6M potassium carbonate (8 mL) over a period of 20 minutes. The mixture was warmed to ambient temperature and then further diluted with dichloromethane (50 mL) and water (50 mL). The phases were separated and the aqueous phase was extracted with dichloromethane (2×20 mL). The combined organics were dried over magnesium sulfate, filtered, and then concentrated under reduced pressure to provide 1.43 g of 4-(2-ethoxymethyl-1H-imidazo[4,5-c][1,5]naphthyridin-1-yl)butane-1-sulfonyl chloride as a pale yellow solid.

Part J

Dimethylamine hydrochloride (0.64 g, 2.1 eq) and 6M potassium carbonate (1.6 mL, 2.5 eq) were added sequentially to a solution of the material from Part I (1.0 eq) in dichloromethane (18 mL). The reaction mixture was stirred at ambient temperature for 1 hr and then diluted with dichloromethane (40 mL) and saturated aqueous sodium bicarbonate (40 mL). The phases were separated and the aqueous phase was extracted with dichloromethane (2×20 mL). The combined organics were dried over magnesium sulfate, filtered, and then concentrated under reduced pressure to provide 1.06 g of an orange solid. This material was purified by HPFC (silica gel eluting with 0-30% CMA in chloroform over 1.2 L) to provide 0.48 g of pure N,N-dimethyl 4-(2-ethoxymethyl-1H-imidazo[4,5-c][1,5]naphthyridin-1-yl)butane-1-sulfonamide and 0.40 g of a mixture. The mixture was recrystallized from dichloromethane and hexanes to provide an additional 0.27 g of N,N-dimethyl 4-(2-ethoxymethyl-1H-imidazo[4,5-c][1,5]naphthyridin-1-yl)butane-1-sulfonamide.

Part K

3-Chloroperoxybenzoic acid (0.66 g of 70%, 1.4 eq) was added to a solution of N,N-dimethyl 4-(2-ethoxymethyl-1H-imidazo[4,5-c][1,5]naphthyridin-1-yl)butane-1-sulfonamide (0.75 g, 1.92 mmol, 1.0 eq) in chloroform (10 mL). The reaction was stirred at ambient temperature for 3 hrs. Analysis by LCMS indicated that the reaction was not complete so additional 3-chloroperoxybenzoic acid (1.4 eq) was added. After an additional 2 hrs of stirring more 3-chloroperoxybenzoic acid (0.42 g) was added and stirring was continued for another hour. The reaction mixture was diluted with saturated aqueous sodium bicarbonate (75 mL) and chloroform (75 mL). The phases were separated and the organic phase was washed with saturated aqueous sodium bicarbonate (75 mL).

The combined aqueous was extracted with dichloromethane (2×30 mL). The combined organics were dried over magnesium sulfate, filtered, and then concentrated under reduced pressure to provide 1.27 g of N,N-dimethyl 4-(2-ethoxymethyl-5-oxy-1H-imidazo[4,5-c][1,5]naphthyridin-1-yl)butane-1-sulfonamide as an orange solid.

Part L

Ammonium hydroxide (0.64 mL of 15M, 5.0 eq) was added to a chilled (0° C.) solution of the material from Part K (1.0 eq) in methanol (10 mL). Benzenesulfonyl chloride (0.51 mL, 2.1 eq) was added dropwise. The reaction mixture was stirred at 0° C. for 1 hr and then concentrated under reduced pressure. The residue was partitioned between dichloromethane (70 mL) and saturated aqueous sodium bicarbonate (50 mL). The phases were separated and the aqueous phase was extracted with dichloromethane (2×20 mL). The combined organics were dried over magnesium sulfate, filtered, and then concentrated under reduced pressure to provide 1.22 g of crude product as an orange solid. This material was purified twice by HPFC (silica gel eluting with 0-25% CMA in chloroform over 1.3 L, 25-30% CMA in chloroform over 600 mL; silica gel eluting with 0-30% CMA in chloroform over 960 mL) to provide 0.180 g of a tan solid. This material was recrystallized from chloroform/hexanes and then dried under high vacuum to provide 100 mg of N,N-dimethyl 4-(4-amino-2-ethoxymethyl-1H-imidazo[4,5-c][1,5]naphthyridn-1-yl)butane-1-sulfonamide as a white powder, mp 148-150° C. $^1$H NMR (300 MHz, DMSO-d6) δ 8.53 (dd, J=4.4, 1.6 Hz, 1H), 7.92 (dd, J=8.4, 1.6 Hz, 1H), 7.46 (dd, J=8.4, 4.4 Hz, 1H), 6.88 (br s, 2H), 4.87 (t, J=7.4 Hz, 2H), 4.79 (s, 2H), 3.58 (q, J=7.0 Hz, 2H), 3.09 (t, J=7.7 Hz, 2H), 2.71 (s, 6H), 2.04 (m, 2H), 1.77 (m, 2H), 1.18 (t, J=7.0 Hz, 3H); MS (APCI) m/z 407 (M+1)$^+$; Anal. calcd for $C_{18}H_{26}N_6O_3S$: C, 53.18; H, 6.45; N, 20.67. Found: C, 52.83; H, 6.40; N, 20.99.

Example 30

N,N-Dimethyl 4-(4-Amino-2-propyl-1H-imidazo[4,5-c][1,5]naphthyridin-1-yl)butane-1-sulfonamide

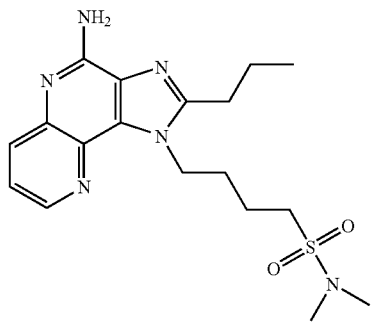 [SMILES: CCCc1nc2c(N)nc3cccnc3c2n1CCCCS(=O)(=O)N(C)C]

Part A

Trimethyl orthobutyrate (7.4 mL, 1.3 eq) and pyridine hydrochloride (0.20 g, 0.05 eq) were added to a solution of N-(4-chlorobutyl)[1,5]naphthyridine-3,4-diamine (1.0 eq) in toluene (120 mL). The reaction mixture was heated at reflux for 2 hrs, allowed to cool to ambient temperature, and then concentrated under reduced pressure. The residue was dissolved in dichloromethane (120 mL) and washed with saturated aqueous sodium bicarbonate (100 mL). The aqueous wash was extracted with dichloromethane (2×25 mL). The combined organics were dried over magnesium sulfate, filtered, and then concentrated under reduced pressure to provide 10.8 g of 1-(4-chlorobutyl)-2-propyl-1H-imidazo[4,5-c][1,5]naphthyridine as a yellow solid.

Part B

Using the general method of Example 29 Part G, 1-(4-chlorobutyl)-2-propyl-1H-imidazo[4,5-c][1,5]naphthyridine (11.3 g, 37.3 mmol, 1.0 eq) was reacted with potassium thioacetate (4.69 g, 1.1 eq) to provide 15.43 g of crude S-[4-(2-propyl-1H-imidazo[4,5-c][1,5]naphthyridin-1-yl)butyl] thioacetate as a brown oil.

Part C

Using the general method of Example 29 Part H, S-[4-(2-propyl-1H-imidazo[4,5-c][1,5]naphthyridin-1-yl)butyl]thioacetate (3.0 g, 8.76 mmol) was hydrolyzed to provide 2.71 g of 4-(2-propyl-1H-imidazo[4,5-c][1,5]naphthyridin-1-yl)butane-1-thiol as a brown oil.

Part D

Using the general method of Example 29 Part I, the material from Part C was oxidized to provide 2.15 g of 4-(2-propyl-1H-imidazo[4,5-c][1,5]naphthyridin-1-yl)butane-1-sulfonyl chloride as a pale yellow solid.

Part E

Using the general method of Example 29 Part J, the material from Part D (1.0 eq) was reacted with dimethylamine hydrochloride (1.00 g, 2.1 eq) to provide 2.26 g of N,N-dimethyl 4-(2-propyl-1H-imidazo[4,5-c][1,5]naphthyridin-1-yl)butane-1-sulfonamide as a yellow solid.

Part F

3-Chloroperoxybenzoic acid (1.98 g of 70%, 1.5 eq) was added to a solution of the material from Part E (1.0 eq) in chloroform (25 mL). The reaction was stirred at ambient temperature for 1 hr. Analysis by LCMS indicated that the reaction was not complete. More 3-chloroperoxybenzoic acid (0.36 g) was added and the reaction mixture was stirred for another hour. Ammonium hydroxide (5 mL) was added followed by the portionwise addition of tosyl chloride (1.12 g, 1.1 eq). The reaction mixture was stirred at ambient temperature for 1 hr and then filtered to remove a white solid. The filtrate was diluted with dichloromethane (50 mL) and saturated aqueous sodium bicarbonate (50 mL). The phases were separated and the aqueous phase was extracted with dichloromethane (2×20 mL). The combined organics were dried over magnesium sulfate, filtered, and then concentrated under reduced pressure to provide 3.03 g of crude product as an orange solid. This material was purified by HPFC (silica gel eluting with 0-30% CMA in chloroform over 1.2 L and 30% CMA in chloroform over 450 mL) to provide 1.36 g of a yellow solid. This material was recrystallized from chloroform/hexanes and then dried under high vacuum at 80° C. for 18 hrs to provide 0.747 g of N,N-dimethyl 4-(4-amino-2-propyl-1H-imidazo[4,5-c][1,5]naphthyridin-1-yl)butane-1-sulfonamide as an off-white powder, mp 162-163° C. $^1$H NMR (300 MHz, DMSO-d6) δ 8.51 (dd, J=4.3, 1.6 Hz, 1H), 7.91 (dd, J=8.4, 1.6 Hz, 1H), 7.43 (dd, J=8.4, 4.3 Hz, 1H), 6.74 (br s, 2H), 4.85 (t, J=7.2 Hz, 2H), 3.10 (t, J=7.7 Hz, 2H), 2.92 (t, J=7.5 Hz, 2H), 2.70 (s, 6H), 1.95 (m, 2H), 1.87 (sextet, J=7.5 Hz, 2H), 1.74 (m, 2H), 1.04 (t, J=7.4 Hz, 3H); MS (APCI) m/z 391 (M+1)+; Anal. calcd for $C_{18}H_{26}N_6O_2S$: C, 55.36; H, 6.71; N, 21.52. Found: C, 55.18; H, 6.98; N, 21.28.

Example 31

4-(4-Amino-6,7-dimethyl-2-propyl-1H-imidazo[4,5-c]pyridin-1-yl)butane-1-sulfonamide

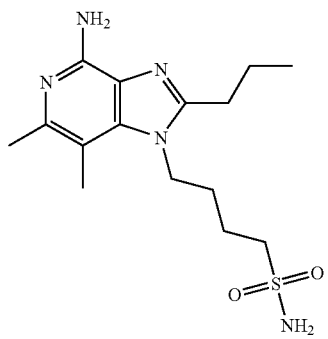 [SMILES: CCCc1nc2c(N)nc(C)c(C)c2n1CCCCS(N)(=O)=O]

Part A

The preparation of 4-(5,6-dimethyl-8-propyl-7H-imidazo[4,5-c]tetraazolo[1,5-a]pyridin-7-yl)butane-1-sulfonyl chloride is described in Parts A-H of Example 26. p-Methoxybenzylamine (2.37 mL, 18.17 mmol, 2.2 eq) was added dropwise over 3 minutes to a solution of 4-(5,6-dimethyl-8-propyl-7H-imidazo[4,5-c]tetraazolo[1,5-a]pyridin-7-yl)butane-1-sulfonyl chloride (3.18 g, 8.26 mmol, 1 eq) in dichloromethane (80 mL) at ambient temperature and stirred overnight. The reaction mixture was diluted with dichloromethane (150 mL) and water (50 mL) and the phases were separated. The aqueous was extracted with dichloromethane (2×30 mL). The combined organics were washed sequentially with water (3 mL) and brine (20 mL), dried over magnesium sulfate, filtered and concentrated under reduced pressure. The crude reaction was purified by HPFC (silica gel eluting with 2-30% CMA in chloroform) to provide 2.01 g of N-(4-methoxybenzyl) 4-(5,6-dimethyl-8-propyl-7H-imidazo[4,5-c]tetraazolo[1,5-a]pyridin-7-yl)butane-1-sulfonamide as a white foam.

Part B

Platinum IV oxide (340 mg), trifluoroacetic acid (35 mL), and N-(4-methoxybenzyl) 4-(5,6-dimethyl-8-propyl-7H-imidazo[4,5-c]tetraazolo[1,5-a]pyridin-7-yl)butane-1-sulfonamide (1.7 g, 3.5 mmol) were combined in a pressure vessel and placed under hydrogen pressure (50 psi, $3.4×10^5$ Pa) until analysis by HPFC indicated the reaction was complete. The reaction mixture was filtered and the filter cake was washed with methanol. The filtrate was concentrated under reduced pressure. The residue was diluted with 1N hydrochloric acid (~10 mL) and then stirred at ambient temperature for 1 hr. The mixture was diluted with chloroform (50 mL) and the pH adjusted to 14 with 6N sodium hydroxide. The phases were separated and the aqueous layer was extracted with chloroform (2×30 mL), adjusted to pH of 10 with 1 N hydrochloric acid, and then back extracted with chloroform (4×70 mL). The combined organics were dried over sodium sulfate, filtered, concentrated under reduced pressure, triturated with acetonitrile, filtered and dried under high vacuum at 100° C. for 3 hours and 80° C. over night to afford 0.352 g of 4-(4-amino-6,7-dimethyl-2-propyl-1H-imidazo[4,5-c]pyridin-1-yl)butane-1-sulfonamide as a white powder, mp 167.0-169.0° C. $^1$H NMR (300 MHz, DMSO-$d_6$) δ 6.78 (s, 2H), 5.57 (s, 2H), 4.26-4.18 (m, 2H), 3.08-2.99 (m, 2H), 2.77 (dd, J=7.7, 7.3 Hz, 2H), 2.37 (s, 3H), 2.30 (s, 3H), 1.86-1.72 (m, 6H), 1.00 (t, J=7.4 Hz, 3H); MS (APCI) m/z 340 (M)+; Anal. Calcd for $C_{15}H_{25}N_5O_2S.0.2H_2OC$, 52.52; H, 7.46; N, 20.41; Found: C, 52.59; H, 7.68; N, 20.75.

Example 32

N-Methyl 4-(4-Amino-2-ethoxymethyl-1H-imidazo[4,5-c][1,5]naphthyridin-1-yl)butane-1-sulfonamide

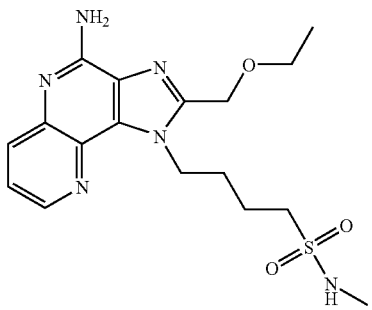 [SMILES: CCOCc1nc2c(N)nc3cccnc3c2n1CCCCS(=O)(=O)NC]

Part A

The preparation of 4-(2-ethoxymethyl-1H-imidazo[4,5-c][1,5]naphthyridin-1-yl)butane-1-sulfonyl chloride is described in Parts A-I of Example 29. The general method of Part J of Example 29 was repeated using methylamine hydrochloride (0.726 g, 2.1 eq) in lieu of dimethylamine hydrochloride. Recrystallization was unnecessary to provide 1.16 g of N-methyl 4-(2-ethoxymethyl-1H-imidazo[4,5-c][1,5]naphthyridin-1-yl)butane-1-sulfonamide.

Part B

3-Chloroperoxybenzoic acid (0.96 g of 70%, 2 eq) was added to a solution of N-methyl 4-(2-ethoxymethyl-1H-imidazo[4,5-c][1,5]naphthyridin-1-yl)butane-1-sulfonamide. (1.05 g, 2.78 mmol, 1 eq) in chloroform (14 mL). The reaction was stirred at ambient temperature for 3 hours followed by sequential addition of ammonium hydroxide (4 mL) and tosyl chloride (0.58 g, 3.06 mmol). The reaction was stirred for 1 hour and additional tosyl chloride (0.20 g) was added. The reaction mixture was diluted with dichloromethane (40 mL) and saturated aqueous sodium bicarbonate. The phases were separated and the aqueous layer was back extracted with dichloromethane (2×20 mL). The combined organics were dried over magnesium sulfate, filtered and concentrated under reduced pressure to provide an orange solid. The material was further purified by HPFC (silica gel eluting with 0-30% CMA in chloroform), trituration with acetonitrile, and drying in a vacuum oven at 75° C. to afford 0.503 g of N-Methyl 4-(4-amino-2-ethoxymethyl-1H-imidazo[4,5-c][1,5]naphthyridin-1-yl)butane-1-sulfonamide as a white powder, mp 148-150° C. Anal. calcd for $C_{17}H_{24}N_6O_3S$: C, 52.02; H, 6.16; N, 21.41. Found: C, 51.73; H, 6.41; N, 21.39.

Example 33

N-Methyl 4-(4-Amino-2-propyl-1H-imidazo[4,5-c][1,5]naphthyridin-1-yl)butane-1-sulfonamide

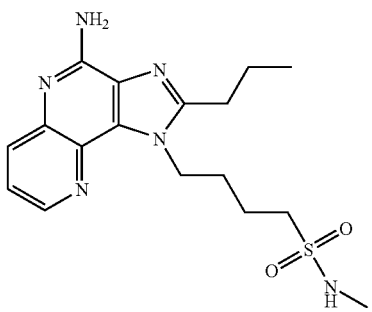 [SMILES: CCCc1nc2c(N)nc3cccnc3c2n1CCCCS(=O)(=O)NC]

Part A

The preparation of 4-(2-propyl-1H-imidazo[4,5-c][1,5]naphthyridin-1-yl)butane-1-sulfonyl chloride is described in Parts A-D of Example 30. The general method of Part J of Example 29 was repeated using methylamine hydrochloride (0.92 g, 2.1 eq) in lieu of dimethylamine hydrochloride to afford 1.64 g of N-methyl 4-(2-propyl-1H-imidazo[4,5-c][1,5]naphthyridin-1-yl)butane-1-sulfonamide. Purification by column chromatography or recrystallization was unnecessary for the next reaction.

Part B

3-Chloroperoxybenzoic acid (1.66 g of 70%, 2 eq) was added to a solution of N—-methyl 4-(2-propyl-1H-imidazo[4,5-c][1,5]naphthyridin-1-yl)butane-1-sulfonamide (1.74 g, 4.81 mmol, 1 eq) in chloroform (25 mL). The reaction was stirred at ambient temperature for 1.5 hours followed by sequential addition of ammonium hydroxide (5 mL) and p-toluenesulfonyl chloride (1.01 g, 5.29 mmol). The reaction was stirred for 1 hour and diluted with dichloromethane (40 mL) and saturated aqueous sodium bicarbonate. The phases were separated and the aqueous layer was back extracted with dichloromethane (2×20 mL). The combined organics were dried over magnesium sulfate, filtered and concentrated under reduced pressure to provide an orange solid. The material was further purified by HPFC (silica gel eluting with 0-30% CMA in chloroform), trituration with acetonitrile, and drying under high vacuum at 100° C. to afford 0.422 g of N-methyl 4-(4-amino-2-propyl-1H-imidazo[4,5-c][1,5]naphthyridin-1-yl)butane-1-sulfonamide as an off-white solid, mp 174-175° C. Anal. calcd for $C_{17}H_{24}N_6O_2S$: C, 54.24; H, 6.43; N, 22.32. Found: C, 54.02; H, 6.42; N, 22.22.

Example 34

N-Methyl 4-(4-Amino-6,7-dimethyl-2-ethoxymethyl-1H-imidazo[4,5-c]pyridin-1-yl) butane-1-sulfonamide

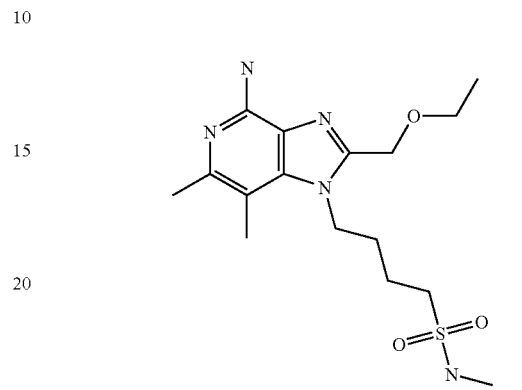

Part A

Methylamine hydrochloride (0.85 g, 12.5 mmol) was added to a suspension of 4-(8-ethoxymethyl-5,6-dimethyl-7H-imidazo[4,5-c]tetrazolo[1,5-a]pyridin-7-yl)butane-1-sulfonyl chloride (2.38 g, 5.94 mmol, synthesis described in Parts A-D of Example 28) in dichloromethane (60 mL) at ambient temperature. Dropwise addition of 6M potassium carbonate (2.5 mL) followed and the reaction was stirred overnight. The reaction mixture was diluted with dichloromethane (150 mL) and saturated aqueous sodium bicarbonate and separated. The aqueous layer was back-extracted with dichloromethane (3×50 mL) and the combined organics were washed with saturated aqueous sodium bicarbonate (2×50 mL), dried over magnesium sulfate, filtered, and concentrated under reduced pressure to afford 1.87 g of N-methyl 4-(8-ethoxymethyl-5,6-dimethyl-7H-imidazo[4,5-c]tetraazolo[1,5-a]pyridin-7-yl)butane-1-sulfonamide as a white foam.

Part B

Platinum IV oxide (400 mg), trifluoroacetic acid (50 mL), and N-methyl 4-(8-ethoxymethyl-5,6-dimethyl-7H-imidazo[4,5-c]tetraazolo[1,5-a]pyridin-7-yl)butane-1-sulfonamide (1.87 g, 4.73 mmol) were combined in a pressure vessel and placed under hydrogen pressure (50 psi, $3.4 \times 10^5$ Pa) and agitated over the weekend. Analysis by HPLC indicated the reaction was incomplete and additional platinum IV oxide (150 mg) was added. After 24 hours, the reaction mixture was filtered and the filter cake was washed with methanol. The filtrate was concentrated under reduced pressure. The residue was diluted with 1N hydrochloric acid (~5 mL) and then stirred at ambient temperature for 1 hr. The mixture was cooled to 0° C. and diluted with chloroform (100 mL) and the pH adjusted to 14 with 6N sodium hydroxide. The phases were separated and the aqueous layer was extracted with chloroform (3×100 mL). The combined organics were dried over sodium sulfate, filtered, and concentrated under reduced pressure, triturated with acetonitrile, filtered and concentrated to give a white solid. The material was further purified by HPFC (silica gel eluting with 15-40% CMA in chloroform) and recrystallized from acetonitrile to afford 0.592 g of N-methyl 4-(4-amino-6,7-dimethyl-2-ethoxymethyl-1H-imidazo[4,5-c]pyridin-1-yl)butane-1-sulfonamide as a white powder, mp 194.5-196.0° C. $^1$H NMR (300 MHz, DMSO-$d_6$)

δ 6.89 (q, J=5.0 Hz, 1H), 5.77 (s, 2H), 4.65 (s, 2H), 4.30 (dd, J=8.2, 7.3 Hz, 2H), 3.51 (q, J=7.0 Hz, 2H), 3.05 (dd, J=7.7, 7.3 Hz, 2H), 2.56 (d, J=5.0 Hz, 3H), 2.38 (s, 3H), 2.31 (s, 3H), 1.92-1.66 (m, 4H), 1.15 (t, J=7.0 Hz, 3H); MS (APCI) m/z 370 (M)$^+$; Anal. Calcd for $C_{16}H_{27}N_5O_3SC$, 52.01; H, 7.37; N, 18.95; Found: C, 51.92; H, 7.45; N, 19.04.

Example 35

4-(4-Amino-2-ethoxymethyl-6,7-dimethyl-1H-imidazo[4,5-c]pyridin-1-yl)butane-1-sulfonamide

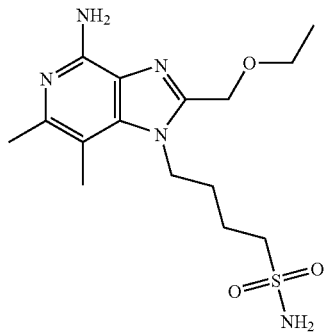 [SMILES: CCOCc1nc2c(N)nc(C)c(C)c2n1CCCCS(N)(=O)=O]

Part A

The general method of Example 31 was followed using 4-(8-ethoxymethyl-5,6-dimethyl-7H-imidazo[4,5-c]tetraazolo[1,5-a]pyridin-7-yl)butane-1-sulfonyl chloride (2.38 g, 5.94 mmol, synthesis described in Parts A-D of Example 28) in lieu of 4-(5,6-dimethyl-8-propyl-7H-imidazo[4,5-c]tetraazolo[1,5-a]pyridin-7-yl)butane-1-sulfonyl chloride. Purification was performed by successive triturations with ethyl acetate in lieu of column chromatography to afford 1.73 g of N-(4-methoxybenzyl) 4-(8-ethoxymethyl-5,6-dimethyl-7H-imidazo[4,5-c]tetraazolo[1,5-a]pyridin-7-yl)butane-1-sulfonamide.

Part B

Platinum IV oxide (350 mg), trifluoroacetic acid (35 mL), and N-(4-methoxybenzyl) 4-(8-ethoxymethyl-5,6-dimethyl-7H-imidazo[4,5-c]tetraazolo[1,5-a]pyridin-7-yl)butane-1-sulfonamide (1.73 g, 3.45 mmol) were combined in a pressure vessel and placed under hydrogen pressure (50 psi, 3.4×10$^5$ Pa) until analysis by HPLC indicated the reaction was complete. The reaction mixture was filtered and the filter cake was washed with methanol. The filtrate was concentrated under reduced pressure. The residue was diluted with 1N hydrochloric acid (~10 mL) and then stirred at ambient temperature for 1 hr. The mixture was cooled to 0° C. and diluted with chloroform (100 mL) and the pH adjusted to 14 with 6N sodium hydroxide. The phases were separated and the aqueous layer was adjusted to pH 7 with 1N hydrochloric acid and back-extracted with chloroform (2×30 mL). The combined organics were dried over sodium sulfate, filtered, and concentrated under reduced pressure. The solids were triturated sequentially with acetonitrile and ethyl acetate and dried under high vacuum at 80° C. Under sonication for 3 minutes, 6N sodium hydroxide (5 mL) and water (3 mL) were added to the solid, followed by adjustment of the pH of the mixture to 11 with 6N hydrochloric acid. The solution was cooled to 0° C., filtered, washed with water, triturated with acetonitrile to afford 237 mg of 4-(4-amino-2-ethoxymethyl-6,7-dimethyl-1H-imidazo[4,5-c]pyridin-1-yl)butane-1-sulfonamide as a white powder, mp 200.0-201.5° C. $^1$H NMR (300 MHz, DMSO-d$_6$) δ 6.79 (s, 2H), 5.77 (s, 2H), 4.66 (s, 2H), 4.30 (dd, J=8.0, 6.4 Hz, 2H), 3.51 (q, J=7.0 Hz, 2H), 3.03 (dd, J=7.7, 6.6 Hz, 2H), 2.38 (s, 3H), 2.31 (s, 3H), 1.91-1.71 (m, 4H), 1.15 (t, J=7.0 Hz, 3H); MS (APCI) m/z 356 (M)$^+$; Anal. Calcd for $C_{15}H_{25}N_5O_3S.0.4H_2OC$, 49.68; H, 7.17; N, 19.31; Found: C, 49.97; H, 7.38; N, 19.67.

Example 36

3-[4-Amino-2-(ethoxymethyl)-1H-imidazo[4,5-c]quinolin-1-yl]-N,2,2-trimethylpropane-1-sulfonamide

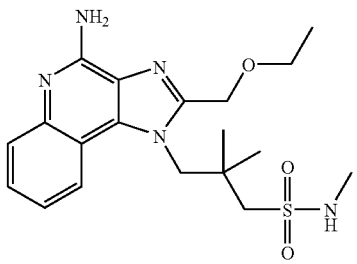 [SMILES: CCOCc1nc2c(N)nc3ccccc3c2n1CC(C)(C)CS(=O)(=O)NC]

Part A

Using the general method of Example 11 Part A, 3-[2-(ethoxymethyl)-1H-imidazo[4,5-c]quinolin-1-yl]-2,2-dimethylpropane-1-sulfonyl chloride (2.33 g, 5.88 mmol, 1.0 eq) was reacted with methylamine hydrochloride (834 mg, 2.1 eq) to provide 2.0 g of crude product. This material was purified by HPFC (silica gel eluting with 0-100% B in chloroform over 8 column volumes and then 100% B for 7 column volumes, B is premixed 5:95 methanol:chloroform) to provide 1.5 g of an off white foam. This material was purified by HPFC (silica gel eluting with 0-10% B in ethyl acetate for 6 column volumes and then 10% B for 6 column volumes, B is 10% methanol in ethyl acetate) to provide 0.90 g of 3-[2-(ethoxymethyl)-1H-imidazo[4,5-c]quinolin-1-yl]-N,2,2-trimethylpropane-1-sulfonamide as a white foam.

Part B

Using the general method of Example 11 Part B, the material from Part A was oxidized and then aminated. The crude product was triturated sequentially with ethyl acetate and acetonitrile to provide 270 mg of 3-[4-amino-2-(ethoxymethyl)-1H-imidazo[4,5-c]quinolin-1-yl]-N,2,2-trimethylpropane-1-sulfonamide as a tan powder, mp 161-163° C. $^1$H NMR (300 MHz, DMSO-d$_6$): δ 8.38 (d, J=7.7 Hz, 1H), 7.59 (dd, J=1.2, 8.3 Hz, 1H), 7.42 (m, 1H), 7.21 (m, 1H), 7.02 (q, J=5.0 Hz, 1H), 6.61 (br s, 2H), 5.04-4.70 (m, 4H), 3.55 (br, 2H), 2.61 (dd, J=4.9 Hz, 3H), 1.14 (t, J=7.0 Hz, 3H), 1.03 (br s, 6H); MS (APCI) m/z 406 (M+H)+; Anal. calcd for $C_{19}H_{27}N_5O_3S$: C, 56.28; H, 6.71; N, 17.27. Found: C, 56.24; H, 6.69; N, 17.06.

Example 37

4-[4-Amino-2-(ethoxymethyl)-1H-imidazo[4,5-c]quinolin-1-yl]-N-isopropylbutane-1-sulfonamide

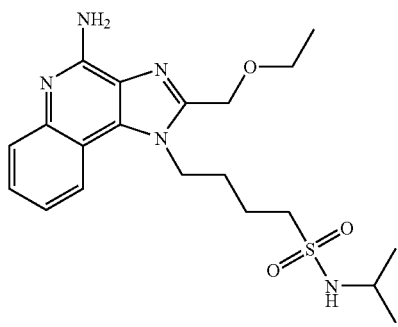 [SMILES: CCOCc1nc2c(N)nc3ccccc3c2n1CCCCS(=O)(=O)NC(C)C]

Part A

Using the general method of Example 11 Part A, 3-[2-(ethoxymethyl)-1H-imidazo[4,5-c]quinolin-1-yl]butane-1-sulfonyl chloride (4.1 g, 10.7 mmol, 1.0 eq) was reacted with isopropyl amine (0.70 g, 11.8 mmol, 1.1 eq) to provide 4.2 g of crude product. This material was purified by HPFC (silica gel eluting with 17% CMA in chloroform for 7 column volumes) to provide 2-(ethoxymethyl)-1H-imidazo[4,5-c]quinolin-1-yl]-N-isopropylbutane-1-sulfonamide.

Part B

Using the general method of Example 11 Part B, the material from Part A was oxidized and then aminated. The crude product was purified by trituration with acetonitrile followed by recrystallization from ethanol to provide 176 mg of product. The filtrate was concentrated and the residue was purified by HPFC (silica gel eluting with 0-20% CMA in chloroform over 8 column volumes and then with 20% CMA in chloroform for 9 column volumes) to provide 0.36 g of a light yellow oil. This material was triturated with ethanol (15 mL). The resulting solid was isolated by filtration, rinsed with ethanol (2×2 mL), and then dried under high vacuum at 80° C. to provide 214 mg of 4-[4-amino-2-(ethoxymethyl)-1H-imidazo[4,5-c]quinolin-1-yl]-N-isopropylbutane-1-sulfonamide as a white powder, mp 146-147° C. $^1$H NMR (300 MHz, DMSO-$d_6$): δ 8.05 (d, J=7.6 Hz, 1H), 7.62 (dd, J=1.1, 8.3 Hz, 1H), 7.45 (m, 1H), 7.26 (m, 1H), 6.99 (d, J=7.6 Hz, 1H), 6.58 (br s, 2H), 4.78 (s, 2H), 4.60 (m, 2H), 3.57 (q, J=7.0 Hz, 2H), 3.38 (m, 1H), 3.05 (m, 2H), 1.98 (m, 2H), 1.84 (m, 2H), 1.17 (t, J=7.0 Hz, 3H), 1.09 (d, J=6.5 Hz, 6H); MS (APCI) m/z 420 (M+H)+; Anal. calcd for $C_{20}H_{29}N_5O_3S$: C, 57.26; H, 6.97; N, 16.69. Found: C, 57.15; H, 6.96; N, 16.77.

Example 38

5-[4-amino-2-(ethoxymethyl)-6,7,8,9-tetrahydro-1H-imidazo[4,5-c]quinolin-1-yl]pentane-1-sulfonamide

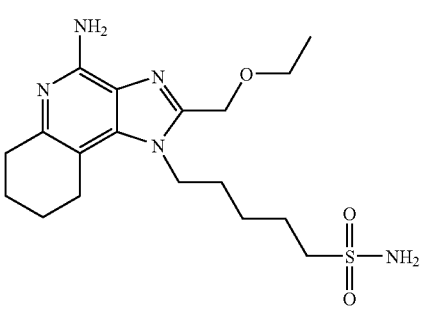 [SMILES: CCOCc1nc2c(N)nc3c(c2n1CCCCCS(N)(=O)=O)CCCC3]

5-[4-Amino-2-(ethoxymethyl)-1H-imidazo[4,5-c]quinolin-1-yl]pentane-1-sulfonamide (1.2 g) was reduced using the general method of Example 18. The crude product was placed under high vacuum until the clear oil had a steady weight of 1.2 g. The oil was combined with water (10 mL) and the pH was adjusted to pH 12 with 10% sodium hydroxide. The mixture was stirred for an hour and then filtered. The filtrate was adjusted to pH 7.5 with 6M hydrochloric acid. The resulting precipitate was isolated by filtration, recrystallized from methanol and then dried to provide a white solid. This material was dissolved in 12M hydrochloric acid (5 mL) and then stirred overnight. The mixture was chilled in an ice bath and then the pH was adjusted to pH 8 by slowly adding 6M potassium carbonate. The resulting suspension was stirred for 2 hours and the pH was adjusted to pH 12 with 10% sodium hydroxide. After stirring for an additional 2 hours the mixture was filtered. The filtrate was concentrated under reduced pressure. The residue was recrystallized from methanol and then dried under vacuum at 78° C. overnight to provide about 0.17 g of a white solid. This material was slurried with hot water and then allowed to cool to ambient temperature. The solid was isolated by filtration, rinsed with water (2×1 mL), air dried, and then dried under high vacuum at 110° C. for 15 minutes to provide 178 mg of 5-[4-amino-2-(ethoxymethyl)-6,7,8,9-tetrahydro-1H-imidazo[4,5-c]quinolin-1-yl]pentane-1-sulfonamide as a white powder, mp 203-205° C. $^1$H NMR (300 MHz, DMSO-$d_6$): δ 6.73 (s, 2H), 5.80 (s, 2H), 4.64 (s, 2H), 4.24 (m, 2H), 3.50 (q, J=7.0 Hz, 2H), 2.98 (m, 4H), 2.66 (m, 2H), 1.77 (m, 8), 1.47 (m, 2), 1.14 (t, J=7.0 Hz, 3; MS (APCI) m/z 396 (M+H)+; Anal. calcd for C18H29N5O3S: C, 54.66; H, 7.39; N, 17.71. Found: C, 54.59; H, 7.65; N, 17.88.

Example 39

N-Methyl 4-(4-amino-2-ethyl-6,7,8,9-tetrahydro-1H-imidazo[4,5-c]quinolin-1-yl)butane-1-sulfonamide

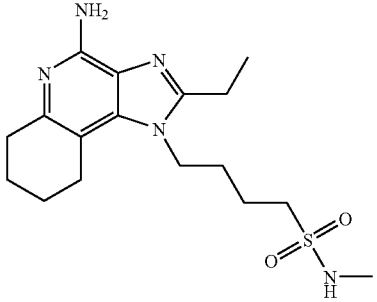 [SMILES: CCc1nc2c(N)nc3c(c2n1CCCCS(=O)(=O)NC)CCCC3]

N-Methyl 4-(4-amino-2-ethyl-1H-imidazo[4,5-c]quinolin-1-yl)butane-1-sulfonamide (420 mg) was reduced using the general method of Example 18. The reaction mixture was diluted with chloroform (5 mL) and methanol (10 mL) and then filtered through a layer of CELITE filter aid. The filter cake was rinsed with methanol (2×2 mL). The filtrate was concentrated under reduced pressure. The residue was combined with dichloromethane (50 mL) and saturated aqueous sodium bicarbonate (about 20 mL) and the mixture was stirred vigorously for 30 minutes. The organic layer was separated, dried over magnesium sulfate, and then concentrated under reduced pressure to provide 0.51 g of crude product as a white solid. A 50 mg portion was removed. The remaining material was combined with concentrated hydrochloric acid (about 10 mL) to provide a hazy solution. 6M potassium carbonate was added dropwise with cooling to maintain the temperature below 35-40° C. until the pH was about 10-11. The mixture was stirred for about 10 minutes. The resulting precipitate was isolated by filtration, rinsed with water (3×4 mL), and dried under high vacuum to provide 338 mg of a white solid. This material was purified by HPFC (silica gel eluting for 15 column volumes with 10/90 methanol/chloroform) to provide a clear oil. The oil was transferred to a vial with dichloromethane; partial evaporation of the solvent provided a white solid. This material was isolated by filtration, rinsed with dichloromethane (2×1 mL), and dried under high vacuum to provide 202 mg of a white crystalline solid. This material was dissolved in warm methanol (about 9 mL), concentrated under reduced pressure, and then dried under high vacuum to provide a clear oil. The oil was dissolved in 1/1 methano/ethyl acetate (about 8 mL), concentrated under reduced pressure, and then dried under high vacuum at 75° C. to provide 138 mg of N-methyl 4-(4-amino-2-ethyl-6,7,8,9-tetrahydro-1H-imidazo[4,5-c]quinolin-1-yl)butane-1-sulfonamide as a white powder, mp 166-170° C. $^1$H NMR (300 MHz, DMSO-$d_6$): δ 6.88 (q, J=5.0 Hz, 1H), 5.81 (br s, 2H), 4.20 (m, 2H), 3.06 (m, 2H), 2.94 (m, 2H), 2.82 (q, J=7.5 Hz, 2H), 2.66 (m, 2H), 2.56 (d, J=5.0 Hz, 3H), 1.76 (m, 8H), 1.32 (t, J=7.4 Hz, 3H); MS (APCI) m/z 366 (M+H)+;

Anal. calcd for C17H27N5O2S.0.50H2O: C, 54.52; H, 7.54; N, 18.70. Found: C, 54.82; H, 7.71; N, 18.58.

Example 40

4-[4-Amino-2-(ethoxymethyl)-1H-imidazo[4,5-c]quinolin-1-yl]-N-(pyridin-2-yl)butane-1-sulfonamide

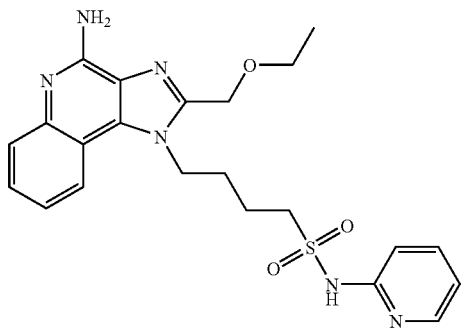 [SMILES: CCOCc1nc2c(N)nc3ccccc3c2n1CCCCS(=O)(=O)Nc1ccccn1]

Part A

Using the general method of Example 8 Part I, 1-(4-chlorobutyl)-2-ethoxymethyl 1H-imidazo[4,5-c]quinoline (21.2 g) was oxidized and then aminated to provide 26.8 g of crude product as a brown solid. This material was triturated with ethyl acetate (100 mL). The resulting off white solid was isolated by filtration, rinsed with ethyl acetate (3×30 mL), and dried under high vacuum to provide 15.18 g of 1-(4-chlorobutyl)-2-ethoxymethyl-1H-imidazo[4,5-c]quinolin-4-amine.

Part B

Using the general method of Example 8 Part E, 1-(4-chlorobutyl)-2-ethoxymethyl-1H-imidazo[4,5-c]quinolin-4-amine (2.00 g, 6.02 mmol) was reacted with potassium thioacetate (824 mg, 7.23 mmol) to provide 2.23 g of S-[4-(4-amino-2-ethoxymethyl-1H-imidazo[4,5-c]quinolin-1-yl)butyl]thioacetate as yellow powder.

Part C

The material from Part B was hydrolyzed using the general method of Example 8 Part F. The crude product was purified by flash chromatography (5×15 cm column of silica gel eluting with a gradient of 10 to 20% CMA in chloroform) to provide 1.43 g of 4-(4-amino-2-ethoxymethyl-1H-imidazo[4,5-c]quinolin-1-yl)butane-1-thiol.

Part D

Using the general method of Example 8 Part G, 4-(4-amino-2-ethoxymethyl-1H-imidazo[4,5-c]quinolin-1-yl)butane-1-thiol (380 mg) was oxidized to provide 280 mg of 4-(4-amino-2-ethoxymethyl-1H-imidazo[4,5-c]quinolin-1-yl)butane-1-sulfonyl chloride as a brown foam.

Part E

Solid 2-aminopyridine (265 mg, 4 eq) was added to the material from Part D (1 eq) followed by the rapid addition of pyridine (3.5 mL). The resulting solution was stirred at ambient temperature for 1 hr and then concentrated under reduced pressure. The residue was diluted with methanol (40 mL), concentrated under reduced pressure, and then dried under high vacuum. The residue was suspended in warm 1/1 methanol/dichloromethane, absorbed onto silica gel, and then purified by HPFC (eluting with a gradient of 0 to 35% CMA in chloroform over 15 column volumes and then with 35% CMA in chloroform for 8 column volumes) to provide 79 mg of a light yellow solid. This material was recrystallized from ethanol and then dried under high vacuum at 75-100° C. until analysis by $^1$H NMR indicated that the ethanol had been removed to provide 62 mg of 4-[4-amino-2-(ethoxymethyl)-1H-imidazo[4,5-c]quinolin-1-yl]-N-(pyridin-2-yl)butane-1-sulfonamide as light yellow powder, mp 197-200° C. $^1$H NMR (300 MHz, DMSO-d$_6$): δ10.89 (br s, 1H), 8.15 (d, J=5.4 Hz, 1H), 8.04 (d, J=7.8 Hz, 1H), 7.71 (ddd, J=1.9, 7.3, 8.5 Hz, 1H), 7.62 (dd, J=1.1, 8.3 Hz, 1H), 7.45 (m, 1H), 7.25 (m, 1H), 6.99 (m, 2H), 6.63 (br s, 2H), 4.76 (s, 2H), 4.59 (m, 2H), 3.51 (m, 4H), 1.94 (m, 4H), 1.11 (t, J=7.0 Hz, 3H); MS (APCI) m/z 455 (M+H)$^+$; Anal. calcd for C$_{22}$H$_{26}$N$_6$O$_3$S: C, 58.13; H, 5.77; N, 18.49. Found: C, 57.95; H, 5.71; N, 18.28.

Example 41

3-[4-Amino-2-(ethoxymethyl)-1H-imidazo[4,5-c]quinolin-1-yl]-N-(4-methoxybenzyl)-2,2-dimethyl-propane-1-sulfonamide

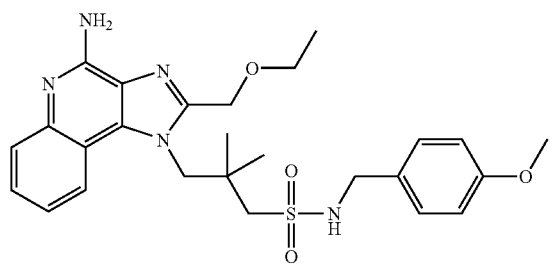 [SMILES: CCOCc1nc2c(N)nc3ccccc3c2n1CC(C)(C)CS(=O)(=O)NCc1ccc(OC)cc1]

Part A

4-Methoxybenzylamine (1.96 mL, 2.1 eq) was added to a solution of 3-(2-ethoxymethyl-1H-imidazo[4,5-c]quinolin-1-yl)-2,2-dimethylpropane-1-sulfonyl chloride (2.83 g, 1.0 eq) in dichloromethane (36 mL). The resulting suspension was stirred for 1 hour at ambient temperature then diluted with dichloromethane (100 mL) and washed with water (40 mL). The organic layer was dried over magnesium sulfate and concentrated under reduced pressure to provide 3.3 g of crude product as an oil. This material was purified by HPFC (silica gel eluting with 0-20% CMA in chloroform for 8 column volumes and then 20% CMA in chloroform for 3 column volumes) to provide 1.63 g of 3-[2-(ethoxymethyl)-1H-imidazo[4,5-c]quinolin-1-yl]-N-(4-methoxybenzyl)-2,2-dimethylpropane-1-sulfonamide as a light yellow foam.

Part B

Using the general method of Example 8 Part I, the material from Part A was oxidized and then aminated to provide 1.87 g of crude product as a tan foam. This material was purified by HPFC (silica gel eluting with 0-20% CMA in chloroform for 7 column volumes and then 20% CMA in chloroform for 5 column volumes) to provide 1.36 g of a tan foam. This material was triturated with methanol (10 mL), isolated by filtration, rinsed with methanol (3×7 mL), and then dried under high vacuum to provide 993 mg of 3-[4-amino-2-(ethoxymethyl)-1H-imidazo[4,5-c]quinolin-1-yl]-N-(4-methoxybenzyl)-2,2-dimethylpropane-1-sulfonamide as a white powder, mp 203-205° C. $^1$H NMR (300 MHz, DMSO-d$_6$): δ 8.36 (d, J=8.5 Hz, 1H), 7.61 (m, 2H), 7.42 (m, 1H), 7.23 (m, 3H), 6.92 (m, 2H), 6.61 (br s, 2H), 4.68 (br m, 4H), 4.09 (d, J=6.0 Hz, 2H), 3.75 (s, 3H), 3.55 (br, 2H), 1.14 (t, J=7.0 Hz, 3H), 1.03 (s, 6H); MS (APCI) m/z 512 (M+H)$^+$; Anal. calcd for C$_{26}$H$_{33}$N$_5$O$_4$S: C, 61.04; H, 6.50; N, 13.69. Found: C, 60.87; H, 6.60; N, 13.68.

Example 42

3-[4-Amino-2-(ethoxymethyl)-1H-imidazo[4,5-c]quinolin-1-yl]-2,2-dimethylpropane-1-sulfonamide

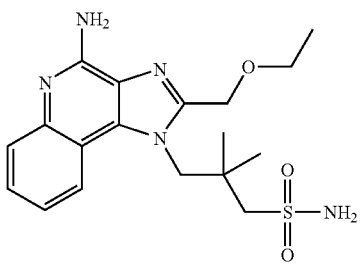 [SMILES: CCOCc1nc2c(N)nc3ccccc3c2n1CC(C)(C)CS(N)(=O)=O]

Trifluoroacetic acid (8 mL) and anisole (213 μL, 1.2 eq) were added sequentially to solid 3-[4-amino-2-(ethoxymethyl)-1H-imidazo[4,5-c]quinolin-1-yl]-N-(4-methoxybenzyl)-2,2-dimethylpropane-1-sulfonamide (834 mg, 1.63 mmol, 1.0 eq). The resulting solution was stirred at ambient temperature for 22 hours and then concentrated under reduced pressure. The residue was partitioned between dichloromethane (50 mL) and saturated aqueous sodium bicarbonate (about 35 mL). The layers were separated and the aqueous layer was extracted with chloroform (1×40 mL) and then with 10% methanol in chloroform (4×25 mL). The combined organics were dried over magnesium sulfate and then concentrated under reduced pressure to provide 1.15 g of a light yellow semisolid. This material was dissolved in 10% methanol in ethyl acetate, allowed to stand for 1 hour, and then filtered to remove a small amount of insoluble material which had formed on standing. The filtrate was concentrated under reduced pressure and then dried under high vacuum. The residue was triturated with methanol (about 5 mL), isolated by filtration, and rinsed with methanol (4×2 mL) to provide 475 mg of a yellow solid. This material was slurried with hot 5% methanol in chloroform (about 3-4 mL), allowed to cool to ambient temperature, isolated by filtration, rinsed with 5% methanol in chloroform (3×1 mL), and then dried under high vacuum to provide 395 mg of a light yellow solid. This process was repeated to provide 352 mg of 3-[4-amino-2-(ethoxymethyl)-1H-imidazo[4,5-c]quinolin-1-yl]-2,2-dimethylpropane-1-sulfonamide as light yellow powder, mp 229-231° C. $^1$H NMR (300 MHz, DMSO-d$_6$): δ8.36 (d, J=8.0 Hz, 1H), 7.59 (dd, J=1.1, 8.3 Hz, 1H), 7.42 (m, 1H), 7.21 (m, 1H), 7.02 (br s, 2H), 6.61 (br s, 2H), 4.70 (m, 4H), 3.55 (br, 2H), 1.14 (t, J=7.0 Hz, 3H), 1.05 (s, 6H); MS (EI) m/z 392

(M+H)+; Anal. calcd for $C_{18}H_{25}N_5O_3S$: C, 55.22; H, 6.44; N, 17.89. Found: C, 55.02; H, 6.64; N, 18.08.

Example 43

3-(4-Amino-2-methyl-6,7,8,9-tetrahydro-1H-imidazo[4,5-c]quinolin-1-yl)-2,2-dimethylpropane-1-sulfonamide

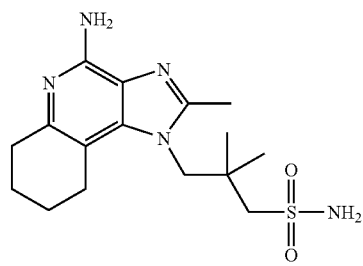 [SMILES: Cc1nc2c(N)nc3c(c2n1CC(C)(C)CS(N)(=O)=O)CCCC3]

Part A

Tosyl chloride (4.67 g, 1.2 eq.) and 4-dimethylaminopyridine (46 mg, 0.02 eq) were added sequentially to a suspension of 2,2-dimethyl-3-[(3-nitroquinolin-4-yl)amino]propanol (5.19 g, 18.8 mmol, 1.0 eq) in pyridine (35 mL). The reaction mixture was stirred at ambient temperature over night and then concentrated under reduced pressure. The residue was dilute with chloroform (300 mL) and washed with water (60 mL). The aqueous wash was extracted with dichloromethane (75 mL). The combined organics were dried over magnesium sulfate and then concentrated under reduced pressure to provide 7.88 g of 2,2-dimethyl-3-[(3-nitroquinolin-4-yl)amino] propyl p-toluenesulfonate as a yellow solid.

Part B

A mixture of 2,2-dimethyl-3-[(3-nitroquinolin-4-yl) amino]propyl p-toluenesulfonate (5.37 g, 12.5 mmol), 10% palladium on carbon (530 mg), and acetonitrile was placed under hydrogen pressure (50 psi, $3.4\times10^5$ Pa) on a Parr apparatus for 6 hours. The reaction mixture was filtered through a layer of CELITE filter aid. The filter cake was rinsed with acetonitrile until the rinse was colorless. The filtrate was concentrated under reduced pressure to provide 4.50 g of crude 3-[(3-aminoquinolin-4-yl)amino]-2,2-dimethylpropyl p-toluenesulfonate as an orange oil.

Part C

Trimethyl orthoacetate (1.72 mL, 1.2 eq) and pyridine hydrochloride (130 mg, 0.1 eq) were added sequentially to a suspension of the material from tart B (1 eq) in toluene (111 mL). The reaction mixture was heated at 100° C. for 1 hour, cooled to ambient temperature overnight, combined with the material from another run, and then concentrated under reduced pressure to provide 5.50 g of crude product as a brown foam. This material was purified by HPFC (silica gel eluting with a gradient of 0 to 20% CMA in chloroform over 7 column volumes and then with 20% CMA in chloroform for 5 column volumes) to provide 3.94 g of 3-(2-methyl-1H-imidazo[4,5-c]quinolin-1-yl)-2,2-dimethylpropyl p-toluenesulfonate as a white foam.

Part D

Potassium thiocyanate (155 mg, 2.0 eq) was added to a solution of 3-(2-methyl-1H-imidazo[4,5-c]quinolin-1-yl)-2,2-dimethylpropyl p-toluenesulfonate (338 mg, 0.80 mmol, 1.0 eq) in n-propanol (4.0 mL). The reaction mixture was heated in an EMRYS OPTIMIZER microwave synthesizer (available from Biotage, Inc, Charlottesville, Va., USA) at 190° C. for 20 minutes. The reaction was repeated. The combined reaction mixtures were concentrated under reduced pressure. The residue was partitioned between chloroform (100 mL) and water (75 mL). The organic layer was washed with brine (50 mL), dried over magnesium sulfate, and concentrated under reduced pressure to provide 0.50 g of an oil. The oil was purified by HPFC (silica gel eluting with a gradient of 0 to 20% CMA in chloroform over 8 column volumes and then with 20% CMA in chloroform for 4 column volumes) to provide 390 mg of 3-(2-methyl-1H-imidazo[4,5-c] quinolin-1-yl)-2,2-dimethylpropyl thiocyanate as a clear oil.

Part E

Sodium borohydride (95 mg, 2.0 eq) was added to a chilled (0° C.) solution of the material from Part D (1.0 eq) in ethanol (12 mL). The reaction mixture was allowed to warm to ambient temperature. After 3 hours the reaction was quenched with hydrochloric acid (about 1 mL of 7 M), stirred for several minutes, and then concentrated under reduced pressure. The residue was dissolved in dichloromethane (125 mL) then water (75 mL) was added. The mixture was made basic (pH about 7) with saturated sodium bicarbonate. The organic layer was separated, dried over magnesium sulfate, and concentrated under reduced pressure to provide 330 mg of 3-(2-methyl-1H-imidazo[4,5-c]quinolin-1-yl)-2,2-dimethylpropane-1-thiol as an oil.

Part F

A solution of benzyltrimethylammonium chloride (663 mg, 3.4 eq) and trichloroisocyanuric acid (268 mg, 1.1 eq) in dichloromethane (5 mL) was stirred at ambient temperature for 45 minutes and then added dropwise over a period of about 2 minutes to a chilled (0° C.) solution of the material from Part E (1.0 eq) and water (47 µL, 2.5 eq) in dichloromethane (6 mL). After 45 minutes 4-methoxybenzylamine (0.89 mL, 6.5 eq) was added and then the reaction mixture was allowed to warm to ambient temperature and stirred for 2 hours. The reaction mixture was diluted with dichloromethane (125 mL), washed with water (2×200 mL), dried over magnesium sulfate, and then concentrated under reduced pressure to provide 0.67 g of crude product as an oil. The oil was purified by HPFC (silica gel eluting with a gradient of 0 to 20% CMA in chloroform over 8 column volumes and then with 20% CMA in chloroform for 4 column volumes) and combined with the material from another run to provide 757 mg of N-(4-methoxybenzyl) 3-(2-methyl-1H-imidazo[4,5-c]quinolin-1-yl)-2,2-dimethylpropane-1-sulfonamide as a white foam.

Part G

3-Chloroperoxybenzoic acid (490 mg, 1.2 eq based on a 70% titer) was added to a solution of the material from Part F (1.0 eq) in chloroform (16 mL). The reaction mixture was stirred at ambient temperature for 40 minutes and then combined with concentrated ammonium hydroxide (4 mL). Tosyl chloride (379 mg, 1.2 eq) was added in portions over a period of several minutes. The reaction mixture was stirred for 1 hour and then diluted with chloroform (100 mL) and washed with water (50 mL). The aqueous layer was extracted with dichloromethane (30 mL). The combined organics were dried over magnesium sulfate and concentrated under reduced pressure to provide 0.89 g of crude product as a brown foam. This material was purified by HPFC (silica gel eluting with a gradient of 0 to 30% CMA in chloroform over 8 column volumes and then with 30% CMA in chloroform for 8 column volumes) to provide 500 mg of 3-(4-amino-2-methyl-1H-imidazo[4,5-c]quinolin-1-yl)-N-(4-methxoybenzyl)-2,2-dimethylpropane-1-sulfonamide as a tan/orange powder.

Part H

The material from Part G was dissolved in trifluoroacetic acid (11 mL) and stirred at ambient temperature for 4.5 hours.

Platinum (IV) oxide (500 mg) was added and the mixture was placed under hydrogen pressure (50 psi, 3.4×10$^5$ Pa) on a Parr apparatus for 20 hours. The reaction mixture was filtered through a layer of CELITE filter aid. The filter cake was rinsed sequentially with trifluoroacetic acid (2×8 mL), methanol (3×15 mL), and 1/1 methanol/chloroform (2×15 mL). The filtrate was concentrated under reduced pressure. The residue was partitioned between dichloromethane (150 mL) and water (75 mL) and the aqueous pH was adjusted to about 8-9. The layers were separated. The aqueous layer was extracted with dichloromethane (3×50 mL) and 10% methanol in dichloromethane (2×50 mL). The combined organics were dried over magnesium sulfate and concentrated under reduced pressure to provide 0.44 g of crude product as a brown semisolid. This material was purified by HPFC (silica gel eluting with a gradient of 20 to 50% CMA in chloroform over 5 column volumes and then with 50% CMA in chloroform for 6 column volumes) to provide 180 mg of a white semisolid. This material was crystallized from hot isopropanol (about 8 mL), isolated by filtration, rinsed with isopropanol (3×2 mL), and dried under high vacuum to provide 131 mg of a white solid. This material was dissolved in hot methanol, the methanol solution was concentrated, and the solid was isolated by filtration. This procedure was repeated using ethanol and the resulting solid was dried under high vacuum at 100° C. for 48 hours to provide about 125 mg of 3-(4-amino-2-methyl-6,7,8,9-tetrahydro-1H-imidazo[4,5-c]quinolin-1-yl)-2,2-dimethylpropane-1-sulfonamide as an off white solid, mp 242-243° C. (dec.). $^1$H NMR (300 MHz, DMSO-d$_6$): δ 6.97 (s, 2H), 5.71 (s, 2H), 4.38 (br, 2H), 3.15 (br, 2H), 2.88 (br, 2H), 2.66 (br, 2H), 1.74 (br, 4H), 1.01 (s, 6H); MS (EI) m/z 352 (M+H)$^+$; Anal. calcd for C$_{16}$H$_{25}$N$_5$O$_2$S.0.10 C$_3$H$_8$O.0.22H$_2$O: C, 54.17; H, 7.32; N, 19.38. Found: C, 54.01; H, 7.16; N, 19.44.

Exemplary Compounds

Certain exemplary compounds, including some of those described above in the Examples, have the following Formulas Ic, IIc, IIIa, and IVa and the following R$_1$, R$_1'$, X', and R$_2$ substituents, wherein each line of the table represents a specific compound.

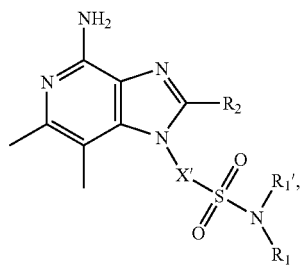

Ic

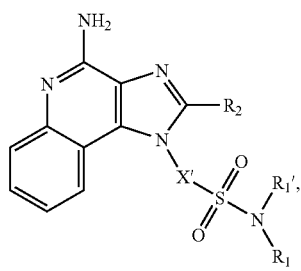

IIc

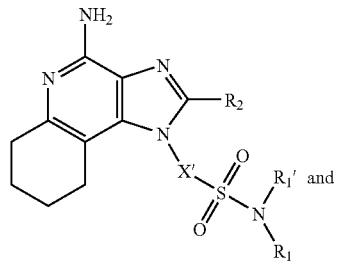

IIIa

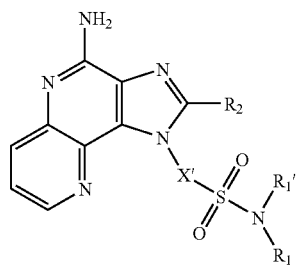

IVa

| R$_1$ | R$_1'$ | X' | R$_2$ |
|---|---|---|---|
| hydrogen | hydrogen | —(CH$_2$)$_2$— | methyl |
| hydrogen | hydrogen | —(CH$_2$)$_2$— | ethyl |
| hydrogen | hydrogen | —(CH$_2$)$_2$— | n-propyl |
| hydrogen | hydrogen | —(CH$_2$)$_2$— | n-butyl |
| hydrogen | hydrogen | —(CH$_2$)$_2$— | ethoxymethyl |
| hydrogen | hydrogen | —(CH$_2$)$_2$— | 2-methoxyethyl |
| hydrogen | hydrogen | —(CH$_2$)$_2$— | hydroxymethyl |
| hydrogen | hydrogen | —(CH$_2$)$_2$— | 2-hydroxyethyl |
| hydrogen | hydrogen | —(CH$_2$)$_3$— | methyl |
| hydrogen | hydrogen | —(CH$_2$)$_3$— | ethyl |
| hydrogen | hydrogen | —(CH$_2$)$_3$— | n-propyl |
| hydrogen | hydrogen | —(CH$_2$)$_3$— | n-butyl |
| hydrogen | hydrogen | —(CH$_2$)$_3$— | ethoxymethyl |
| hydrogen | hydrogen | —(CH$_2$)$_3$— | 2-methoxyethyl |
| hydrogen | hydrogen | —(CH$_2$)$_3$— | hydroxymethyl |
| hydrogen | hydrogen | —(CH$_2$)$_3$— | 2-hydroxyethyl |
| hydrogen | hydrogen | —(CH$_2$)$_4$— | methyl |
| hydrogen | hydrogen | —(CH$_2$)$_4$— | ethyl |
| hydrogen | hydrogen | —(CH$_2$)$_4$— | n-propyl |
| hydrogen | hydrogen | —(CH$_2$)$_4$— | n-butyl |
| hydrogen | hydrogen | —(CH$_2$)$_4$— | ethoxymethyl |
| hydrogen | hydrogen | —(CH$_2$)$_4$— | 2-methoxyethyl |
| hydrogen | hydrogen | —(CH$_2$)$_4$— | hydroxymethyl |
| hydrogen | hydrogen | —(CH$_2$)$_4$— | 2-hydroxyethyl |
| hydrogen | hydrogen | —(CH$_2$)$_5$— | methyl |
| hydrogen | hydrogen | —(CH$_2$)$_5$— | ethyl |
| hydrogen | hydrogen | —(CH$_2$)$_5$— | n-propyl |
| hydrogen | hydrogen | —(CH$_2$)$_5$— | n-butyl |
| hydrogen | hydrogen | —(CH$_2$)$_5$— | ethoxymethyl |
| hydrogen | hydrogen | —(CH$_2$)$_5$— | 2-methoxyethyl |
| hydrogen | hydrogen | —(CH$_2$)$_5$— | hydroxymethyl |
| hydrogen | hydrogen | —(CH$_2$)$_5$— | 2-hydroxyethyl |
| hydrogen | hydrogen | —CH$_2$C(CH$_3$)$_2$CH$_2$— | methyl |
| hydrogen | hydrogen | —CH$_2$C(CH$_3$)$_2$CH$_2$— | ethyl |
| hydrogen | hydrogen | —CH$_2$C(CH$_3$)$_2$CH$_2$— | n-propyl |
| hydrogen | hydrogen | —CH$_2$C(CH$_3$)$_2$CH$_2$— | n-butyl |
| hydrogen | hydrogen | —CH$_2$C(CH$_3$)$_2$CH$_2$— | ethoxymethyl |
| hydrogen | hydrogen | —CH$_2$C(CH$_3$)$_2$CH$_2$— | 2-methoxyethyl |
| hydrogen | hydrogen | —CH$_2$C(CH$_3$)$_2$CH$_2$— | hydroxymethyl |
| hydrogen | hydrogen | —CH$_2$C(CH$_3$)$_2$CH$_2$— | 2-hydroxyethyl |
| isopropyl | hydrogen | —(CH$_2$)$_2$— | methyl |
| isopropyl | hydrogen | —(CH$_2$)$_2$— | ethyl |
| isopropyl | hydrogen | —(CH$_2$)$_2$— | n-propyl |
| isopropyl | hydrogen | —(CH$_2$)$_2$— | n-butyl |
| isopropyl | hydrogen | —(CH$_2$)$_2$— | ethoxymethyl |
| isopropyl | hydrogen | —(CH$_2$)$_2$— | 2-methoxyethyl |
| isopropyl | hydrogen | —(CH$_2$)$_2$— | hydroxymethyl |
| isopropyl | hydrogen | —(CH$_2$)$_2$— | 2-hydroxyethyl |
| isopropyl | hydrogen | —(CH$_2$)$_3$— | methyl |

| | | | |
|---|---|---|---|
| isopropyl | hydrogen | —(CH₂)₃— | ethyl |
| isopropyl | hydrogen | —(CH₂)₃— | n-propyl |
| isopropyl | hydrogen | —(CH₂)₃— | n-butyl |
| isopropyl | hydrogen | —(CH₂)₃— | ethoxymethyl |
| isopropyl | hydrogen | —(CH₂)₃— | 2-methoxyethyl |
| isopropyl | hydrogen | —(CH₂)₃— | hydroxymethyl |
| isopropyl | hydrogen | —(CH₂)₃— | 2-hydroxyethyl |
| isopropyl | hydrogen | —(CH₂)₄— | methyl |
| isopropyl | hydrogen | —(CH₂)₄— | ethyl |
| isopropyl | hydrogen | —(CH₂)₄— | n-propyl |
| isopropyl | hydrogen | —(CH₂)₄— | n-butyl |
| isopropyl | hydrogen | —(CH₂)₄— | ethoxymethyl |
| isopropyl | hydrogen | —(CH₂)₄— | 2-methoxyethyl |
| isopropyl | hydrogen | —(CH₂)₄— | hydroxymethyl |
| isopropyl | hydrogen | —(CH₂)₄— | 2-hydroxyethyl |
| isopropyl | hydrogen | —(CH₂)₅— | methyl |
| isopropyl | hydrogen | —(CH₂)₅— | ethyl |
| isopropyl | hydrogen | —(CH₂)₅— | n-propyl |
| isopropyl | hydrogen | —(CH₂)₅— | n-butyl |
| isopropyl | hydrogen | —(CH₂)₅— | ethoxymethyl |
| isopropyl | hydrogen | —(CH₂)₅— | 2-methoxyethyl |
| isopropyl | hydrogen | —(CH₂)₅— | hydroxymethyl |
| isopropyl | hydrogen | —(CH₂)₅— | 2-hydroxyethyl |
| isopropyl | hydrogen | —CH₂C(CH₃)₂CH₂— | methyl |
| isopropyl | hydrogen | —CH₂C(CH₃)₂CH₂— | ethyl |
| isopropyl | hydrogen | —CH₂C(CH₃)₂CH₂— | n-propyl |
| isopropyl | hydrogen | —CH₂C(CH₃)₂CH₂— | n-butyl |
| isopropyl | hydrogen | —CH₂C(CH₃)₂CH₂— | ethoxymethyl |
| isopropyl | hydrogen | —CH₂C(CH₃)₂CH₂— | 2-methoxyethyl |
| isopropyl | hydrogen | —CH₂C(CH₃)₂CH₂— | hydroxymethyl |
| isopropyl | hydrogen | —CH₂C(CH₃)₂CH₂— | 2-hydroxyethyl |
| methyl | hydrogen | —(CH₂)₂— | methyl |
| methyl | hydrogen | —(CH₂)₂— | ethyl |
| methyl | hydrogen | —(CH₂)₂— | n-propyl |
| methyl | hydrogen | —(CH₂)₂— | n-butyl |
| methyl | hydrogen | —(CH₂)₂— | ethoxymethyl |
| methyl | hydrogen | —(CH₂)₂— | 2-methoxyethyl |
| methyl | hydrogen | —(CH₂)₂— | hydroxymethyl |
| methyl | hydrogen | —(CH₂)₂— | 2-hydroxyethyl |
| methyl | hydrogen | —(CH₂)₃— | methyl |
| methyl | hydrogen | —(CH₂)₃— | ethyl |
| methyl | hydrogen | —(CH₂)₃— | n-propyl |
| methyl | hydrogen | —(CH₂)₃— | n-butyl |
| methyl | hydrogen | —(CH₂)₃— | ethoxymethyl |
| methyl | hydrogen | —(CH₂)₃— | 2-methoxyethyl |
| methyl | hydrogen | —(CH₂)₃— | hydroxymethyl |
| methyl | hydrogen | —(CH₂)₃— | 2-hydroxyethyl |
| methyl | hydrogen | —(CH₂)₄— | methyl |
| methyl | hydrogen | —(CH₂)₄— | ethyl |
| methyl | hydrogen | —(CH₂)₄— | n-propyl |
| methyl | hydrogen | —(CH₂)₄— | n-butyl |
| methyl | hydrogen | —(CH₂)₄— | ethoxymethyl |
| methyl | hydrogen | —(CH₂)₄— | 2-methoxyethyl |
| methyl | hydrogen | —(CH₂)₄— | hydroxymethyl |
| methyl | hydrogen | —(CH₂)₄— | 2-hydroxyethyl |
| methyl | hydrogen | —(CH₂)₅— | methyl |
| methyl | hydrogen | —(CH₂)₅— | ethyl |
| methyl | hydrogen | —(CH₂)₅— | n-propyl |
| methyl | hydrogen | —(CH₂)₅— | n-butyl |
| methyl | hydrogen | —(CH₂)₅— | ethoxymethyl |
| methyl | hydrogen | —(CH₂)₅— | 2-methoxyethyl |
| methyl | hydrogen | —(CH₂)₅— | hydroxymethyl |
| methyl | hydrogen | —(CH₂)₅— | 2-hydroxyethyl |
| methyl | hydrogen | —CH₂C(CH₃)₂CH₂— | methyl |
| methyl | hydrogen | —CH₂C(CH₃)₂CH₂— | ethyl |
| methyl | hydrogen | —CH₂C(CH₃)₂CH₂— | n-propyl |
| methyl | hydrogen | —CH₂C(CH₃)₂CH₂— | n-butyl |
| methyl | hydrogen | —CH₂C(CH₃)₂CH₂— | ethoxymethyl |
| methyl | hydrogen | —CH₂C(CH₃)₂CH₂— | 2-methoxyethyl |
| methyl | hydrogen | —CH₂C(CH₃)₂CH₂— | hydroxymethyl |
| methyl | hydrogen | —CH₂C(CH₃)₂CH₂— | 2-hydroxyethyl |
| methyl | methyl | —(CH₂)₂— | methyl |
| methyl | methyl | —(CH₂)₂— | ethyl |
| methyl | methyl | —(CH₂)₂— | n-propyl |
| methyl | methyl | —(CH₂)₂— | n-butyl |
| methyl | methyl | —(CH₂)₂— | ethoxymethyl |
| methyl | methyl | —(CH₂)₂— | 2-methoxyethyl |
| methyl | methyl | —(CH₂)₂— | hydroxymethyl |
| methyl | methyl | —(CH₂)₂— | 2-hydroxyethyl |
| methyl | methyl | —(CH₂)₃— | methyl |
| methyl | methyl | —(CH₂)₃— | ethyl |
| methyl | methyl | —(CH₂)₃— | n-propyl |
| methyl | methyl | —(CH₂)₃— | n-butyl |
| methyl | methyl | —(CH₂)₃— | ethoxymethyl |
| methyl | methyl | —(CH₂)₃— | 2-methoxyethyl |
| methyl | methyl | —(CH₂)₃— | hydroxymethyl |
| methyl | methyl | —(CH₂)₃— | 2-hydroxyethyl |
| methyl | methyl | —(CH₂)₄— | methyl |
| methyl | methyl | —(CH₂)₄— | ethyl |
| methyl | methyl | —(CH₂)₄— | n-propyl |
| methyl | methyl | —(CH₂)₄— | n-butyl |
| methyl | methyl | —(CH₂)₄— | ethoxymethyl |
| methyl | methyl | —(CH₂)₄— | 2-methoxyethyl |
| methyl | methyl | —(CH₂)₄— | hydroxymethyl |
| methyl | methyl | —(CH₂)₄— | 2-hydroxyethyl |
| methyl | methyl | —(CH₂)₅— | methyl |
| methyl | methyl | —(CH₂)₅— | ethyl |
| methyl | methyl | —(CH₂)₅— | n-propyl |
| methyl | methyl | —(CH₂)₅— | n-butyl |
| methyl | methyl | —(CH₂)₅— | ethoxymethyl |
| methyl | methyl | —(CH₂)₅— | 2-methoxyethyl |
| methyl | methyl | —(CH₂)₅— | hydroxymethyl |
| methyl | methyl | —(CH₂)₅— | 2-hydroxyethyl |
| methyl | methyl | —CH₂C(CH₃)₂CH₂— | methyl |
| methyl | methyl | —CH₂C(CH₃)₂CH₂— | ethyl |
| methyl | methyl | —CH₂C(CH₃)₂CH₂— | n-propyl |
| methyl | methyl | —CH₂C(CH₃)₂CH₂— | n-butyl |
| methyl | methyl | —CH₂C(CH₃)₂CH₂— | ethoxymethyl |
| methyl | methyl | —CH₂C(CH₃)₂CH₂— | 2-methoxyethyl |
| methyl | methyl | —CH₂C(CH₃)₂CH₂— | hydroxymethyl |
| methyl | methyl | —CH₂C(CH₃)₂CH₂— | 2-hydroxyethyl |
| morpholine | | —(CH₂)₂— | methyl |
| morpholine | | —(CH₂)₂— | ethyl |
| morpholine | | —(CH₂)₂— | n-propyl |
| morpholine | | —(CH₂)₂— | n-butyl |
| morpholine | | —(CH₂)₂— | ethoxymethyl |
| morpholine | | —(CH₂)₂— | 2-methoxyethyl |
| morpholine | | —(CH₂)₂— | hydroxymethyl |
| morpholine | | —(CH₂)₂— | 2-hydroxyethyl |
| morpholine | | —(CH₂)₃— | methyl |
| morpholine | | —(CH₂)₃— | ethyl |
| morpholine | | —(CH₂)₃— | n-propyl |
| morpholine | | —(CH₂)₃— | n-butyl |
| morpholine | | —(CH₂)₃— | ethoxymethyl |
| morpholine | | —(CH₂)₃— | 2-methoxyethyl |
| morpholine | | —(CH₂)₃— | hydroxymethyl |
| morpholine | | —(CH₂)₃— | 2-hydroxyethyl |
| morpholine | | —(CH₂)₄— | methyl |
| morpholine | | —(CH₂)₄— | ethyl |
| morpholine | | —(CH₂)₄— | n-propyl |
| morpholine | | —(CH₂)₄— | n-butyl |
| morpholine | | —(CH₂)₄— | ethoxymethyl |
| morpholine | | —(CH₂)₄— | 2-methoxyethyl |
| morpholine | | —(CH₂)₄— | hydroxymethyl |
| morpholine | | —(CH₂)₄— | 2-hydroxyethyl |
| morpholine | | —(CH₂)₅— | methyl |
| morpholine | | —(CH₂)₅— | ethyl |
| morpholine | | —(CH₂)₅— | n-propyl |
| morpholine | | —(CH₂)₅— | n-butyl |
| morpholine | | —(CH₂)₅— | ethoxymethyl |
| morpholine | | —(CH₂)₅— | 2-methoxyethyl |
| morpholine | | —(CH₂)₅— | hydroxymethyl |
| morpholine | | —(CH₂)₅— | 2-hydroxyethyl |
| morpholine | | —CH₂C(CH₃)₂CH₂— | methyl |
| morpholine | | —CH₂C(CH₃)₂CH₂— | ethyl |
| morpholine | | —CH₂C(CH₃)₂CH₂— | n-propyl |
| morpholine | | —CH₂C(CH₃)₂CH₂— | n-butyl |
| morpholine | | —CH₂C(CH₃)₂CH₂— | ethoxymethyl |
| morpholine | | —CH₂C(CH₃)₂CH₂— | 2-methoxyethyl |

Cytokine Induction in Human Cells

Compounds of the invention have been found to modulate cytokine biosynthesis by inducing the production of interferon α and/or tumor necrosis factor α when tested using the method described below.

An in vitro human blood cell system is used to assess cytokine induction. Activity is based on the measurement of interferon and tumor necrosis factor (α) (IFN and TNF, respectively) secreted into culture media as described by Testerman et. al. in "Cytokine Induction by the Immunomodulators Iniquimod and S-27609", Journal of Leukocyte Biology, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4\times10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30-0.014 μM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the formula (Ia):

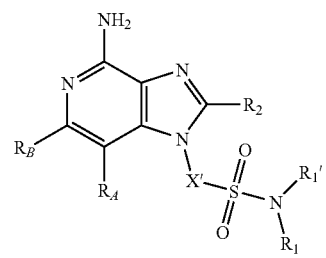

wherein:
X' is selected from the group consisting of —CH($R_9$)—, —CH($R_9$)-alkylene, and —CH($R_9$)-alkenylene-;
$R_1$ and $R_1'$ are independently selected from the group consisting of:
hydrogen and
alkyl;
$R_2$ is selected from the group consisting of:
hydrogen,
alkyl,
hydroxyalkyl, and
alkyloxyalkyl;
$R_9$ is selected from the group consisting of hydrogen and alkyl;
$R_A$ and $R_B$ taken together form either a fused 6-membered aryl ring that is unsubstituted or substituted by one or more $R_a$ groups, or a fused 6-membered saturated ring that is unsubstituted or substituted by one or more $R_c$ groups;
$R_a$ is selected from the group consisting of:
fluoro,
alkyl,
haloalkyl,
alkoxy, and
—N($R_9$)$_2$; and
$R_c$ is selected from the group consisting of:
halogen,
hydroxy,
alkyl,
alkenyl,
haloalkyl,
alkoxy,
alkylthio, and
—N($R_9$)$_2$;
or a pharmaceutically acceptable salt thereof.

2. A compound of the formula (II):

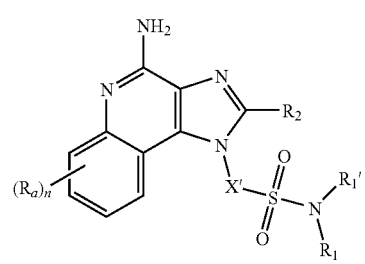

wherein:
X' is selected from the group consisting of —CH(R$_9$)—, —CH(R$_9$)-alkylene, and —CH(R$_9$)-alkenylene-;
R$_1$ and R$_1$' are independently selected from the group consisting of:
hydrogen and
alkyl;
R$_2$ is selected from the group consisting of:
hydrogen,
alkyl,
hydroxyalkyl; and
alkyloxyalkyl;
R$_9$ is selected from the group consisting of hydrogen and alkyl;
R$_a$ is selected from the group consisting of fluoro, alkyl, haloalkyl, alkoxy, and —N(R$_9$)$_2$; and
n is 0 to 4;
or a pharmaceutically acceptable salt thereof.

3. A compound of the formula (IIa):

(IIa)

wherein:
X' is selected from the group consisting of —CH(R$_9$)—, —CH(R$_9$)-alkylene, and —CH(R$_9$)-alkenylene-;
R$_2$ is selected from the group consisting of:
hydrogen,
alkyl,
hydroxyalkyl, and
alkyloxyalkyl;
R$_9$ is selected from the group consisting of hydrogen and alkyl;
R$_a$ is selected from the group consisting of fluoro, alkyl, haloalkyl, alkoxy, and —N(R$_9$)$_2$; and
n is 0 to 4;
or a pharmaceutically acceptable salt thereof.

4. A compound of the formula (III):

(III)

wherein:
X' is selected from the group consisting of —CH(R$_9$)—, —CH(R$_9$)-alkylene, and —CH(R$_9$)-alkenylene-;
R$_1$ and R$_1$' are independently selected from the group consisting of:
hydrogen and
alkyl;
R$_2$ is selected from the group consisting of:
hydrogen,
alkyl,
hydroxyalkyl, and
alkyloxyalkyl;
R$_9$ is selected from the group consisting of hydrogen and alkyl;
R$_c$ is selected from the group consisting of halogen, hydroxy, alkyl, alkenyl, haloalkyl, alkoxy, alkylthio, and —N(R$_9$)$_2$; and
n is 0 to 4;
or a pharmaceutically acceptable salt thereof.

5. The compound or salt of claim 2 wherein n is 0.

6. The compound or salt of claim 1 wherein R$_1$' is hydrogen or alkyl, and R$_1$ is hydrogen alkyl.

7. The compound or salt of claim 1 wherein R$_1$' is hydrogen or methyl, and R$_1$ is selected from the group consisting of hydrogen, methyl, ethyl, propyl, and butyl.

8. The compound or salt of claim 7 wherein R$_1$ and R$_1$' are both hydrogen.

9. The compound or salt of claim 1 wherein R$_2$ is selected from the group consisting of hydrogen, C$_{1-4}$ alkyl, C$_{1-4}$ alkyl-O—C$_{1-4}$ alkylenyl, and HO—C$_{1-3}$ alkylenyl.

10. The compound or salt of claim 9 wherein R$_2$ is selected from the group consisting of hydrogen, methyl, ethyl, n-propyl, n-butyl, hydroxymethyl, 2-hydroxyethyl, ethoxymethyl, and 2-methoxyethyl.

11. The compound or salt of claim 1 wherein X' is —(CH$_2$)$_{1-7}$—.

12. The compound or salt of claim 1 wherein X' is —(CH$_2$)—C(CH$_3$)$_2$—.

13. A pharmaceutical composition comprising a therapeutically effective amount of a compound or salt of claim 1 in combination with a pharmaceutically acceptable carrier.

14. A method of cytokine biosynthesis in an animal comprising administering an effective amount of a compound or salt of claim 1 to the animal, wherein the cytokine is a TNF alpha or IFN alpha.

15. The compound or salt of claim 2 wherein R$_1$' is hydrogen or alkyl, and R$_1$ is hydrogen.

16. The compound or salt of claim 2 wherein R$_1$' is hydrogen or methyl, and R$_1$ is selected from the group consisting of hydrogen, methyl, ethyl, propyl, and butyl.

17. The compound or salt of claim 2 wherein R$_2$ is selected from the group consisting of hydrogen, C$_{1-4}$ alkyl, C$_{1-4}$ alkyl-O—C$_{1-4}$ alkylenyl, and HO—C$_{1-3}$ alkylenyl.

18. The compound or salt of claim 17 wherein R$_2$ is selected from the group consisting of hydrogen, methyl, ethyl, n-propyl, n-butyl, hydroxymethyl, 2-hydroxyethyl, ethoxymethyl, and 2-methoxyethyl.

19. The compound or salt of claim 2 wherein X' is —(CH$_2$)$_{1-7}$—.

20. The compound or salt of claim 2 wherein X' is —(CH$_2$)—C(CH$_3$)$_2$—.

21. The compound or salt of claim 3 wherein n is 0.

22. The compound or salt of claim 3 wherein R$_2$ is selected from the group consisting of hydrogen, C$_{1-4}$ alkyl, C$_{1-4}$ alkyl-O—C$_{1-4}$ alkylenyl, and HO—C$_{1-3}$ alkylenyl.

23. The compound or salt of claim 22 wherein R$_2$ is selected from the group consisting of hydrogen, methyl, ethyl, n-propyl, n-butyl, hydroxymethyl, 2-hydroxyethyl, ethoxymethyl, and 2-methoxyethyl.

24. The compound or salt of claim 3 wherein X' is —$(CH_2)_{1-7}$—.

25. The compound or salt of claim 3 wherein X' is —$(CH_2)$—$C(CH_3)_2$—.

26. The compound or salt of claim 4 wherein n is 0.

27. The compound or salt of claim 4 wherein $R_1$' is hydrogen or methyl, and $R_1$ is selected from the group consisting of hydrogen, methyl, ethyl, propyl, and butyl.

28. The compound or salt of claim 4 wherein $R_1$ and $R_1$' are both hydrogen.

29. The compound or salt of claim 4 wherein $R_2$ is selected from the group consisting of hydrogen, methyl, ethyl, n-propyl, n-butyl, hydroxymethyl, 2-hydroxyethyl, ethoxymethyl, and 2-methoxyethyl.

30. The compound or salt of claim 4 wherein X' is —$(CH_2)_{1-7}$—.

31. A pharmaceutical composition comprising a therapeutically effective amount of a compound or salt of claim 2 in combination with a pharmaceutically acceptable carrier.

32. A method of cytokine biosynthesis in an animal comprising administering an effective amount of a compound or salt of claim 2 to the animal, wherein the cytokine is a TNF alpha or IFN alpha.

33. A pharmaceutical composition comprising a therapeutically effective amount of a compound or salt of claim 3 in combination with a pharmaceutically acceptable carrier.

34. A method of cytokine biosynthesis in an animal comprising administering an effective amount of a compound or salt of claim 3 to the animal, wherein the cytokine is a TNF alpha or IFN alpha.

35. A pharmaceutical composition comprising a therapeutically effective amount of a compound or salt of claim 4 in combination with a pharmaceutically acceptable carrier.

36. A method of cytokine biosynthesis in an animal comprising administering an effective amount of a compound or salt of claim 4 to the animal, wherein the cytokine is a TNF alpha or IFN alpha.

* * * * *

UNITED STATES PATENT AND TRADEMARK OFFICE
CERTIFICATE OF CORRECTION

PATENT NO.        : 8,735,421 B2
APPLICATION NO.   : 10/596897
DATED             : May 27, 2014
INVENTOR(S)       : Jason Bonk Page 1 of 3

It is certified that error appears in the above-identified patent and that said Letters Patent is hereby corrected as shown below:

In the Specification

Column 23
Line 44, Delete "alkyl," and insert -- alkynyl, --, therefor.

Column 39
Line 26, Delete "interfering," and insert -- interfering --, therefor.

Column 40
Line 11, Delete "III," and insert -- VIII, --, therefor.
Line 15, Delete "particularly" and insert -- (particularly --, therefor.
Line 16, Delete "VI," and insert -- VII, --, therefor.
Line 21, Delete "particularly" and insert -- (particularly --, therefor.
Line 22, Delete "VII," and insert -- VIII, --, therefor.
Line 67, Delete "R'" and insert -- $R_1'$ --, therefor.

Column 41
Line 12, Delete "R'" and insert -- $R_1'$ --, therefor.
Line 18, Delete "particularly" and insert -- (particularly --, therefor.
Line 22, Delete "particularly" and insert -- (particularly --, therefor.
Line 28, Delete "m," and insert -- III, --, therefor.

Column 43
Line 15, Delete "-N($R_4$)-" and insert -- -N($R_4$)-. --, therefor.

Column 45
Line 32, Delete "XXII." and insert -- XXIII. --, therefor.
Line 58, Delete "XXII" and insert -- XXIII --, therefor.

Signed and Sealed this
Tenth Day of March, 2015

Michelle K. Lee
*Deputy Director of the United States Patent and Trademark Office*

CERTIFICATE OF CORRECTION (continued)
U.S. Pat. No. 8,735,421 B2

Column 46
Line 18, Delete "XIV" and insert -- XXIV --, therefor.
Line 20, Delete "XXV" and insert -- XXIV --, therefor.
Line 44, Delete "1," and insert -- I, --, therefor.

Column 51
Line 44, Delete "m," and insert -- III, --, therefor.
Line 53, Delete "XXXII" and insert -- XXXIII --, therefor.
Line 56, Delete "m," and insert -- III, --, therefor.
Line 57, Delete "XX" and insert -- XXXIV --, therefor.

Column 52
Line 35, Delete "m," and insert -- III, --, therefor.
Line 38, Delete "XXVII." and insert -- XXXVII. --, therefor.
Line 39, Delete "XVI" and insert -- XXXVI --, therefor.

Column 58
Line 56, Delete "anine" and insert -- amine --, therefor.

Column 64
Line 63, Delete "XXI." and insert -- XXII. --, therefor.

Column 65
Line 5, Delete "XXI" and insert -- XXII --, therefor.

Column 68
Line 31, Delete "orthopoxyirus" and insert -- orthopoxvirus --, therefor.
Line 46, Delete "Chiamydia," and insert -- Chlamydia, --, therefor.
Line 48, Delete "Mydobacterium," and insert -- Mycobacterium, --, therefor.

Column 69
Line 3, Delete "greata;" and insert -- areata; --, therefor.
Line 23, Delete "adenovirs," and insert -- adenovirus, --, therefor.

Column 83
Line 41, Delete "nm/z" and insert -- m/z --, therefor.

Column 94
Line 18, Delete "3000" and insert -- 300 --, therefor.

Column 96
Line 26, Delete "21)," and insert -- 2H), --, therefor.

Column 97
Line 56, Delete "61" and insert -- 6M --, therefor.

Column 106
Line 60, Delete "extracted," and insert -- extracted --, therefor.

Column 110
Line 25, Delete "warned" and insert -- warmed --, therefor.

Column 120
Line 65, Delete "211," and insert -- 2H), --, therefor.
Line 67, Delete "8)," and insert -- 8H), --, therefor.
Line 67, Delete "2)," and insert -- 2H), --, therefor.

Column 121
Line 1, Delete "3;" and insert -- 3H), --, therefor.
Line 59, Delete "methano" and insert -- methanol --, therefor.

Column 125
Line 50, Delete "tart" and insert -- Part --, therefor.

Column 131
Line 1, Delete "(a)" and insert -- (α) --, therefor.
Line 4, Delete "Iniquimod" and insert -- Imiquimod --, therefor.